US008048081B2

(12) United States Patent
Shaolian et al.

(10) Patent No.: US 8,048,081 B2
(45) Date of Patent: Nov. 1, 2011

(54) TRANSPEDICULAR INTERVERTEBRAL DISK ACCESS METHODS AND DEVICES

(75) Inventors: Samuel M. Shaolian, Newport Beach, CA (US); George P. Teitelbaum, Santa Monica, CA (US)

(73) Assignee: Warsaw Orthopedic, Inc., Warsaw, IN (US)

(*) Notice: Subject to any disclaimer, the term of this patent is extended or adjusted under 35 U.S.C. 154(b) by 1163 days.

(21) Appl. No.: 10/607,494

(22) Filed: Jun. 25, 2003

(65) Prior Publication Data

US 2005/0261684 A1 Nov. 24, 2005

Related U.S. Application Data

(63) Continuation of application No. 10/420,422, filed on Apr. 22, 2003, now Pat. No. 7,318,826, which is a continuation of application No. PCT/US03/09285, filed on Mar. 25, 2003.

(60) Provisional application No. 60/424,942, filed on Nov. 8, 2002.

(51) Int. Cl.
*A61B 17/70* (2006.01)

(52) U.S. Cl. .................................. 606/90; 623/17.16

(58) Field of Classification Search .............. 606/90, 606/93, 99, 62–68; 600/201, 207, 208, 210, 600/215, 216, 219, 224, 225; 623/17.11–17.16
See application file for complete search history.

(56) References Cited

U.S. PATENT DOCUMENTS

| 4,608,965 | A | * | 9/1986 | Anspach et al. | ............. | 600/101 |
|---|---|---|---|---|---|---|
| 4,672,964 | A | | 6/1987 | Dee et al. | | |
| 5,178,625 | A | | 1/1993 | Groshong et al. | | |
| 5,192,327 | A | * | 3/1993 | Brantigan | .................. | 623/17.11 |
| 5,235,966 | A | * | 8/1993 | Jamner | ......................... | 600/204 |
| 5,269,785 | A | | 12/1993 | Bonutti | | |
| 5,591,170 | A | | 1/1997 | Spievack et al. | | |
| 6,045,579 | A | * | 4/2000 | Hochshuler et al. | ....... | 623/17.16 |
| 6,059,734 | A | | 5/2000 | Yoon et al. | | |
| 6,102,950 | A | * | 8/2000 | Vaccaro | ..................... | 623/17.16 |
| 6,110,127 | A | | 8/2000 | Suzuki et al. | | |
| 6,136,014 | A | | 10/2000 | Sirimanne et al. | | |
| 6,159,211 | A | * | 12/2000 | Boriani et al. | ................ | 606/279 |
| 6,264,695 | B1 | | 7/2001 | Stoy | | |
| 6,371,988 | B1 | | 4/2002 | Pafford et al. | | |
| 6,436,098 | B1 | | 8/2002 | Michelson | | |
| 6,488,684 | B2 | * | 12/2002 | Bramlet et al. | ................. | 606/62 |
| 6,562,047 | B2 | * | 5/2003 | Ralph et al. | .................... | 606/99 |
| 6,579,291 | B1 | * | 6/2003 | Keith et al. | ................. | 606/86 A |
| 6,613,044 | B2 | * | 9/2003 | Carl | ................................ | 606/21 |
| 6,740,090 | B1 | * | 5/2004 | Cragg et al. | .................... | 606/79 |
| 6,740,093 | B2 | * | 5/2004 | Hochschuler et al. | .......... | 606/94 |
| 6,852,126 | B2 | * | 2/2005 | Ahlgren | ..................... | 623/17.11 |

(Continued)

OTHER PUBLICATIONS

International Search Report issued by the European Patent Office on Apr. 7, 2006, in International Application No. PCT/US2005/043185 (7 pages).

*Primary Examiner* — Thomas C. Barrett
*Assistant Examiner* — Christopher Beccia

(57) ABSTRACT

Methods and devices for treating diseases and conditions that change the spacial relationship between the vertebral bodies and the intervertebral disks, or that cause instability of the vertebral column, or both, and a method and devices that allow the surgeon to access the intervertebral space to restore a more normal three-dimensional configuration of the space, with or without additionally fusing two adjacent vertebrae.

20 Claims, 41 Drawing Sheets

U.S. PATENT DOCUMENTS

| | | |
|---|---|---|
| 7,311,713 B2 * | 12/2007 | Johnson et al. .................. 606/90 |
| 7,318,826 B2 * | 1/2008 | Teitelbaum et al. ............. 606/80 |
| 7,344,564 B2 * | 3/2008 | Sweeney ..................... 623/17.15 |
| 7,491,236 B2 * | 2/2009 | Cragg et al. ............... 623/17.11 |
| 2002/0183758 A1 | 12/2002 | Middleton et al. |
| 2003/0171812 A1 * | 9/2003 | Grunberg et al. .......... 623/17.11 |
| 2003/0195514 A1 * | 10/2003 | Trieu et al. ....................... 606/61 |
| 2004/0167625 A1 * | 8/2004 | Beyar et al. ................ 623/11.11 |

\* cited by examiner

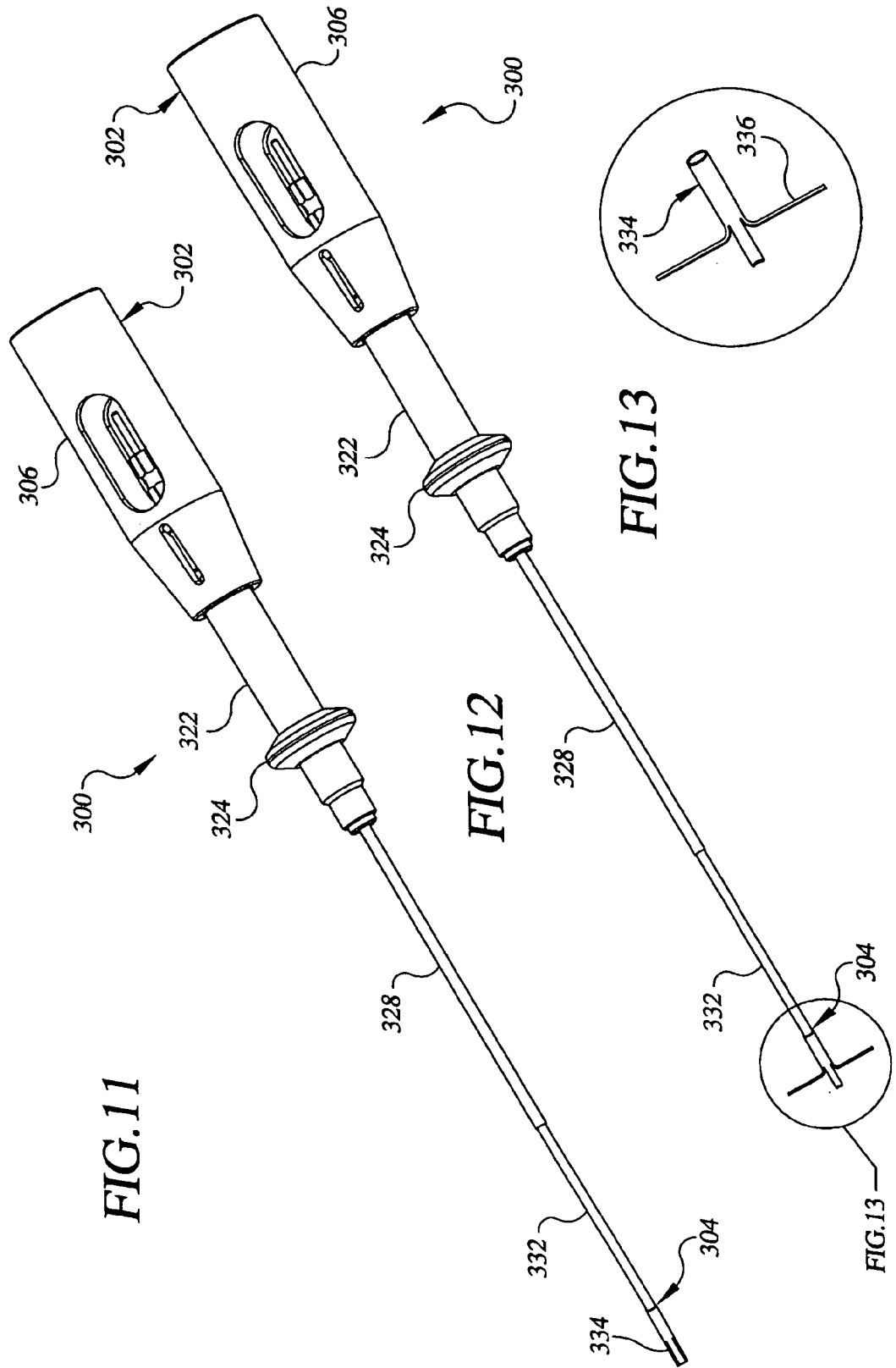

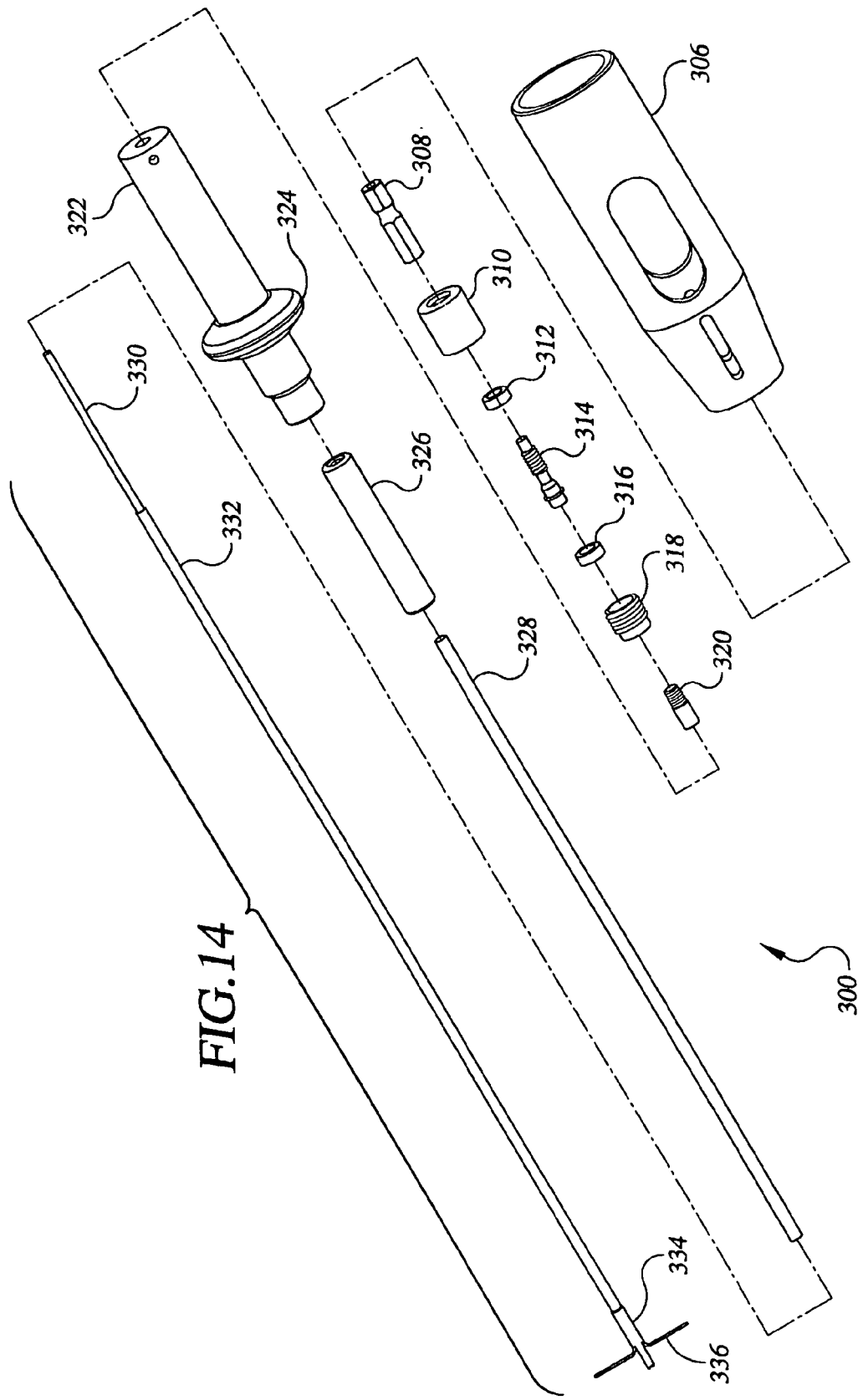

TRANSPEDICULAR INTERVERTEBRAL DISK ACCESS METHODS AND DEVICES

CROSS-REFERENCE TO RELATED APPLICATION

The present application is a continuation of U.S. patent application Ser. No. 10/420,422, filed Apr. 22, 2003 now U.S. Pat. No. 7,318,826 entitled "Transpedicular Intervertebral Disk Access Methods and Devices," that is a continuation of PCT patent application PCT/US03/09285, filed Mar. 25, 2003, entitled "Transpedicular Intervertebral Disk Access Methods And Devices," that claims the benefit of U.S. provisional patent application 60/424,942, filed Nov. 8, 2002, entitled "Transpedicular Intervertebral Body Fusion," the contents of which are incorporated herein by reference in their entirety.

BACKGROUND

The human vertebral bodies and intervertebral disks are subject to a variety of diseases and conditions that change the spacial relationship between the vertebral bodies and the intervertebral disks, causing pain, disability or both. Many of these diseases and conditions also cause instability of the vertebral column. Among these diseases and conditions are degenerated, herniated, or degenerated and herniated intervertebral disks, degenerative scoliosis, disk or vertebral body infections, space occupying lesions such as malignancies, spinal stenosis, spondylosis, spondylolisthesis, and vertebral instability. Additionally, the vertebral bodies and intervertebral disks are subject to injuries, including vertebral fractures due to trauma or osteoporosis, and to surgical manipulations, that change the spacial relationship between the vertebral bodies and the intervertebral disks, causing pain, disability or both, and that cause instability of the vertebral column.

Surgical treatment of diseases and conditions affecting the spacial relationship between the vertebral bodies and the intervertebral disks have traditionally involved open fusion procedures that include making a lengthy incision through the tissues overlying the spinous processes, thereby directly accessing the vertebrae to mechanically fuse two adjacent vertebrae. These procedures result in considerable post-operative pain and a significant incidence of post-operative morbidity, including infection. Further, traditional procedures do not allow the surgeon to directly access the intervertebral space to restore the more normal three-dimensional configuration of the space.

Therefore, there is a need for a new method for treating diseases and conditions that changes the spacial relationship between two vertebral bodies and the intervertebral disk between the two vertebral bodies, or that cause instability of the vertebral column, or both, that is associated with less post-operative pain and a lower incidence of post-operative morbidity. Further, there is a need for a new method for treating diseases and conditions that change the spacial relationship between the vertebral bodies and the intervertebral disks, or that cause instability of the vertebral column, or both, that allows the surgeon to directly access the intervertebral space to mechanically fuse two adjacent vertebrae.

SUMMARY

According to one embodiment of the present invention, there is provided a flexible drill comprising a drilling tip, and capable of orienting the drilling tip at a predetermined position after accessing a material to be drilled through a substantially straight passage having a long axis, where the predetermined position is at least 10° off of the long axis of the substantially straight passage. In one embodiment, the flexible drill further comprises a lower sub-assembly connected to an upper sub-assembly, where the upper sub-assembly comprises the drilling tip. In another embodiment, the lower sub-assembly comprises a spin luer lock, a retainer tube, a piston anchor, a piston level, a piston, a distal O-ring and a proximal O-ring, and the upper sub-assembly further comprises a guiding tube, a barrel knob, a barrel, a threaded adapter, a liner, a bearing housing, a flexible shaft, a distal bearing, a proximal bearing, a collet, a bearing cap and a motor receptacle. In another embodiment, the upper sub-assembly comprises a guiding tube comprising a proximal segment having a central axis and a distal segment having a distal end, the drilling tip is connected to the distal end of the distal segment; and the guiding tube comprises a substance that has been processed to return to a shape such that the distal segment has a radius of curvature sufficient to cause the drilling tip at the end of the distal segment to orient at between about 10° and 150° off of the central axis of the proximal segment when the guiding tube is not subject to distortion. In another embodiment, the upper sub-assembly comprises a guiding tube comprising a proximal segment having a central axis and a distal segment having a distal end, the drilling tip is connected to the distal end of the distal segment, and the guiding tube comprises a substance that has been processed to return to a shape such that the predetermined position of the drilling tip is at least 10° off of the long axis of the substantially straight passage. In another embodiment, the flexible drill further comprises a guiding tube comprising a proximal segment having a central axis and a distal segment having a distal end, the drilling tip is connected to the distal end of the distal segment, and the guiding tube comprises a substance that has been processed to return to a shape where the distal segment has a radius of curvature sufficient to cause the drilling tip at the end of the distal segment to orient at between about 10° and 150° off of the central axis of the proximal segment when the guiding tube is not subject to distortion. In another embodiment, the flexible drill further comprises a guiding tube comprising a proximal segment having a central axis and a distal segment having a distal end, the drilling tip is connected to the distal end of the distal segment, and the guiding tube comprises a substance that has been processed to return to a shape such that the predetermined position of the drilling tip is at least 10° off of the long axis of the substantially straight passage. In another embodiment, the flexible drill further comprises a guiding tip attached to the drilling tip. In another embodiment, the flexible drill further comprises an axial channel for accepting a guide wire.

According to another embodiment of the present invention, there is provided a flexible drill comprising a guiding tube having a proximal segment having a central axis and a distal segment having a distal end, and a drilling tip is connected to the distal end of the distal segment, the guiding tube comprises a substance that has been processed to return to a shape where the distal segment has a radius of curvature sufficient to cause the drilling tip at the end of the distal segment to orient at between about 10° and 150° off of the central axis of the proximal segment when the guiding tube is not subject to distortion. In one embodiment, the flexible drill further comprises a guiding tip attached to the drilling tip. In another embodiment, the flexible drill further comprises an axial channel for accepting a guide wire.

According to another embodiment of the present invention, there is provided a flexible comprising a lower sub-assembly connected to an upper sub-assembly, the lower sub-assembly comprises a spin luer lock, a retainer tube, a piston anchor, a piston level, a piston, a distal O-ring and a proximal O-ring, and the upper sub-assembly comprises a drilling tip, guiding tube, a barrel knob, a barrel, a threaded adapter, a liner, a bearing housing, a flexible shaft, a distal bearing, a proximal bearing, a collet, a bearing cap and a motor receptacle, the guiding tube comprising a proximal segment having a central axis and a distal segment having a distal end, the drilling tip is connected to the distal end of the distal segment, and the guiding tube comprises a substance that has been processed to return to a shape where the distal segment has a radius of curvature sufficient to cause the drilling tip at the end of the distal segment to orient at between about 10° and 150° off of the central axis of the proximal segment when the guiding tube is not subject to distortion. In one embodiment, the flexible drill further comprises a guiding tip attached to the drilling tip. In another embodiment, the flexible drill further comprises an axial channel for accepting a guide wire.

According to another embodiment of the present invention, there is provided a method of drilling a material comprising a) providing a flexible drill according to the present invention, b) advancing the drill through a substantially straight passage until the drilling tip accesses the material to be drilled, thereby orienting the drilling tip at the predetermined position, and c) actuating the drill. In one embodiment, the method further comprises passing a guide wire through the drill either before actuating the flexible drill, after actuating the flexible drill, or both before and after actuating the flexible drill. In another embodiment, the material to be drilled is selected from the group consisting of bone, cartilage and intervertebral disk. In another embodiment, the method further comprises inserting a sheath into the substantially straight passage before inserting the flexible drill and then inserting the flexible drill through the sheath.

According to one embodiment of the present invention, there is provided a flexible drill comprising a drilling tip, and capable of orienting the drilling tip at a predetermined position after accessing a material to be drilled through a substantially straight passage having a long axis, where the predetermined position is at least 10° off of the long axis of the substantially straight passage. In one embodiment, the flexible drill further comprises a lower sub-assembly connected to an upper sub-assembly, where the upper sub-assembly comprises the drilling tip. In another embodiment, the lower sub-assembly comprises a spin luer lock, a retainer tube, a piston anchor, a piston level, a piston, a distal O-ring and a proximal O-ring, and the upper sub-assembly further comprises a guiding tube, a barrel knob, a barrel, a threaded adapter, a liner, a bearing housing, a flexible shaft, a distal bearing, a proximal bearing, a collet, a bearing cap and a motor receptacle. In another embodiment, the upper sub-assembly comprises a guiding tube comprising a proximal segment having a central axis and a distal segment having a distal end, the drilling tip is connected to the distal end of the distal segment; and the guiding tube comprises a substance that has been processed to return to a shape such that the distal segment has a radius of curvature sufficient to cause the drilling tip at the end of the distal segment to orient at between about 10° and 150° off of the central axis of the proximal segment when the guiding tube is not subject to distortion. In another embodiment, the upper sub-assembly comprises a guiding tube comprising a proximal segment having a central axis and a distal segment having a distal end, the drilling tip is connected to the distal end of the distal segment, and the guiding tube comprises a substance that has been processed to return to a shape such that the predetermined position of the drilling tip is at least 10° off of the long axis of the substantially straight passage. In another embodiment, the flexible drill further comprises a guiding tube comprising a proximal segment having a central axis and a distal segment having a distal end, the drilling tip is connected to the distal end of the distal segment, and the guiding tube comprises a substance that has been processed to return to a shape where the distal segment has a radius of curvature sufficient to cause the drilling tip at the end of the distal segment to orient at between about 10° and 150° off of the central axis of the proximal segment when the guiding tube is not subject to distortion. In another embodiment, the flexible drill further comprises a guiding tube comprising a proximal segment having a central axis and a distal segment having a distal end, the drilling tip is connected to the distal end of the distal segment, and the guiding tube comprises a substance that has been processed to return to a shape such that the predetermined position of the drilling tip is at least 10° off of the long axis of the substantially straight passage. In another embodiment, the flexible drill further comprises a guiding tip attached to the drilling tip. In another embodiment, the flexible drill further comprises an axial channel for accepting a guide wire.

According to another embodiment of the present invention, there is provided a flexible drill comprising a guiding tube having a proximal segment having a central axis and a distal segment having a distal end, and a drilling tip is connected to the distal end of the distal segment, the guiding tube comprises a substance that has been processed to return to a shape where the distal segment has a radius of curvature sufficient to cause the drilling tip at the end of the distal segment to orient at between about 10° and 150° off of the central axis of the proximal segment when the guiding tube is not subject to distortion. In one embodiment, the flexible drill further comprises a guiding tip attached to the drilling tip. In another embodiment, the flexible drill further comprises an axial channel for accepting a guide wire.

According to another embodiment of the present invention, there is provided a flexible comprising a lower sub-assembly connected to an upper sub-assembly, the lower sub-assembly comprises a spin luer lock, a retainer tube, a piston anchor, a piston level, a piston, a distal O-ring and a proximal O-ring, and the upper sub-assembly comprises a drilling tip, guiding tube, a barrel knob, a barrel, a threaded adapter, a liner, a bearing housing, a flexible shaft, a distal bearing, a proximal bearing, a collet, a bearing cap and a motor receptacle, the guiding tube comprising a proximal segment having a central axis and a distal segment having a distal end, the drilling tip is connected to the distal end of the distal segment, and the guiding tube comprises a substance that has been processed to return to a shape where the distal segment has a radius of curvature sufficient to cause the drilling tip at the end of the distal segment to orient at between about 10° and 150° off of the central axis of the proximal segment when the guiding tube is not subject to distortion. In one embodiment, the flexible drill further comprises a guiding tip attached to the drilling tip. In another embodiment, the flexible drill further comprises an axial channel for accepting a guide wire.

According to another embodiment of the present invention, there is provided a method of drilling a material. The method comprises, a) providing a flexible drill according to the present invention, b) advancing the drill through a substantially straight passage until the drilling tip accesses the material to be drilled, thereby orienting the drilling tip at the predetermined position, and c) actuating the drill. In one embodiment, the method further comprises passing a guide wire through the drill either before actuating the flexible drill, after actuating the flexible drill, or both before and after actuating the flexible drill. In another embodiment, the material to be drilled is selected from the group consisting of bone, cartilage and intervertebral disk. In another embodiment, the method further comprises inserting a sheath into the substantially straight passage before inserting the flexible drill and then inserting the flexible drill through the sheath.

According to another embodiment of the present invention, there is provided a method of drilling a material, comprising a) providing a drill according to the present invention, b) advancing the flexible drill under distortion into the material, c) removing the distortion from the flexible drill, d) actuating the flexible drill. In one embodiment, the method further comprises passing a guide wire through the flexible drill either before actuating the flexible drill, after actuating the flexible drill, or both before and after actuating the flexible drill. In another embodiment, the material to be drilled is selected from the group consisting of bone, cartilage and intervertebral disk.

According to another embodiment of the present invention, there is provided a cutting device comprising a blade connected to the distal end of a flexible shaft, where the cutting device can be inserted into a material to be cut after accessing the material through a channel comprising a substantially straight proximal section having a long axis and a distal section having a long axis, and the long axis of the distal section is curved, or where the long axis of the distal section is substantially straight but varies at least about 10° off of the long axis of the proximal section. In one embodiment, the blade pivots from a first, insertion position to a 5 second, cutting position. In another embodiment, the cutting device further comprises a locking sleeve surrounding at least part of the flexible shaft, the blade has one or more than one notch, the locking sleeve can be advanced distally and retracted proximally, and advancement distally causes the locking sleeve to engage with the one or more than one notch, thereby locking the blade into the cutting position, and retraction proximally causes the locking sleeve to disengage from the one or more than one notch, thereby unlocking the blade from the cutting position. In another embodiment, the cutting device further comprises a sheath having a beveled distal end and surrounding at least part of the flexible shaft, the flexible shaft can be advanced distally and retracted proximally relative to the sheath, and retraction proximally of the flexible shaft causes the blade to disengage from the locking sleeve and pivot to the insertion position. In another embodiment, the blade has a circumferential cutting edge. In another embodiment, the cutting device further comprises a proximal end comprising a motor adapter for connecting the cutting device to a motor drive, and a distal end, where the blade is attached.

According to another embodiment of the present invention, there is provided a cutting device comprising a) a pivoting blade connected to the distal end of a flexible shaft, and b) a locking sleeve surrounding at least part of the flexible shaft, the blade pivots from a first, insertion position to a second, cutting position, where the blade has one or more than one notch, where the locking sleeve can be advanced distally and retracted proximally, and where advancement distally causes the locking sleeve to engage with the one or more than one notch, thereby locking the blade into the cutting position, and retraction proximally causes the locking sleeve to disengage from the one or more than one notch, thereby unlocking the blade from the cutting position. In one embodiment, the cutting device comprising further comprises a sheath having a beveled distal end and surrounding at least part of the flexible shaft, where the flexible shaft can be advanced distally and retracted proximally relative to the sheath, and where retraction proximally of the flexible shaft causes the blade to disengage from the locking sleeve and pivot to the insertion position. In one embodiment, the cutting device can be inserted into a material to be cut after accessing the material through a channel comprising a substantially straight proximal section having a long axis and a distal section having a long axis, and the long axis of the distal section is curved, or where the long axis of the distal section is substantially straight but varies at least about 10° off of the long axis of the proximal section. In another embodiment, the blade has a circumferential cutting edge. In another embodiment, the cutting device further comprises a proximal end comprising a motor adapter for connecting the cutting device to a motor drive, and a distal end, where the blade is attached.

According to another embodiment of the present invention, there is provided a method of cutting a material comprising a) providing the cutting device of the present invention, b) inserting the cutting device into the material after accessing the material through a channel comprising a substantially straight proximal section having a long axis and a distal section having a long axis, and c) actuating the cutting device, where the long axis of the distal section is curved, or where the long axis of the distal section is substantially straight but varies at least about 10° off of the long axis of the proximal section. In one embodiment, the method further comprises advancing and retracting the cutting device withing the material. In another embodiment, the method further comprises inserting a sheath into the channel before inserting the cutting device, and inserting the cutting device through the sheath.

According to another embodiment of the present invention, there is provided a method of cutting a material comprising a) providing the cutting device of the present invention, b) inserting the cutting device into the material, c) advancing the locking sleeve distally to engage with the one or more than one notch, thereby locking the blade into the cutting position, d) actuating the cutting device, e) deactuating the cutting device, f) retracting the locking sleeve proximally to disengage from the one or more than one notch, thereby unlocking the blade from the cutting position, and g) removing the cutting device from the material. In one embodiment, inserting the cutting device comprises advancing the cutting device through a channel comprising a substantially straight proximal section having a long axis and a distal section having a long axis, and the long axis of the distal section is curved, or where the long axis of the distal section is substantially straight but varies at least about 10° off of the long axis of the proximal section. In another embodiment, he method further comprises advancing and retracting the cutting device withing the material. In another embodiment, the method further comprises inserting a sheath into the channel before inserting the cutting device, and inserting the cutting device through the sheath.

According to another embodiment of the present invention, there is provided an enucleation device. The enucleation device comprises a proximal end, a distal end comprising a cutting cap comprising a plurality of deformable blades, and a shaft between the proximal end and the cutting cap, where the plurality of deformable blades can cut material in a space when the blades not deformed, after accessing the space through a passage while the blades are deformed, and where the passage has a smaller cross-sectional area than the lateral cross-sectional area of the undeformed blades while the blades are cutting the material.

In one embodiment, the shaft is flexible. In another embodiment, the enucleation further comprises an axial guidewire lumen between the proximal end and the distal end.

According to another embodiment of the present invention, there is provided a method of cutting material in a space. The method comprises a) providing an enucleation according to the present invention, b) accessing the space with the enucleation device, and c) actuating the device, thereby effecting cutting of the material. In one embodiment, the method further comprises deforming the blades before actuating the device, and accessing the space through a passage while the blades are deformed, where the passage has a smaller cross-sectional area than the lateral cross-sectional area of the undeformed blades while the blades are cutting the material. In another embodiment, the passage is curved. In another embodiment, the method further comprises advancing and retracting the cutting device in the space to cut additional material. In another embodiment, accessing the space comprises advancing the cutting device over a guide wire. In another embodiment, the material cut is selected from the group consisting of intervertebral disk and vertebral body endplate material. In another embodiment, accessing the space comprises advancing the enucleation device through a transpedicular access passage in a vertebra.

According to another embodiment of the present invention, there is provided a method of cutting material in a space. The method comprises a) providing the enucleation device of the present invention, b) creating a passage to access the space, c) deforming the blades to fit through the passage, d) advancing the enucleation device through the passage until the cutting cap passes into the space, thereby allowing the blades to expand to their undeformed shape, and e) actuating the enucleation device, thereby effecting cutting of the material, where the passage has a smaller cross-sectional area than the lateral cross-sectional area of the undeformed blades while the blades are cutting the material. In one embodiment, the method, further comprises advancing and retracting the cutting device in the space to cut additional material. In another embodiment, advancing the cutting device through the passage comprises advancing the cutting device over a guide wire. In another embodiment, the passage is curved. In another embodiment, the material cut is intervertebral disk. In another embodiment, the material cut is vertebral body endplate material. In another embodiment, the passage is a transpedicular access passage in a vertebra.

According to another embodiment of the present invention, there is provided a fusion agent containment device for containing a fusion agent comprising a band or mesh of thin, biocompatible, deformable material having shape memory configured to expand into a substantially circular or oval shape when undeformed. In one embodiment, the fusion agent containment further comprises a biocompatible sealant coating the band.

According to another embodiment of the present invention, there is provided a method of fusing two adjacent vertebrae comprising a) creating a chamber within the intervertebral disk space between two adjacent vertebrae, b) providing a fusion agent containment device according to the present invention, c) placed the fusion agent containment device within the chamber, thereby allowing the fusion agent containment device to expand, d) filling the fusion agent containment device with a fusion agent, and e) allowing the fusion agent to fuse the two adjacent vertebrae. In one embodiment, the method further comprises additionally fusing the two adjacent vertebrae with a second procedure.

According to another embodiment of the present invention, there is provided a distraction system for distracting two adjacent vertebrae comprising a) an introducer comprising a proximal insertion portion and a distal anchoring portion comprising a plurality of barbs, and b) a plurality of deformable, spacing components, where each spacing component has a central opening and a plurality of extensions, and each spacing component configured to stack onto the insertion portion of the introducer. In one embodiment, the plurality of extensions is selected from the group consisting of three extensions and four extensions.

According to another embodiment of the present invention, there is provided a distraction system for distracting two adjacent vertebrae comprising a) a proximal connecting portion, b) a distal distracting portion comprising a plurality of strips, each strip is deformable from an extended configuration to a curled configuration, each strip has a proximal end and a distal end, the proximal ends of the strips are joined to the proximal connecting portion connected at their proximal end to the proximal connecting portion. In one embodiment, the proximal connecting portion comprises mesh. In another embodiment, each strip tapers from the proximal end to the distal end.

According to another embodiment of the present invention, there is provided a distraction system for distracting two adjacent vertebrae comprising a) a barbed plug having a central axis and comprising a central portion and a plurality of barbs, b) a ratchet device having a central axis and comprising a series of transversely separated strips connected at one end, where the barbs extend outward from the axial center of the barbed plug when undeformed, and contract toward the axial center of the barbed plug when deformed, and where the strips uncoil away from the central axis of the ratchet device when undeformed, and contract toward the axial center of the ratchet device when deformed.

According to another embodiment of the present invention, there is provided a method of distracting a superior vertebra from an inferior vertebra comprising a) providing the distraction system according to the present invention, b) creating a chamber between the superior vertebra and the inferior vertebra, c) placing the distraction system in the chamber, thereby distracting the superior vertebra from an inferior vertebra. In one embodiment, placing the distraction system is performed bilaterally. In another embodiment, placing the distraction system comprises placing the distraction system through a channel created through the pedicle of the superior vertebra. In another embodiment, placing the distraction system comprises placing the distraction system through a sheath or hypotube, within a channel created through the pedicle of the superior vertebra.

According to another embodiment of the present invention, there is provided a method for treating diseases and conditions that change the spacial relationship between a first vertebral body of a first vertebra, a second vertebral body of a second vertebra adjacent the first vertebra, and a first intervertebral disk between the first vertebral body and the second vertebral body, or that cause instability of the vertebral column, or both, and a method that allows the surgeon to access the first intervertebral disk to restore a more normal three-dimensional configuration of the first intervertebral disk between the first vertebral body and the second vertebral body, the method comprising a) selecting a patient, b) obtaining transpedicular access to the first intervertebral disk by creating a channel through a pedicle of the first vertebra, and c) removing at least part of the first intervertebral disk through the transpedicular access. In one embodiment, the patient selected has one or more than one change in the spacial relationship between the first vertebral body of the first vertebra, the second vertebral body of the second vertebra adjacent the first vertebral body, and the first intervertebral disk between the first vertebral body and the second vertebral body, and the change in the spacial relationship causes one or more than one symptom selected from the group consisting of pain, numbness and loss of function, or where the change in the spacial relationship causes real or potential instability, or a combination of the preceding. In another embodiment, the patient has one or more than one disease or condition selected from the group consisting of degeneration of the first intervertebral disk, herniation of the first intervertebral disk, degeneration and herniation of the first intervertebral disk, degenerative scoliosis, an infection of the first intervertebral disk, an infection of the first vertebral body, an infection of the second vertebral body, a space occupying lesions, spinal stenosis, spondylosis, spondylolisthesis, vertebral instability, a vertebral fracture, and a surgical manipulation of the vertebral column. In another embodiment, obtaining transpedicular access to the first intervertebral disk is accomplished bilaterally. In another embodiment, obtaining transpedicular access to the first intervertebral disk comprises inserting a bone biopsy needle through one pedicle of the first vertebra to create the channel. In another embodiment, obtaining transpedicular access to the first intervertebral disk comprises inserting a non-flexible bone drill through one pedicle of the first vertebra to create or enlarge the channel. In another embodiment, the method further comprises inserting a sheath into the channel. In another embodiment, the method further comprises inserting a retainer tube into the channel. In another embodiment, the method further comprises inserting a first flexible drill through the channel and actuating the flexible drill, thereby extending the channel through the first vertebral body and into the intervertebral disk. In another embodiment, the first flexible drill is a flexible drill according to the present invention. In one embodiment, the method further comprises inserting a second flexible drill through the channel and actuating the flexible drill, thereby enlarging the channel. In another embodiment, the second flexible drill is a flexible drill according to the present invention. In another embodiment, the method further comprises inserting a guidewire into the channel for use as a support structure. In another embodiment, the method further comprises performing at least part of the method using an over-the-wire technique. In another embodiment, the method further comprises removing at least part of the first intervertebral disk using a cutting device. In one embodiment, the cutting device is a cutting device according to the present invention. In another embodiment, the method further comprises removing at least part of the first intervertebral disk using an enucleation device. In one embodiment, the enucleation device is an enucleation device according to the present invention. In one embodiment, the method further comprises removing at least part of an endplate of the first vertebral body or an endplate of the second vertebral body. In one embodiment, the method further comprises inserting a fusion agent containment device into the intervertebral disk, and at least partly filling the fusion agent containment device with a fusion agent. In one embodiment, the fusion agent containment device is a fusion agent containment device according to the present invention. In another embodiment, the method further comprises inserting a distraction system into the intervertebral disk, and allowing the distraction system to distract the first vertebral body from the second vertebral body. In one embodiment, the distraction system is a distraction system according to the present invention. In one embodiment, the method further comprises fusing the first vertebra to the second vertebra through the transpedicular access. In another embodiment, there is provided a method of fusing a first vertebra to a second vertebra comprising a) performing a method of the present invention, b) fusing the first vertebra to the second vertebra through the transpedicular access, and c) performing a second fusion procedure to fuse the first vertebra to the second vertebra. In one embodiment, the method further comprises removing, through the transpedicular access, at least part of a second intervertebral disk between the second vertebral body and a third vertebral body adjacent to the second vertebral body.

FIGURES

These and other features, aspects and advantages of the present invention will become better understood from the following description, appended claims, and accompanying figures where:

FIG. 11 is a lateral perspective view of an enucleation according to one embodiment of the present invention with the blades in the insertion position;

FIG. 12 is a lateral perspective view of the enucleation device shown in FIG. 11, with the blades in the cutting position;

FIG. 13 is an enlarged, lateral perspective view of the distal end of the enucleation device shown in FIG. 12;

FIG. 14 is an exploded, lateral perspective view of the enucleation device shown in FIG. 12;

Figure 1:
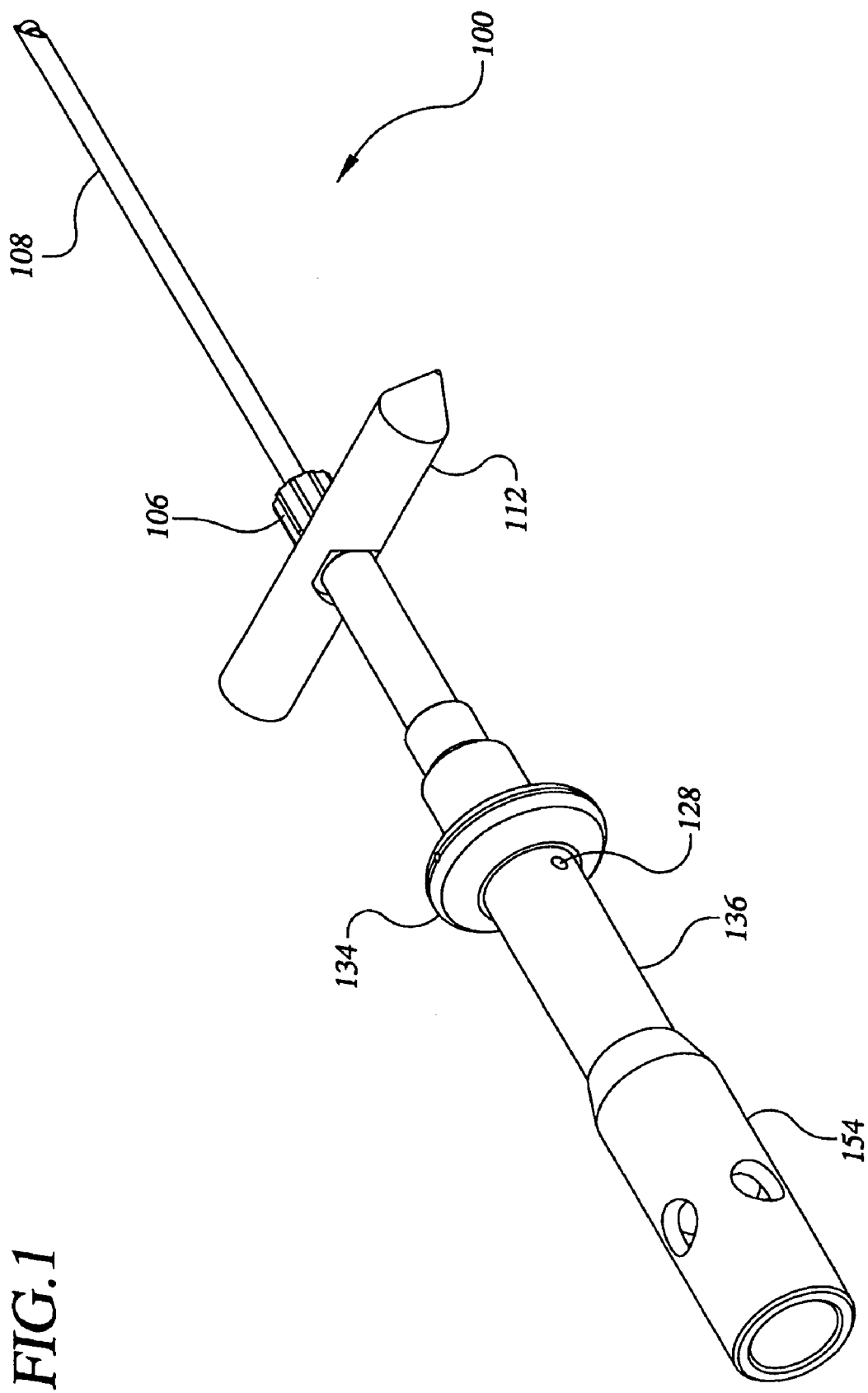
FIG. 1 is a lateral perspective view of a bone drill according to one embodiment of the present invention, with the distal drilling end in the insertion position.

FIG. 28 through FIG. 45 are partial, cutaway, lateral perspective views illustrating some aspects of the method of the present invention for treating diseases and conditions that change the spacial relationship between two vertebral bodies and the intervertebral disk, or that cause instability of the vertebral column, or both, according to the present invention; and FIG. 46 through FIG. 54 are partial, cutaway, lateral perspective views illustrating some aspects of one embodiment of the method of the present invention as performed on a first vertebral body of a first vertebra, a second vertebral body of a second vertebra, an intervertebral disk between the first vertebral body and second vertebral body, a third vertebral body of a third vertebra and an intervertebral disk between the second vertebral body and third vertebral body.

DESCRIPTION

In one embodiment of the present invention, there is provided a method for treating diseases and conditions that change the spacial relationship between the vertebral bodies and the intervertebral disks, or that cause instability of the vertebral column, or both, that is associated with less post-operative pain and a lower incidence of post-operative morbidity than traditional surgical treatments. In another embodiment, there is provided a method for treating diseases and conditions that change the spacial relationship between the vertebral bodies and the intervertebral disks, or that cause instability of the vertebral column, or both, that allows the surgeon to access the intervertebral space to restore a more normal three-dimensional configuration of the space, with or without additionally fusing two adjacent vertebrae.

In another embodiment of the present invention, there is provided a plurality of devices that can be used with the methods of the present invention for treating diseases and conditions that change the spacial relationship between the vertebral bodies and the intervertebral disks, or that cause instability of the vertebral column, or both, that allows the surgeon to access the intervertebral space to restore a more normal three-dimensional configuration of the space, with or without additionally fusing two adjacent vertebrae, or that can be used for other purposes. The devices and method of the present invention will now be disclosed in detail.

As used in this disclosure, the term "intervertebral disk" comprises both a normal intact intervertebral disk, as well as a partial, diseased, injured or damaged intervertebral disk, a disk that has been partly macerated and empty space surrounded by the remnants of a normal intervertebral disk.

As used in this disclosure, the term "substantially straight passage" means a channel in a material where the channel has a central long axis varying less than 10° from beginning to end.

As used in this disclosure, the term "curved passage" means a channel in a material where the channel has a central long axis varying more than 10° from beginning to end.

As used in this disclosure, the term "comprise" and variations of the term, such as "comprising" and "comprises," are not intended to exclude other additives, components, integers or steps.

All dimensions specified in this disclosure are by way of example only and are not intended to be limiting. Further, the proportions shown in these Figures are not necessarily to scale. As will be understood by those with skill in the art with reference to this disclosure, the actual dimensions of any device or part of a device disclosed in this disclosure will be determined by intended use.

In one embodiment, the present invention is a flexible drill comprising a flexible drilling tip, and capable of orienting the flexible drilling tip at a predetermined position after accessing a material to be drilled through a substantially straight passage having a long axis, where the predetermined position is at least 10° off of the long axis of the substantially straight passage. The flexible drill can drill through a wide variety of materials, including bone, cartilage and intervertebral disk, but can also be used to drill through other materials, both living and nonliving, as will be understood by those with skill in the art with reference to this disclosure. Referring now to FIG. 1, FIG. 2, FIG. 3, FIG. 4, FIG. 5 and FIG. 6, there are shown respectively, a lateral perspective view of the flexible drill with the distal drilling end in the insertion position; a lateral perspective view of the flexible drill with the distal drilling end in the flexible drilling position; an exploded, lateral perspective view of the lower sub-assembly of the flexible drill; an exploded, lateral perspective view of the upper sub-assembly of the flexible drill; lateral perspective views of several individual components of the flexible drill; and a lateral perspective view of an optional guiding tip that can be used with the bone drill.

Figure 2:
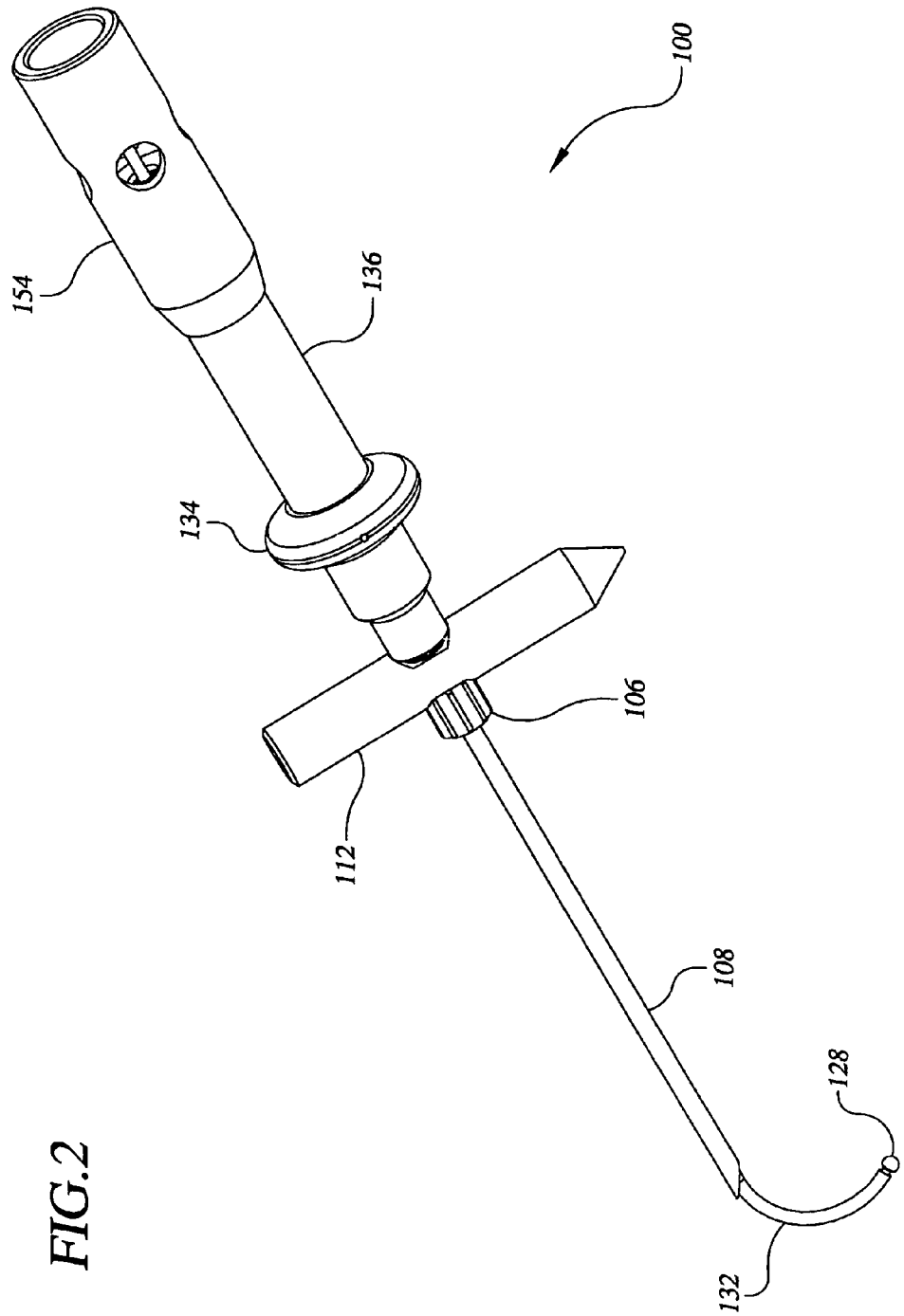
FIG. 2 is a lateral perspective view of the bone drill shown in FIG. 1, with the distal drilling end in the drilling position.
Figure 3:
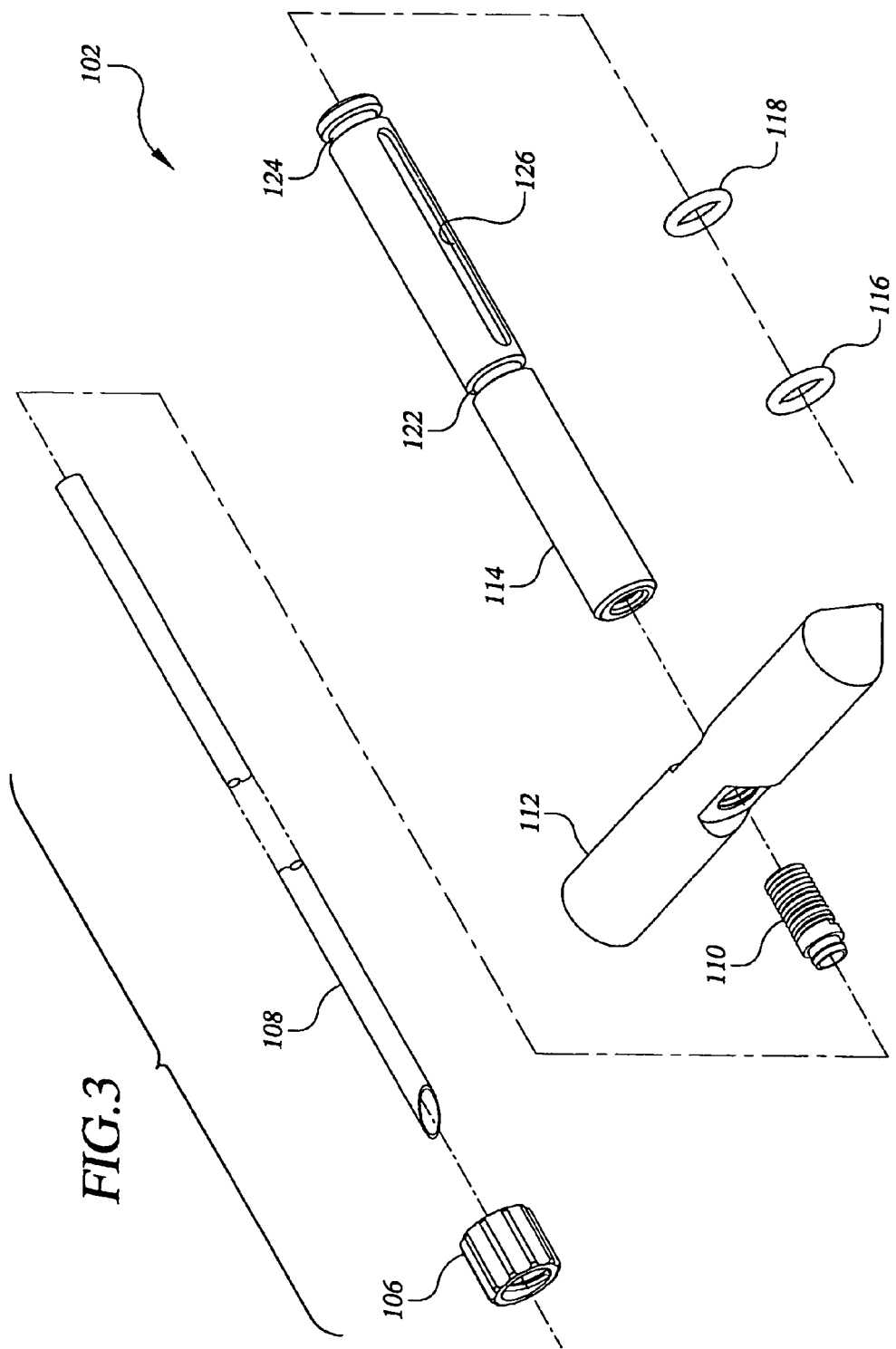
FIG. 3 is an exploded, lateral perspective view of the lower sub-assembly of the bone drill as shown in FIG. 1.

As can be seen, the flexible drill 100 comprises a lower sub-assembly 102 and an upper sub-assembly 104. Referring now to FIG. 1, FIG. 2 and, particularly to FIG. 3 and FIG. 5, the lower sub-assembly 102 comprises seven components, distally to proximally, as follows: a spin luer lock 106, a retainer tube 108, a piston anchor 110, a piston level 112, a piston 114, a distal O-ring 116 and a proximal O-ring 118. The spin luer lock 106 comprises molded nylon or an equivalent material, and is used to lock the flexible drill 100 to a sheath lining a passage where the flexible drill is to be inserted, and thereby, assists in maintaining stability of the flexible drill 100 during operation. The retainer tube 108 comprises stainless steel or an equivalent material, is preferably between about 125 mm and 150 mm in axially length, and preferably has an inner diameter of between about 4 and 4.5 mm. The piston anchor 110 comprises stainless steel or an equivalent material, and preferably, has a barb at the distal end (not shown) to snap fit over the spin luer lock 106. The piston level 112 comprises machined nylon or an equivalent material, and preferably, has a direction indicator 120 at one end, as shown. The piston 114 comprises machined nylon or an equivalent material, has a distal groove 120 and a proximal grove 124 for mating with the distal O-ring 116 and the proximal O-ring 118, respectively, and has a slot 126 for mating with a set screw (not shown) passing through a hole 128 in the barrel 136. The slot 126 and corresponding set screw allow precise positioning of the flexible drill 100 in the material to be drilled and also limit the extent of retraction of the flexible drilling tip so that the flexible drilling tip enters the retainer tube 108. In another embodiment, the slot 126 is formed as an oval opening in the retainer tube 108 and the key is formed from a corresponding oval block in the guiding tube having a smaller inner circumference. Preferably, the piston 114 has an inner diameter between about 6 mm and about 13 mm. The distal O-ring 116 and the proximal O-ring 118 comprise silicone or an equivalent material, and allow the barrel 136 and piston 114 to move axially relative to one another.

Figure 4:
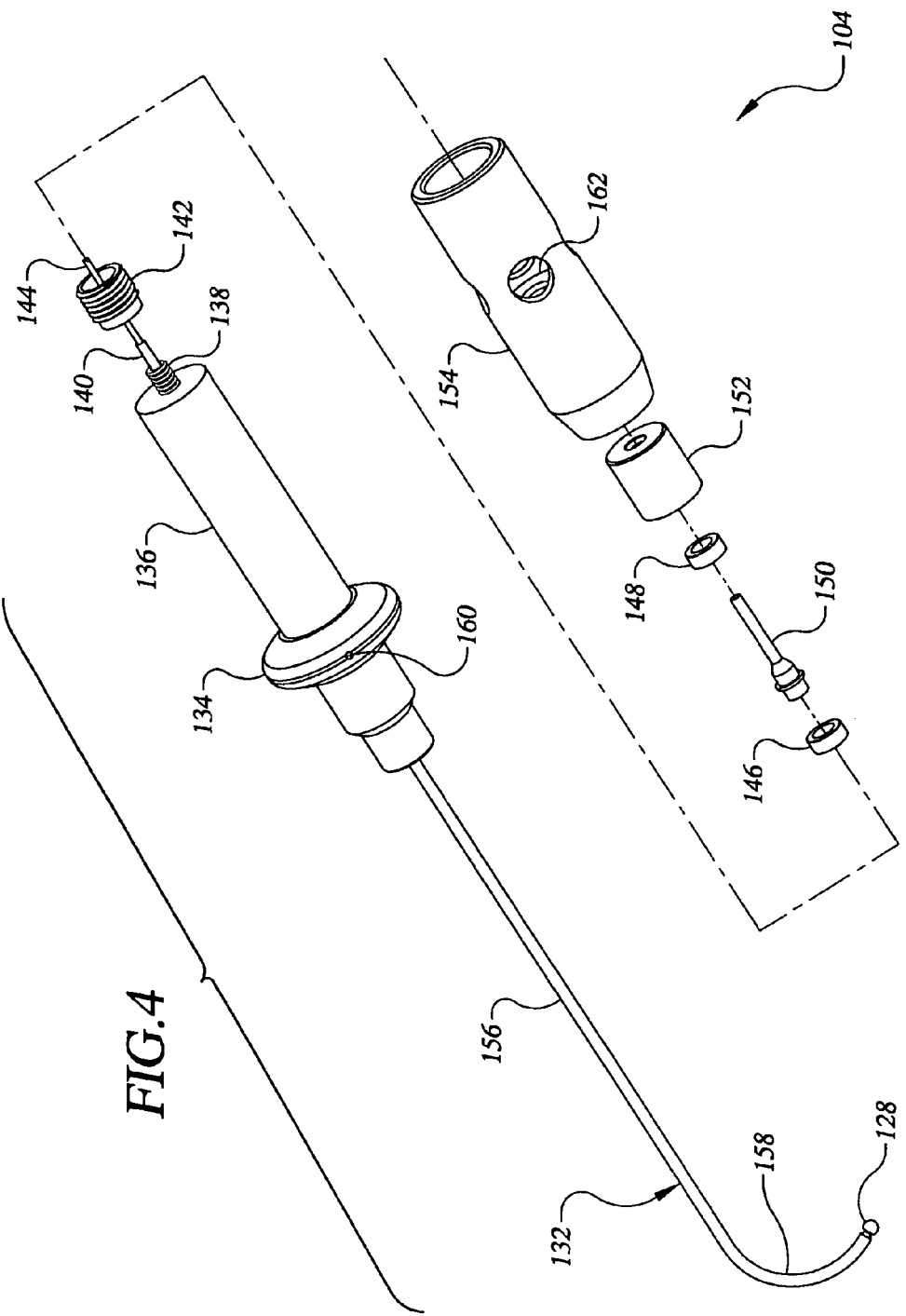
FIG. 4 is an exploded, lateral perspective view of the upper sub-assembly of the bone drill as shown in FIG. 1.
Figure 5:
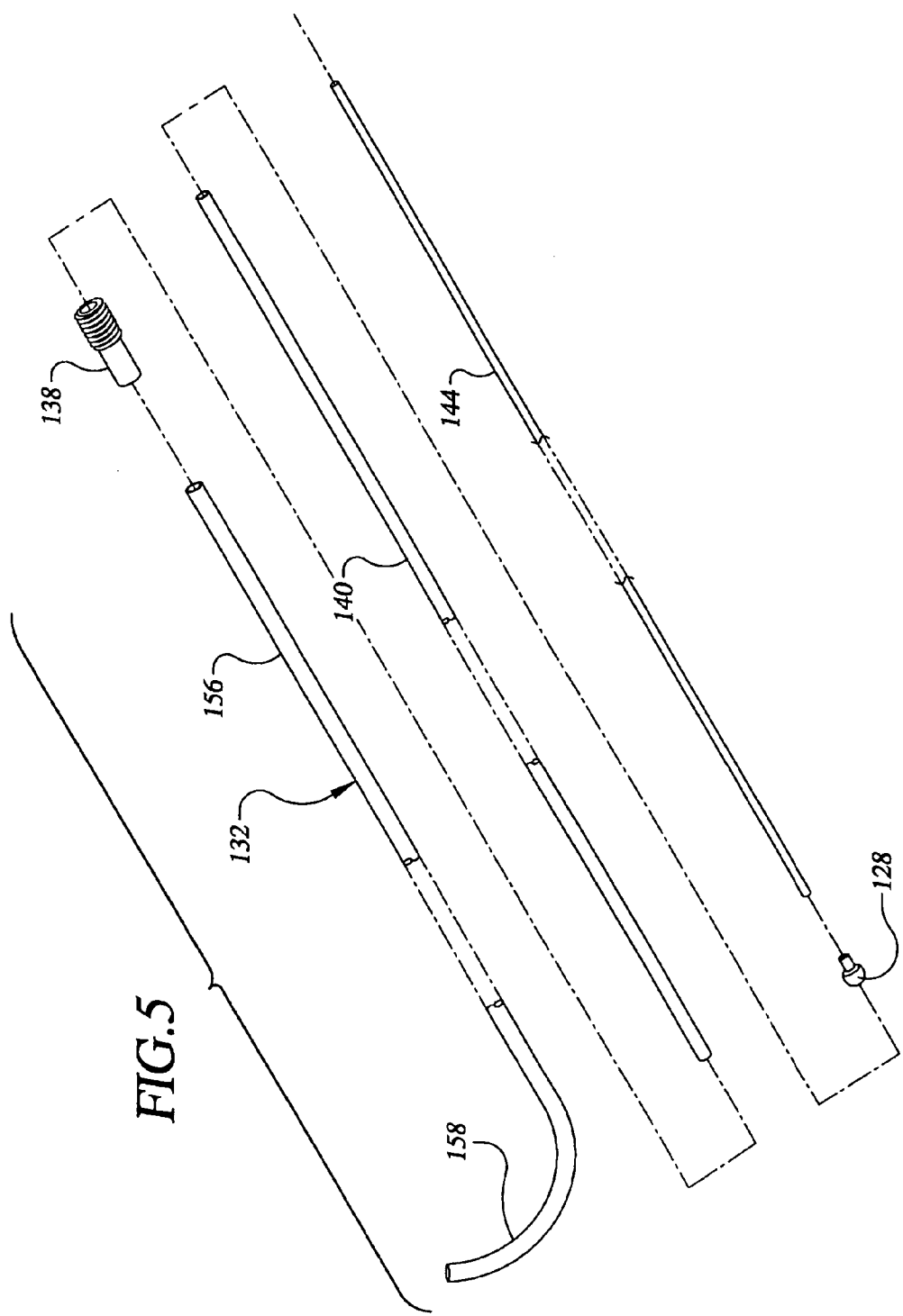
FIG. 5 is a lateral perspective views of several individual components of the bone drill as shown in FIG. 1.

Referring now to FIG. 1, FIG. 2 and, particularly to FIG. 4 and FIG. 5, the upper sub-assembly 104 comprises thirteen components, distally to proximally, as follows: a flexible drilling tip 130, a guiding tube 132, a barrel knob 134, a barrel 136, a threaded adapter 138, a liner 140, a bearing housing 142, a flexible shaft 144, a distal bearing 146, a proximal bearing 148, a collet 150, a bearing cap 152 and a motor receptacle 154. The flexible drilling tip 130 comprises stainless steel or an equivalent material, is preferably between about 3 mm and 5 mm in maximum lateral diameter. The flexible drilling tip 130 comprises a hardened burr and a shaft, such as available from Artco, Whittier, Calif. US, or a custom-made equivalent burr in stainless steel. The shaft is cut to an appropriate size by grinding down the proximal end. The dimensions of the flexible drilling tip 130 will vary with the intended use as will be understood by those with skill in the art with reference to this disclosure. By example only, in a preferred embodiment, the burr is between about 2.5 mm and 3 mm in axial length, and the shaft is between about 2.5 mm and 4 mm in length.

The guiding tube 132 has a proximal segment 156 and a distal segment 158, and comprises a substance, such as shaped metal alloy, for example nitinol, that has been processed to return to a shape where the distal segment 158 has a radius of curvature sufficient to cause the flexible drilling tip 130 at the end of the distal segment 158 to orient at between about 10° and 150° off of the central axis of the proximal segment when the guiding tube 132 is not subject to distortion. Preferably, the guiding tube 132 has an outer diameter of between about 2 mm and 4 mm. The dimensions of the guiding tube 132 are determined by the intended application of the flexible drill 100. By way of example only, the guide tube has the following dimensions. In a preferred embodiment, the outer diameter of the guiding tube 132 is less than about 2.8 mm. In a particularly preferred embodiment, the inner diameter of the guiding tube 132 is greater than about 1.6 mm. In a preferred embodiment, length of the guiding tube 132 is at least about 200 and 250 mm. In a preferred embodiment, the straight proximal segment is between about 150 mm and 200 mm. In a preferred embodiment, the distal segment 158 is between about 40 mm and 60 mm. In a preferred embodiment, the radius of curvature of the distal segment 158, without distortion, is between about 10 mm and 40 mm. In a particularly preferred embodiment, the radius of curvature of the distal segment 158, without distortion, is about 25 mm.

The barrel knob 134 comprises machined nylon or an equivalent material, and has a hole 160 to mate with a dowel pin (not shown). Advancing and retracting the barrel knob 134 with respect to the piston level 112 causes the flexible drilling tip 130 to advance and retract in the material being drilled. Once drilling is completed, actuation of the flexible drill 100 is stopped, the barrel knob 134 is retracted with respect to the piston level 112 causing the flexible drilling tip 130 to retract into the retainer tube 108, and the flexible drill 100 is removed from the substantially straight passage.

The barrel 136 comprises machined nylon or an equivalent material, and preferably, has an outer diameter of between about 12 mm and 18 mm, and an axial length of between about 75 mm and 125 mm. The threaded adapter 138 comprises stainless steel, or an equivalent material, and is used to attach the barrel 136 to the guiding tube 132. The liner 140 comprises polytetrafluoroethylene (such as TEFLON®) or an equivalent material. The liner 140 is placed between the flexible shaft 144 and the guiding tube 132, and thus, has an outer diameter smaller than the inner diameter of the guiding tube 132, and an inner diameter larger than the outer diameter of the flexible shaft 144. In a preferred embodiment, by way of example only, the outer diameter of the liner 140 is between about 0.075 mm and 0.125 mm less than the inner diameter of the guiding tube 132. The liner 140 is between about 25 mm and 40 mm shorter than the guiding tube 132.

The bearing housing 142 comprises machined nylon or an equivalent material, is configured to house the distal bearing 146, and has a fine interior circumferential thread to mate with the threaded adapter 138, thereby allowing an operator to adjust the tension of the flexible shaft 144.

The flexible shaft 144 comprises a flexible, solid tubular structure. The flexible shaft 144 comprises stainless steel wire or an equivalent material, and has an outer diameter smaller than the inner diameter of the liner 140. By example only, in a preferred embodiment, the flexible shaft 144 comprises 7 bundles of wire with 19 strands of 0.066 mm wire per bundle. Also by example only, in another preferred embodiment, the flexible shaft 144 comprises four layers of closely braided wire having a diameter of between about 0.05 mm and 0.06 mm over a single core wire of not more than about 0.25 mm in diameter. The first layer comprises a single wire, the second layer comprises two wires, the third layer comprises three wires and the fourth layer comprises four wires. Also by example only, in a preferred embodiment, the cable comprises two layers of wire coaxial and reversibly wound to a single core wire, available as part number FS 045N042C from PAK Mfg., Inc., Irvington, N.J. US. The ends of the wire are soldered or welded to prevent unraveling. The flexible shaft 144 has an outer diameter of between about 1 mm and about 2.3 mm smaller than the inner diameter of the liner 140. The flexible shaft 144 has an axial length of about 250 mm to 300 mm.

The distal bearing 146 and the proximal bearing 148 comprise stainless steel or an equivalent material. The collet 150 comprises machined stainless steel or an equivalent material. The bearing cap 152 comprises machined nylon or an equivalent material, and is configured to house the proximal bearing 148. The motor receptacle 154 comprises machined nylon or an equivalent material, and has an outer diameter of between about 25 mm and 30. The motor receptacle 154 allows a motor to be easily mated with the flexible drill 100. Preferably, the motor receptacle 154 has four windows 162, as shown, to ensure the chuck of the motor (not shown) driving the flexible drill 100 is engaged with the collet 150.

Figure 6:
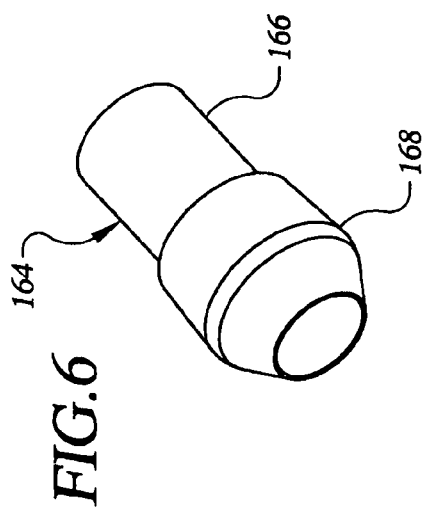
FIG. 6 is a lateral perspective view of an optional guiding tip that can be used with the bone drill as shown in FIG. 1.

Referring now to FIG. 6, in another embodiment, the upper sub-assembly 104 of the flexible drill 100 further comprises a guiding tip 164 attached to the guiding tube 132, such as by soldering, just proximal to the flexible drilling tip 130. The guiding tip 164 comprises a proximal tubular section 166 and a distal flared section 168. The guiding tip 164, when present, assists translating the flexible drilling tip 130 forward during drilling. The guiding tip 164 comprises a hard, biocompatible material, such as by way of example only, hardened stainless steel. The dimensions of the guiding tip 164 will vary with the intended use as will be understood by those with skill in the art with reference to this disclosure. By example only, in a preferred embodiment, the proximal tubular section 166 is between about 3.5 mm and 4 mm in axial length, and the distal flared section 168 is between about 2.4 mm and 2.6 mm in axial length. The distal flared section 168 has a maximal sagittal length of between about 2.5 mm and 2.7 mm.

In another embodiment, the flexible drill 100 is configured to be used in an over-the-wire technique. In this embodiment, the flexible shaft 144 comprises a flexible, hollow tubular structure (not shown), that is, has an axial channel for accepting a guide wire, instead of the flexible, solid tubular structure used in the none over-the-wire embodiment. The flexible, hollow tubular structure generally comprises the same elements as the flexible, solid tubular structure disclosed above, except however, for the axial channel. In one embodiment, the flexible, hollow tubular structure has an axial channel having a diameter of between about 0.5 mm and 1.0 mm, and has an outer diameter slightly larger than the outer diameter of the flexible shaft 144 that is a flexible, solid tubular structure, such as by way of example only, an outer diameter of about 2.0 mm. In one embodiment, the flexible, hollow tubular structure, comprises two layers of 0.3 mm to 0.5 mm diameter wire that are coiled in opposite directions with the outer layer wound counterclockwise (available from PAK Mfg., Inc.). When the flexible shaft 144 is configured for over-the-wire use, the outer diameters of the retainer tube 108, guiding tube 132 and liner 140 are increased proportionally to the increase in the outer diameter of the flexible shaft 144, and the flexible drilling tip 130 (and guiding tip 164, if present) also has a corresponding axial channel to allow passage of the guidewire.

The flexible drill 100 can be assembled in any suitable manner, as will be understood by those with skill in the art with reference to this disclosure. In a preferred embodiment, the flexible drill 100 is assembled as follows. First, the retainer tube 108 is soldered to the piston anchor 110. Then, the piston level 112 is threaded over the piston anchor 110 and rotated until the piston level 112 stops. Using the direction indicator 120 as reference, the retainer tube 108 is cut to length and the distal end of the retainer tube 108 is cut to form a bevel having a cut angle of between about 20° and 45° degrees with the cutting plane and oriented in the same direction as the direction indicator 120. Next, the piston 114 is threaded over the piston anchor 110 until the piston 114 stops. Then, the distal O-ring 116 and the proximal O-ring 118 are positioned over the distal groove 120 and the proximal groove 124, respectively, in the piston 114. Next, the guiding tube 132 is soldered to the threaded adapter 138, and the barrel 136 is loosely threaded over the proximal end of the threaded adapter 138. Then, the barrel knob 134 is press fitted over the barrel 136 and secured by a dowel pin (not shown) inserted into the hole 160 in the barrel knob 134. Next, the bearing housing 142 is threaded over the threaded adapter 138 until the bearing housing 142 stops. Then, the distal segment 158 of the guiding tube 132 is temporarily straightened and the proximal end of the proximal segment 156 of the guiding tube 132 is inserted into the piston 114 and retainer tube 108. Next, the distal end of the barrel 136 is slid over the proximal end of the piston 114. Then, the hole 160 in the barrel knob 134 for the set screw is aligned with the slot 126 in the piston 114, and a set screw (not shown) is screwed into the hole and slot 126.

Next, the distal segment 158 of the guiding tube 132 is aligned with the cutting plane of the retainer tube 108 by rotating the threaded adapter 138, and the threaded adapter 138 is secured to the barrel 136. Then, the flexible drilling tip 130 is soldered to the flexible shaft 144. Next, the liner 140 is slid over the flexible shaft 144. Then, the barrel knob 134 and piston level 112 are distracted from each other, thereby straightening the distal segment 158 of the guiding tube 132 inside the retainer tube 108, and the liner 140 with the flexible shaft 144 is slid into the distal end of the guiding tube 132. Next, the distal bearing 146 is placed into the bearing housing 142 through the flexible shaft 144. Then, the collet 150 is slid over the flexible shaft 144 and attached to the flexible shaft 144, such as by crimping or soldering. Next, the proximal bearing 148 is slid over the collet 150, and the bearing cap 152 is placed over the bearing and secured to the bearing housing 142. Then, the motor receptacle 154 is press fitted to the barrel 136 until the motor receptacle 154 stops. Finally, the spin luer lock 106 is snap fit onto the piston anchor 110. In one embodiment, a thin-walled hypodermic tube, not shown, is slid and crimped over the proximal portion of the flexible shaft 144 to increase the transmission of torque from the motor.

In one embodiment, the present invention is a method of using a flexible drill comprising a flexible drilling tip, and having the ability to orient the flexible drilling tip at a predetermined position after accessing a material to be drilled through a substantially straight passage, where the predetermined position is at least 10° off of the long axis of the substantially straight passage, or is between about 10° and 150° off of the long axis of the substantially straight passage. In a preferred embodiment, the predetermined position is at least about 90° off of the long axis of the substantially straight passage. In another preferred embodiment, the predetermined position is between about 90° and 120° off of the long axis of the substantially straight passage.

In one embodiment, the method comprises drilling a substantially straight passage through a first material. Then, a flexible drill is provided where the flexible drill comprises a flexible drilling tip, where the flexible drill has the ability to orient the flexible drilling tip at a predetermined position after accessing a material to be drilled through a substantially straight passage, and where the predetermined position is at least 10° off of the long axis of the substantially straight passage. Next, the flexible drill is inserted into the substantially straight passage and advanced through the substantially straight passage and the flexible drilling tip is advanced until the flexible drilling tip exits the substantially straight passage into a second material, thereby allowing the flexible drilling tip to orient to the predetermined position within the second material. Then, the flexible drill is actuated, thereby drilling into the second material. Next, actuation of the flexible drill is stopped, thereby stopping the flexible drilling into the second material. Then, the flexible drill is removed through the substantially straight passage.

In a preferred embodiment, the flexible drill provided is a flexible drill according to the present invention. In another preferred embodiment, the space is an intervertebral disk space between a first vertebra and a second vertebra. In another preferred embodiment, the first material is pedicle bone of either the first vertebra or the second vertebra. In another preferred embodiment, the first material is pedicle bone of either the first vertebra or the second vertebra, and the second material is intervertebral disk between the first vertebra and the second vertebra.

In another embodiment, the present invention is a method for removing intervertebral disk between a first vertebra and a second vertebra. The method comprises drilling a substantially straight passage through a pedicle of either the first vertebra or the second vertebra. Then, a flexible drill is provided where the flexible drill comprises a flexible drilling tip, where the flexible drill has the ability to orient the flexible drilling tip at a predetermined position within the intervertebral disk space after accessing the intervertebral disk space through a substantially straight passage through a pedicle, and where the predetermined position is at least 10° off of the long axis of the substantially straight passage. Next, the flexible drill is inserted into the substantially straight passage in the pedicle and advanced through the substantially straight passage. Then, the flexible drilling tip is advanced until the flexible drilling tip exits the substantially straight passage into the intervertebral disk, thereby allowing the flexible drilling tip to orient to the predetermined position within the intervertebral disk. Next, the flexible drill is actuated, thereby drilling into the intervertebral disk. Then, actuation of the flexible drill is stopped, thereby stopping the flexible drilling into the intervertebral disk. Next, the flexible drill is removed through the substantially straight passage.

In a preferred embodiment, the flexible drill provided is a flexible drill according to the present invention. In another preferred embodiment, the method further comprises inserting a sheath, such as for example only, a stainless steel sheath, with an inner diameter less than about 5 mm and tapered at the distal end into the substantially straight passage before inserting the flexible drill, then inserting the flexible drill through the sheath. In a preferred embodiment, the sheath is a luer lock at the proximal end to mate with drill after inserting the flexible drill. In a preferred embodiment, the flexible drill has a direction indicator and the flexible drilling tip is oriented within the intervertebral disk using the direction indicator.

In one embodiment, the method comprises using an over-the-wire technique. In this embodiment, a guide wire is place in the flexible shaft and drilling tip and, upon removal of the flexible drill from the substantially straight passage, the guide wire is left in place to allow passage of the next device into the substantially straight passage and into the space that has been drilled.

In another embodiment, the present invention is a cutting device comprising a pivoting blade connected to the distal end of a flexible shaft, where the cutting device can be inserted into a material to be cut after accessing the material through a channel having a substantially straight proximal section having a long axis and a distal section having a long axis, where the long axis of the distal section is curved, or where the long axis of the distal section varies at least about 10° off of the long axis of the proximal section. The cutting device can cut through a wide variety of materials, including bone, cartilage and intervertebral disk, but can also be used to drill through other materials, both living and nonliving, as will be understood by those with skill in the art with reference to this disclosure. Referring now to FIG. 7, FIG. 8, FIG. 9 and FIG. 10, there are shown, respectively, a lateral perspective view of the cutting device with the distal end in the cutting position; a cutaway, lateral perspective view of the cutting device with the distal end in the insertion position; a close-up, partial, cutaway, lateral perspective view of the distal end of the cutting device with the distal end in the insertion position; and a close-up, partial, cutaway, lateral perspective view of the distal end of the cutting device with the distal end in the cutting position.

Figure 7:
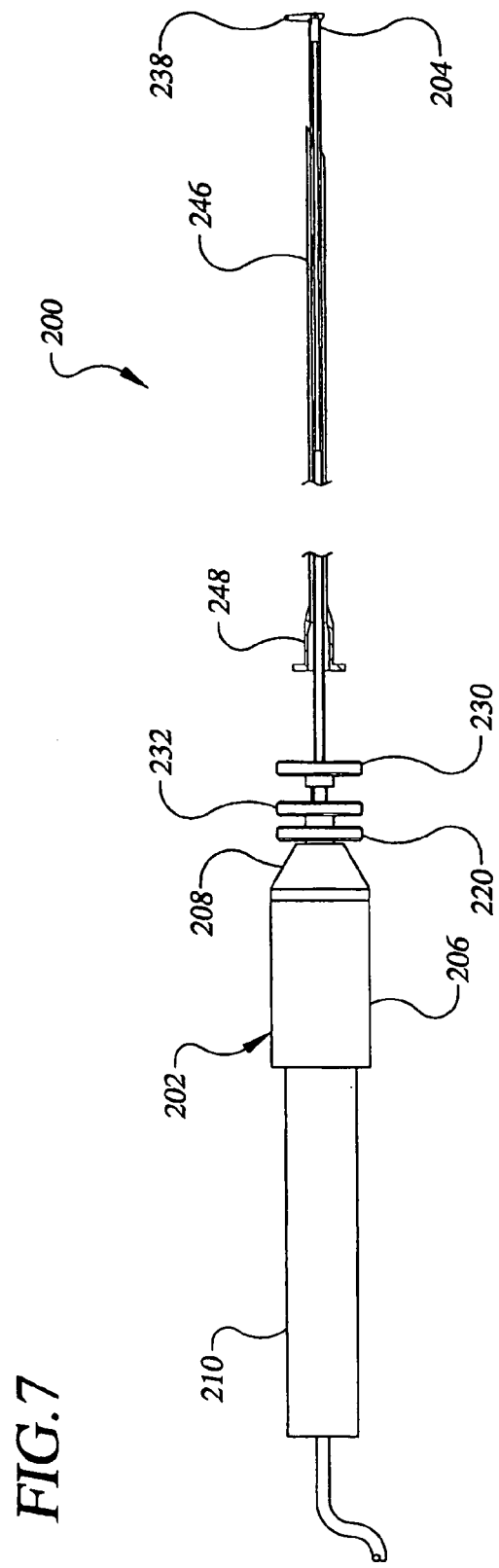
FIG. 7 is a lateral perspective view of a cutting device according to one embodiment of the present invention with the distal end in the cutting position.
Figure 8:
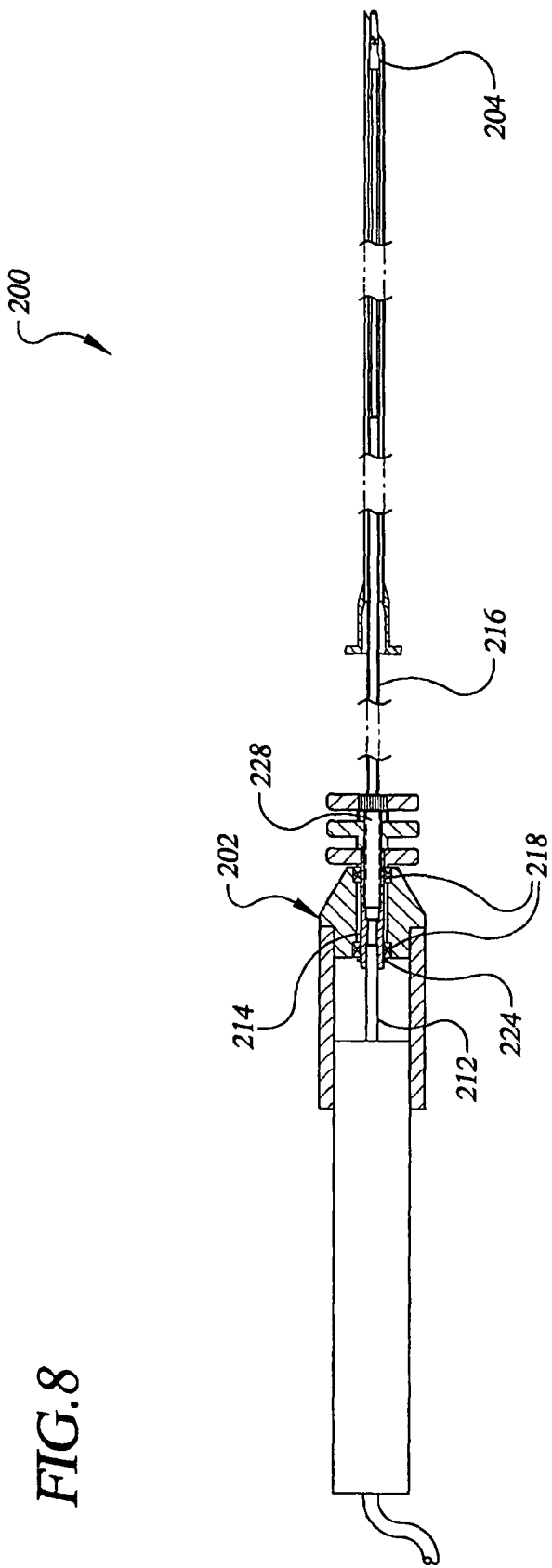
FIG. 8 is a cutaway, lateral perspective view of the cutting device shown in FIG. 7 with the distal end in the insertion position.

As can be seen in FIG. 7 and FIG. 8, the cutting device 200 comprises a proximal end 202 and a distal end 204. The proximal end 202 comprises a motor adapter 206 connected distally to a bearing housing 208, such as for example only, by press fitting. The motor adapter 206 is used to connect the cutting device 200 to a motor drive 210, partially shown in FIG. 7 and FIG. 8, capable of transmitting axial rotation to the distal end 204 of the cutting device 200 to function as disclosed in this disclosure. Both the motor adapter 206 and the bearing housing 208 can comprise any suitable material capable of being machined or molded into the proper shape, and having suitable properties, as will be understood by those with skill in the art with reference to this disclosure. In a preferred embodiment, both of the motor adapter 206 and the bearing housing 208 comprise a polymer. In a particularly preferred embodiment, both the motor adapter 206 and the bearing housing 208 comprise DELRIN® (E. I. du Pont De Nemours and Company Corporation, Wilmington, Del. US). The motor drive 210 used with the cutting device 200 of the present invention can be any suitable motor drive 210. In a preferred embodiment, the motor drive 210 is a variable speed motor drive. In one embodiment, by way of example only, the motor drive 210 is an NSK Electer EMAX motor drive (NSK Nakanishi Inc., Tochigi-ken, Japan).

Referring now to FIG. 8, the cutting device 200 further comprises an adapter tube 212, having a proximal end configured to mate with the housing of the motor drive 210 and having a distal end fitted and fixed, such as by soldering, into the proximal end of a drive shaft 214. The adapter tube 212 transmits torque from motor drive 210 to the distal end 204 of the cutting device 200. The adapter tube 212 can comprise any suitable material for the purpose disclosed in this disclosure. In one embodiment, the adapter tube 212 comprises stainless steel. In another embodiment, the adapter tube 212 has an inner diameter of about 1.9 mm and 2 mm, and an outer diameter of about 2.4 mm. In another embodiment, the adapter tube 212 is about 25 mm in axial length. In one embodiment, by way of example only, the adapter tube 212 is part number 13tw, from Micro Group Inc., Medway, Mass. US, ground to appropriate dimensions.

Referring now to FIG. 7 and FIG. 8, the cutting device 200 further comprises a drive tube 216 having a proximal end fitted and fixed, such as by silver soldering, into the distal end of the adapter tube 212 and extending distally toward the distal end 204 of the cutting device 200. The drive tube 216 provides rigidity to the cutting device 200 allowing advancement and retraction of the cutting device 200 and transmits torque from motor drive 210 to the distal end 204 of the cutting device 200. In one embodiment, the drive tube 216 comprises stainless steel. In another embodiment, the drive tube 216 has an axial length of about 200 mm. In another embodiment, the drive tube 216 has an inner diameter of about 1.3 mm and an outer diameter of about 1.8 mm. In a preferred embodiment, by way of example only, the drive tube 216 is part number 15H, Micro Group Inc.

Referring now to FIG. 8, the cutting device 200 further comprises two bearings 218 pressed into the bearing housing 208, and comprises a drive shaft 214 within the bearing housing 208 and supported between the bearings 218. The bearings 218 and drive shaft 214 assist in translating torque from motor drive 210 to the distal end 204 of the cutting device 200 to create smooth axial rotation of the distal end 204 of the cutting device 200. The bearings 218 can comprise any suitable bearings, as will be understood by those with skill in the art with reference to this disclosure. In one embodiment, the bearings 218 are miniature, high speed stainless steel radial bearings, such as part number 57155k53, McMaster-Carr Supply Co., Sante Fe Springs, Calif. US). The drive shaft 214 is an interface between the bearings 218 and the drive tube 216 and provides smooth rotation for the distal end 204 of the cutting device 200. In a preferred embodiment, the drive shaft 214 has a 6-32 female thread that is about 16 mm deep on distal end 204, and has a retaining ring groove and a 1.9 mm diameter hole drilled through the long axis on the proximal end. The drive shaft 214 is counter bored between about 2.3 mm and 2.4 mm in diameter and about 5 mm deep on the proximal end. The drive shaft 214 can be any suitable material, as will be understood by those with skill in the art with reference to this disclosure. In one embodiment, the drive shaft 214 is machined stainless steel.

Referring now to FIG. 7 and FIG. 8, the cutting device 200 further comprises a collar 220 press fitted onto the distal end of the drive shaft 214 until the collar 220 is flush with the distal end of the drive shaft 214. An operator can prevent rotation of the drive shaft 214 during advancement and actuation of the distal end of the cutting device 200 by grasping the collar 220 to prevent rotation of the collar 220, and hence, the drive shaft 214. The collar 220 can comprise any suitable material capable of being machined or molded into the proper shape, and having suitable properties, as will be understood by those with skill in the art with reference to this disclosure. In one embodiment, the collar 220 comprises a polymer, such as for example only, DELRIN®.

Figure 10:
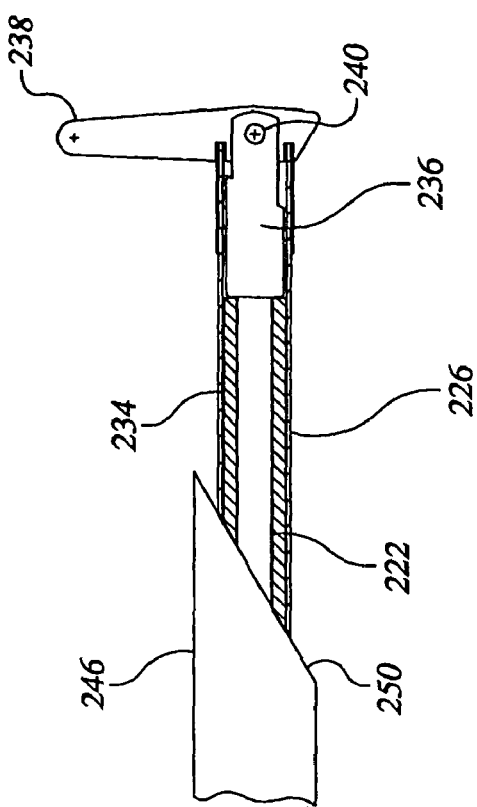
FIG. 10 is a close-up, partial, cutaway, lateral perspective view of the distal end of the cutting device shown in FIG. 7.

Referring now to FIG. 7, FIG. 8 and particularly FIG. 10, the cutting device 200 further comprises a flexible shaft 222 having a proximal end extending through the drive tube 216, and fitted and fixed, such as by soldering, flush into the distal end of the adapter tube 212. Additionally, the distal end of the drive tube 216 is fixed to the flexible shaft 222, such as by crimping or silver soldering. In one embodiment, the flexible shaft 222 comprises constructing from a multi-filar winding with a solid core. In another embodiment, the flexible shaft 222 has an axial length of about 300 mm. In another embodiment, the flexible shaft 222 has a diameter of about 1.25 mm. In a preferred embodiment, by way of example only, the flexible shaft 222 is part number FS045N042C, PAK Mfg., Inc., Irvington, N.J. US.

The drive shaft 214, adapter tube 212, drive tube 216 and flexible shaft 222 assembly are inserted into the bearing housing 208, held in place using a retaining ring 224, and transmit torque from motor drive 210 to the distal end of the cutting device 200. In a preferred embodiment, by way of example only, the retaining ring 224 is part number 98410A110, McMaster-Carr Industrial Supply.

Referring now to FIG. 7, FIG. 8, FIG. 9 and FIG. 10, the cutting device 200 further comprises a braided tube 226 surrounding the flexible shaft 222 throughout the length of the flexible shaft 222. The braided tube 226 increases column stiffness. In one embodiment, the braided tube 226 comprises stainless steel. In another embodiment, the braided tube 226 has an axial length of about 220 mm. In a preferred embodiment, by way of example only, the braided tube 226 can be fabricated by Viamed Corp., South Easton, Mass. US.

The proximal end of the braided tube 226 is soldered to the head of a 6-32 cap screw 228 forming a hollow joint. In one embodiment, the cap screw 228 is a 6-32×1.9 mm long socket head cap screw, such as part number 92196A151, McMaster-Carr Industrial Supply, that has been modified by drilling a 1.85 mm diameter hole through the long axis to provide a through lumen for the drive tube 216. The cap screw 228 can comprise any suitable material capable of being machined or molded into the proper shape, and having suitable properties, as will be understood by those with skill in the art with reference to this disclosure. In one embodiment, the cap screw 228 comprises stainless steel.

The cutting device 200 further comprises a thumb screw knob 230 pressed fitted flush onto the head of the cap screw 228. The thumb screw knob 230 can comprise any suitable material capable of being machined or molded into the proper shape, and having suitable properties, as will be understood by those with skill in the art with reference to this disclosure. In a preferred embodiment, the thumb screw knob 230 comprises a polymer, such as for example only, DELRIN®.

The cutting device 200 further comprises a lock nut 232 fully screwed onto the cap screw 228. The lock nut 232 and braided tube 226 are placed over the distal end of the flexible shaft 222 and drive tube 216, and the cap screw 228 is fully screwed into the drive shaft 214. The cap screw 228, thumb screw knob 230 and lock nut 232 assembly allows the operator to advance distally or retract proximally the braided tube 226, and to lock the braided tube 226 into a desired position.

Referring now to FIG. 10, the cutting device 200 further comprises a shrink tube 234 covering all of the distal end of the flexible shaft 222 and between the inner surface of the braided tube 226 and the outer surface of the flexible shaft 222. In one embodiment, the shrink tube 234 comprises Polytetrafluoroethylene (available from Zeus Industrial Products, Orangeburg, S.C. US). In another embodiment, the shrink tube 234 has an inner diameter of about 1.3 mm and an outer diameter of about 1.5 mm. In another embodiment, the shrink tube 234 is about 160 mm long.

Figure 9:
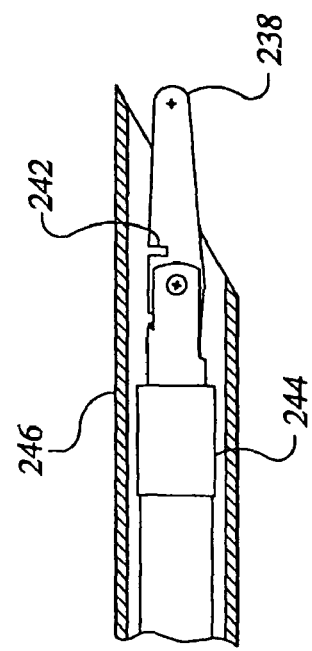
FIG. 9 is a close-up, partial, cutaway, lateral perspective view of the distal end of the cutting device shown in FIG. 7 with the distal end in the insertion position.

Referring now to FIG. 9 and FIG. 10, the distal end of the cutting device 200 further comprises a hinge 236 attached to the distal end of the flexible shaft 222, such as for example by silver soldering. The hinge 236 can comprise any suitable material capable of being machined or molded into the proper shape, and having suitable properties, as will be understood by those with skill in the art with reference to this disclosure. In one embodiment, the hinge 236 comprises stainless steel. The cutting device 200 further comprises a blade 238 attached to the distal end of the hinge 236 in a manner that allows the blade 238 to pivot to at least about 90° with respect to the long axis of the cutting device 200, such as by a dowel 240, as shown, from a first, insertion position, FIG. 9, to a second, cutting position, FIG. 10. The blade 238 has a circumferential cutting edge and one or more than one notch 242, such as the two notches shown in FIG. 9 and FIG. 10. In a preferred embodiment, as shown, the blade 238 has a rounded distal tip suitable for macerating spinal nucleus and abrading vertebral body endplates. However, other blade shapes could also be used depending on the intended use of the cutting device 200, as will be understood by those with skill in the art with reference to this disclosure. The blade 238 can comprise any suitable material capable of being machined or molded into the proper shape, and having suitable properties, as will be understood by those with skill in the art with reference to this disclosure. In one embodiment, the blade 238 comprises stainless steel.

In a preferred embodiment, the cutting device 200 further comprises a locking sleeve 244 attached to the distal end of the braided tube 226, such as by silver soldering. The locking sleeve 244 can be advanced distally and retracted proximally by manipulating the braided tube 226 using the cap screw 228, thumb screw knob 230 and lock nut 232 assembly. As shown in FIG. 9 and FIG. 10, when the locking sleeve 244 is retracted proximally, the distal end of the locking sleeve 244 disengages from the one or more than one notch 242 in the blade 238 and allows the blade 238 to pivot freely. When the locking sleeve 244 is advanced distally, the distal end of the locking sleeve 244 is configured to mate with corresponding one or more than one notch 242 in the blade 238, and serve to lock the blade 238 at 90° with respect to the long axis of the cutting device 200. The locking sleeve 244 can comprise any suitable material capable of being machined or molded into the proper shape, and having suitable properties, as will be understood by those with skill in the art with reference to this disclosure. In one embodiment, the locking sleeve 244 comprises stainless steel. In another embodiment, the locking sleeve 244 has an inner diameter of about 2.5 mm and an outer diameter of about 2.6 mm. In another embodiment, the locking sleeve 244 has a length of about 3.8 mm.

Referring now to FIG. 7, FIG. 8, FIG. 9 and FIG. 10, In a preferred embodiment, the distal end 204 of the cutting device 200 further comprises a sheath 246 movably surrounding the braided tube 226 distally and connected to a luer hub 248 proximally. The distal end of the sheath 246 has a bevel 250, as shown in the Figures. In one embodiment, the bevel makes an angle of about 30° with the long axis of the cutting device 200. In a preferred embodiment, the distal end of the cutting device 200 is advanced into and retracted from the space where drilling is required through the sheath 246. During retraction, the beveled distal end of the sheath 246 contacts the blade 238, causing the blade 238 to disengage from the locking sleeve 244 and pivot to the insertion position. The sheath 246 and luer hub 248 can comprise any suitable material capable of being machined or molded into the proper shape, and having suitable properties, as will be understood by those with skill in the art with reference to this disclosure. In one embodiment, the sheath 246 comprises a polymer such as PEBAX® (Atochem Corporation, Puteaux, FR). In another embodiment, the luer hub 248 comprises polycarbonate. In one embodiment, the sheath 246 has an inner diameter of about 2.8 mm and an outer diameter of about 3.6 mm. In another embodiment, the sheath 246 is about 150 mm long.

The cutting device 200 of the present invention can be used to create a cavity in any suitable material, including living tissue, such as bone, connective tissue or cartilage. Further, the cutting device 200 can be used to debulk a tumor. Additionally, the cutting device 200 can be used to increase the cross-sectional area of a channel by moving the cutting device 200 within the channel while the motor is actuated.

The cutting device 200 is used as follows. A channel is made in living bone or other suitable material having a circumference large enough to accommodate the distal end of the cutting device 200. Next, the sheath 246 is inserted into the channel. Then, the cutting device 200 is inserted into the sheath 246 and advanced until the distal end of the cutting device 200, including the blade 238, exits the sheath 246 distally. The preset radius of the distal end of the blade 238 causes the blade 238 to pivot when it comes into contact with any surface. Next, the braided tube 226 with attached locking sleeve 244 are advanced distally causing the locking sleeve 244 to engage the one or more than one notch 242 in the blade 238. The motor drive 210 is actuated causing the drive cable to rotate axially and, thereby rotating the cutting blade 238. Cutting can be performed by maintaining the cutting device 200 in a stationary position, or can be performed while moving the cutting device 200 proximally and distally increasing the volume of material that is cut. Once cutting is complete, the motor is deactivated, causing the drive cable to cease rotating axially, thereby stopping the cutting motion of the blade 238. The sheath 246 is advanced distally, causing the locking sleeve 244 to disengage from the blade 238 and the blade 238 to return to its insertion position. In one embodiment, the cutting device 200 is then withdrawn through the sheath 246. In another embodiment, the sheath 246 is then advanced to a second position and the steps repeated, thereby cutting at a second location. In a preferred embodiment, the debris from the cutting is removed using suction, by flushing with a suitable solution such as saline, or by a combination of suction and flushing, using techniques known to those with skill in the art.

In another embodiment, the present invention is an enucleation device comprising a plurality of deformable blades that can cut material in a space when the blades are not deformed, after accessing the space through a channel while the blades are deformed, where the channel has a smaller cross-sectional area than the cross-sectional area of the plurality of undeformed blades. Referring now to FIG. 11, FIG. 12, FIG. 13 and FIG. 14, there are shown, respectively, a lateral perspective view of the enucleation device with the blades in the insertion position; a lateral perspective view of the enucleation device with the blades in the cutting position; an enlarged, lateral perspective view of the distal end of the enucleation device; and an exploded, lateral perspective view of the enucleation device. As can be seen in the Figures, the enucleation device 300 comprises a proximal end 302 and a distal end 304. In one embodiment, the enucleation device 300 further comprises the following parts: a motor adapter 306, a chuck adapter 308, a bearing cap 310, a proximal bearing 312, a collet adapter 314, a distal bearing 316, a bearing housing 318, a threaded adapter 320, a barrel 322, a barrel knob 324, a spacer tube 326, a hypotube 328, a shaft 330, a shrink tube 332, and a cutting cap 334 comprising a plurality of blades 336. However, some of the parts, such as the chuck adapter 308 are optional, and other parts can be substituted for equivalent parts, as will be understood by those with skill in the art with reference to this disclosure. The parts of the enucleation device 300 can comprise any suitable material capable of being machined or molded into the proper shape, and having suitable properties, as will be understood by those with skill in the art with reference to this disclosure. In a preferred embodiment, the motor adapter 306, bearing cap 310, bearing housing 318, barrel 322, barrel knob 324 and spacer tube 326 comprise a polymer or an equivalent material. In a particularly preferred embodiment, they comprise DELRIN®. In another preferred embodiment, the chuck adapter 308, proximal bearing 312, collet adapter 314, distal bearing 316, threaded adapter 320, hypotube 328, and hollow shaft comprise stainless steel or an equivalent material. In another preferred embodiment, the shrink tube 332 comprises polytetrafluoroethylene (such as TEFLON®) or an equivalent material. In another preferred embodiment, the cutting cap 334 with its plurality of blades 336 comprises a shaped metal alloy, such a nitinol, that has been processed to return to an orthogonally-expanded cutting configuration suitable for cutting when undeformed. These parts will now be disclosed in greater detail.

Referring again to FIG. 11, FIG. 12, FIG. 13 and FIG. 14, The enucleation device 300 comprises a motor adapter 306 at the proximal end 302 connected distally to the barrel 322. The motor adapter 306 is used to connect the enucleation device 300 to a motor drive (not shown), capable of transmitting axial rotation to the distal end 304 of the enucleation device 300 to function as disclosed in this disclosure. In one embodiment, when used for cutting intervertebral disk material in the method of the present invention, the dimensions of the motor adapter 306 are about 11 cm in axial length by 3.8 cm in maximum outer diameter by 3.3 cm in maximum inner diameter. However, the dimensions can be any suitable dimensions for the intended use, as will be understood by those with skill in the art with reference to this disclosure. The motor drive used with the enucleation device 300 of the present invention can be any suitable motor drive. In a preferred embodiment, the motor drive is a variable speed motor drive. In one embodiment, by way of example only, the motor drive is an NSK Electer EMAX motor drive (NSK Nakanishi Inc.). In another embodiment, the motor drive is a hand drill (for example, P/N C00108, Vertelink Corporation, Irvine, Calif.

US) connected to the motor adapter 306 by interfacing with the optional chuck adapter 308.

The enucleation device 300 further comprises a bearing assembly, comprising the bearing cap 310, the proximal bearing 312, the collet adapter 314, the distal bearing 316, and the bearing housing 318. The bearing housing 318 retains the proximal bearing 312, the collet adapter 314 and the distal bearing 316, which are preferably pressed into the bearing housing 318. In a preferred embodiment, the proximal bearing 312 and the distal bearing 316 are high-speed stainless steel radial bearings, such as for example only, P/N 57155k53, McMaster-Carr Supply Company, Santa Fe Springs, Calif. US. The collet adapter 314 is used to adapt the shaft 330 to a motor collet of the motor drive (not shown). The collet adapter 314 is connected to the shaft 330, such as for example only, by silver soldering. In one embodiment, the collet adapter 314 has an axial lumen for receiving a guidewire. In a preferred embodiment, the axial lumen has a diameter of about 2 mm.

The enucleation device 300 further comprises a barrel 322, which preferably has an axial lumen for receiving a guidewire, and a barrel knob 324 overlying the barrel 322, such as for example, by being press fitted on the barrel 322. The barrel knob 324 allows an operator to grasp the enucleation device 300 while advancing and retracting the enucleation device 300.

The enucleation device further comprises a hypotube 328. In one embodiment, when used for cutting intervertebral disk material in the method of the present invention, the hypotube 328 has an outer diameter of about 3.8 mm, an inner diameter of about 3 mm and an axial length of about 175 mm.

The enucleation device further comprises a shaft 330. In one embodiment, the shaft 330 has an axial lumen for receiving a guidewire. In a preferred embodiment, the shaft 330 is flexible to permit the enucleation device 300 to be advanced through a curved passage. In one embodiment, the shaft 330 is part number FS085T11C, PAK Mfg., Inc. In one embodiment, when used for cutting intervertebral disk material in the method of the present invention, the shaft 330 has an outer diameter of about 2 mm, an inner diameter of about 3 mm and an axial length of about 350 mm. When used with a guidewire, the shaft 330 has an inner diameter of about 1 mm.

The enucleation device 300 further comprises a threaded adapter 320 that connects the bearing assembly and the hypotube 328 to the barrel 322. In one embodiment, the threaded adapter 320 has a single thread proximally for interfacing with the bearing housing 318. In one embodiment, the threaded adapter 320 has an axial lumen for receiving a guidewire. In a preferred embodiment, the axial lumen has a diameter of between about 3 mm and 4 mm. In a preferred embodiment, the threaded adapter 320 has an axial length of about 13 mm and a maximum outer diameter of about 5 mm.

The enucleation device 300 further comprises a spacer tube 326 having an axial lumen. The spacer tube 326 decreases the diameter of the axial lumen of the barrel 322. In one embodiment, the axial lumen of the spacer tube 326 has a diameter of about 4 mm.

The enucleation device 300 further comprises a shrink tube 332 covering the distal end of the shaft 330. The shrink tube 332 provides a bearing surface between the hypotube 328 and shaft 330. In one embodiment, when used for cutting intervertebral disk material in the method of the present invention, the shrink tube 332 has an outer diameter of about 3.3 mm, an inner diameter of about 2.5 mm and an axial length of about 350 mm. By way of example only, a suitable shrink tube can be purchased from Zeus Industrial Products, Orangeburg, S.C. US.

The enucleation device 300 further comprises a cutting cap 334 at the distal end 304 of the enucleation device 300. The cutting cap 334 comprises a plurality of deformable blades 336 that orthogonally-expand when the blades 336 are not deformed. Each blade 336 has one or more than one cutting edge. In one embodiment, the plurality of blades comprises two or more than two blades. In another embodiment, the plurality of blades comprises three blades. In a preferred embodiment, the plurality of blades comprises four blades. The blades 336, and preferably, the entire cutting cap 334, comprises a shaped metal alloy, such a nitinol, that has been processed to return the blades 336 to an orthogonally-expanded cutting configuration suitable for cutting when undeformed. In one embodiment, when used for cutting intervertebral disk material in the method of the present invention, the cutting cap 334 has an outer diameter of about 3 mm, an inner diameter of about 2.2 mm and an axial length of about 11 mm when deformed. When undeformed and activated, the spinning blades cover a cross-sectional area of about 1.8 cm, that is, an area having a diameter of about 1.5 cm.

The enucleation device 300 can be made by any suitable method, as will be understood by those with skill in the art with reference to this disclosure. In one embodiment, the enucleation device 300 is made in part by the following steps. The spacer tube 326 is introduced over the distal end of the hypotube 328 and barrel 322 and is pressed into the barrel until the spacer tuber 326 is flush with the distal end of the barrel 322. The threaded adapter 320 is connected to the proximal end of hypotube 328, such as for example only, by silver soldering, and the threaded adapter 320 and hypotube 328 are inserted into the proximal end of the barrel 322 until they come to a stop and they are secured to the barrel 322 with a setscrew (not shown). The bearing housing 318 is screwed onto the threaded adapter 320 and a distal bearing 316 is pressed into the bearing housing 318. The shaft 330 is inserted into the bearing housing 318 through the distal bearing 316 and bearing housing 318, and the collet adapter 314 is placed over the shaft 330 and soldered onto the shaft approximately 50 mm from the proximal end of the shaft 330. The proximal bearing 312 is placed over the proximal end of the collet adapter 314. The bearing cap 310 is screwed onto the proximal end of the bearing housing 318 until the bearing cap 310 stops. The barrel assembly is inserted into the motor adapter 306 and is keyed through a slot in the side of the motor adapter 306. The shrink tube 332 is placed over the distal end of the shaft 330. The cutting cap 334 is crimped or bonded to the distal end of the shaft 330.

The enucleation device of the present invention can be used to cut any suitable material, as will be understood by those with skill in the art with reference to this disclosure. In a preferred embodiment, the enucleation device is used to cut away intervertebral disk from an intervertebral space between two vertebral bodies after accessing the intervertebral space through a passage in the pedicle of the vertebra superior to the intervertebral space, where the passage has a smaller cross-sectional area than the lateral cross-sectional area of the undeformed blades while the blades are cutting the material. In a preferred embodiment, the enucleation device is also used to cut away vertebral body endplates bordering the intervertebral space.

By way of example only, the enucleation device can be used to cut material in a space when the blades are not deformed, after accessing the space through a channel while the blades are deformed, where the channel has a smaller cross-sectional area than the cross-sectional area of the plurality of undeformed blades while the blades are cutting the material as follows. First, the blades are deformed to fit through a previously created channel. Deformation comprises moving the distal tips of each blade toward the long axis of the enucleation device, preferably, until the long axis of each blade is coaxial with the long axis of the enucleation device. Next, the cutting cap of the enucleation device is advanced through the channel, and the distal end of the enucleation device is allowed to pass into the space, thereby allowing the blades to expand orthogonally, that is to allow the distal tips of each blade to move away from the long axis of the enucleation device, perpendicular to the long axis of the enucleation device, to their undeformed shape. In a preferred embodiment, the channel is significantly curved, and the enucleation device has a shaft allowing the enucleation device to follow the curvature of the channel as the enucleation device is advanced. Next, the enucleation device is actuated causing the blades to rotate, thereby affecting cutting of the material. In a preferred embodiment, the blades are rotated at between about 100 and 15000 RPM. Additionally, the enucleation device can be advanced and retracted in the space to cut additional material. Once completed, the enucleation device is withdrawn causing the blades to deform until they have been withdrawn from the channel.

In a preferred embodiment, the enucleation device is advanced through the channel over a guide wire. In another preferred embodiment, the enucleation device is passed through a sheath lining the channel. In another preferred embodiment, the material cut is intervertebral disk. In a particularly preferred embodiment, the shaft of the enucleation device is flexible to permit the enucleation device to advance through a curved passage. In another particularly preferred embodiment, the material is vertebral body endplate material. In another particularly preferred embodiment, the channel is a transpedicular access channel in a vertebra.

Figure 15:
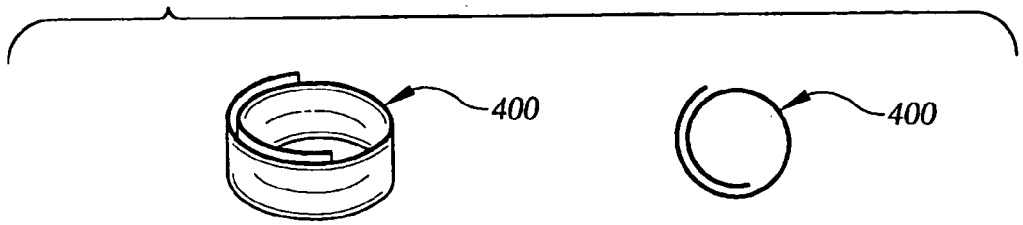
FIG. 15 shows both a lateral perspective view (left) and a top perspective view (right) of a fusion agent containment device according to one embodiment of the present invention in a deformed configuration.
Figure 16:
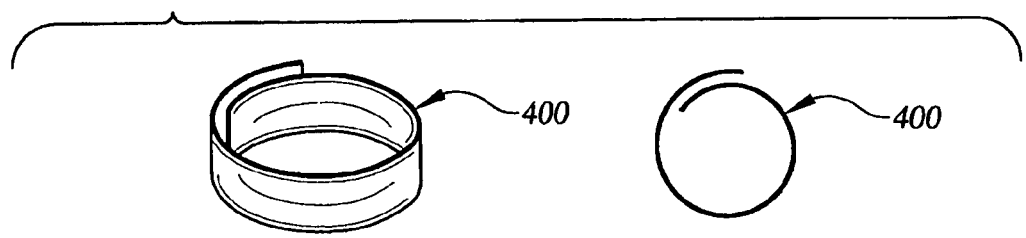
FIG. 16 shows both a lateral perspective (left) and a top perspective view (right) of the fusion agent containment shown in FIG. 15 in an undeformed configuration.

In another embodiment, the present invention is a fusion agent containment device for containing a fusion agent within a chamber formed within an intervertebral disk space. Referring now to FIG. 15 and FIG. 16, there are shown in each Figure a lateral perspective view (left) and a top perspective view (right) of a fusion agent containment device 400 according to one embodiment of the present invention expanding from a first, deformed configuration, FIG. 15 to a second undeformed configuration, FIG. 16. As can be seen, the fusion agent containment device 400 comprises a band comprising a thin, biocompatible, deformable material having shape memory configured to expand into a substantially circular or oval shape when undeformed. In a preferred embodiment, the band comprises a shaped metal alloy, such as nitinol, that has been processed to return to an undeformed configuration, approximating the boundaries of the empty space within the intervertebral disk space created during the method of the present invention. In a particularly preferred embodiment, the band is coated with a biocompatible sealant, such as hydrogel. The dimensions of the fusion agent containment device 400 will vary with the intended use as will be understood by those with skill in the art with reference to this disclosure. By example only, in a preferred embodiment, the band expands upon deployment to approximately 1 cm in height and 2 cm in diameter.

Figure 17:
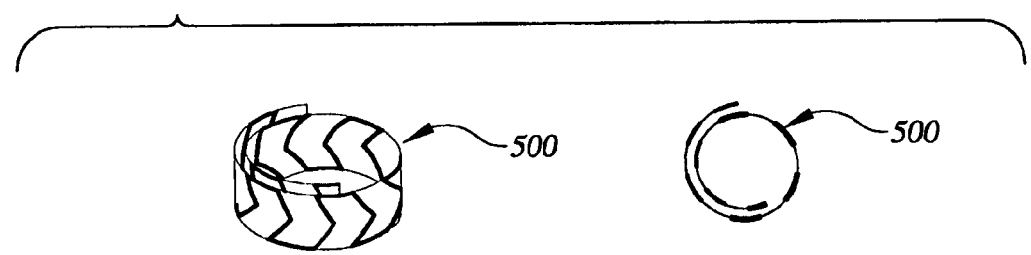
FIG. 17 shows both a lateral perspective (left) and a top perspective view (right) of another fusion agent containment device according to one embodiment of the present invention in a deformed configuration.
Figure 18:
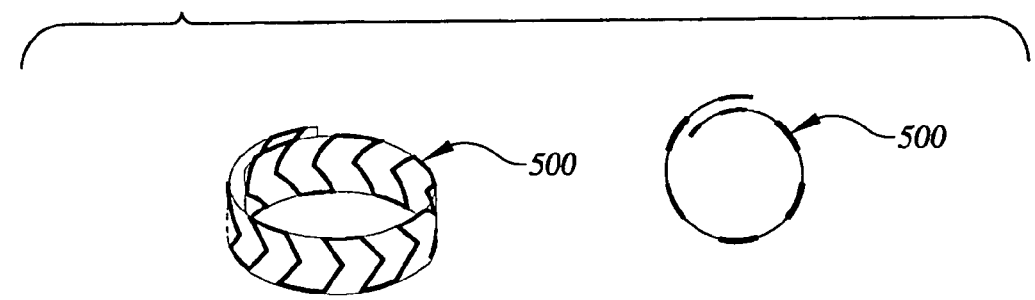
FIG. 18 shows both a lateral perspective (left) and a top perspective view (right) of the fusion agent containment shown in FIG. 17 in an undeformed configuration.
Figure 19:
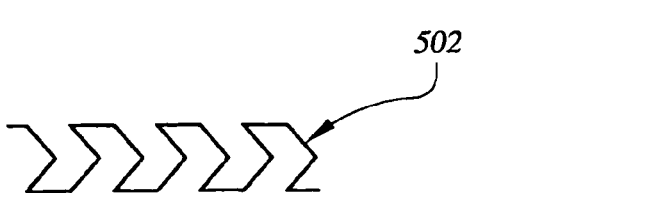
FIG. 19 shows an isolated section of wire that forms the fusion agent containment shown in FIG. 17 and FIG. 18.
Figure 38:
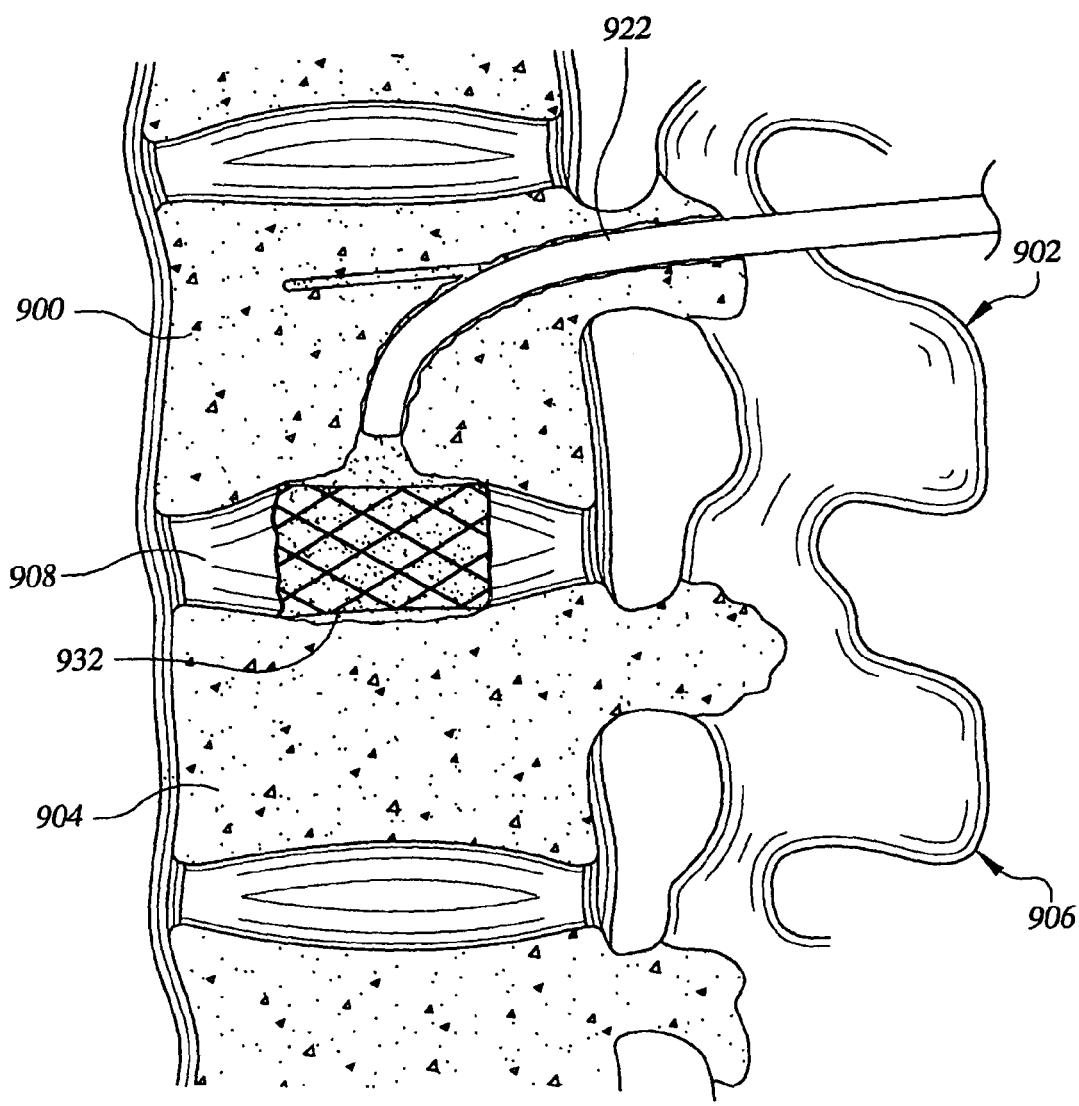
Figure 39:
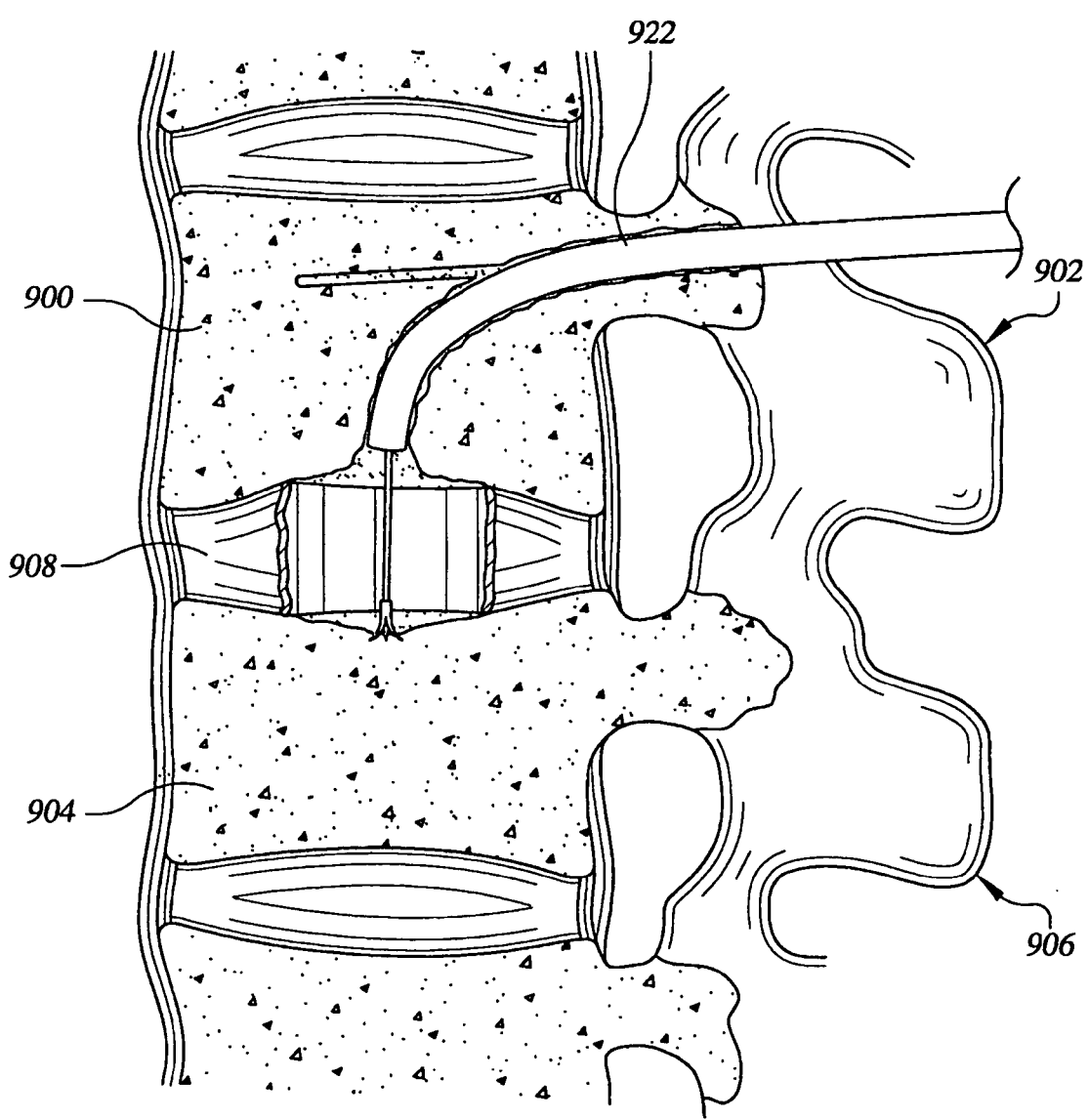
Figure 40:
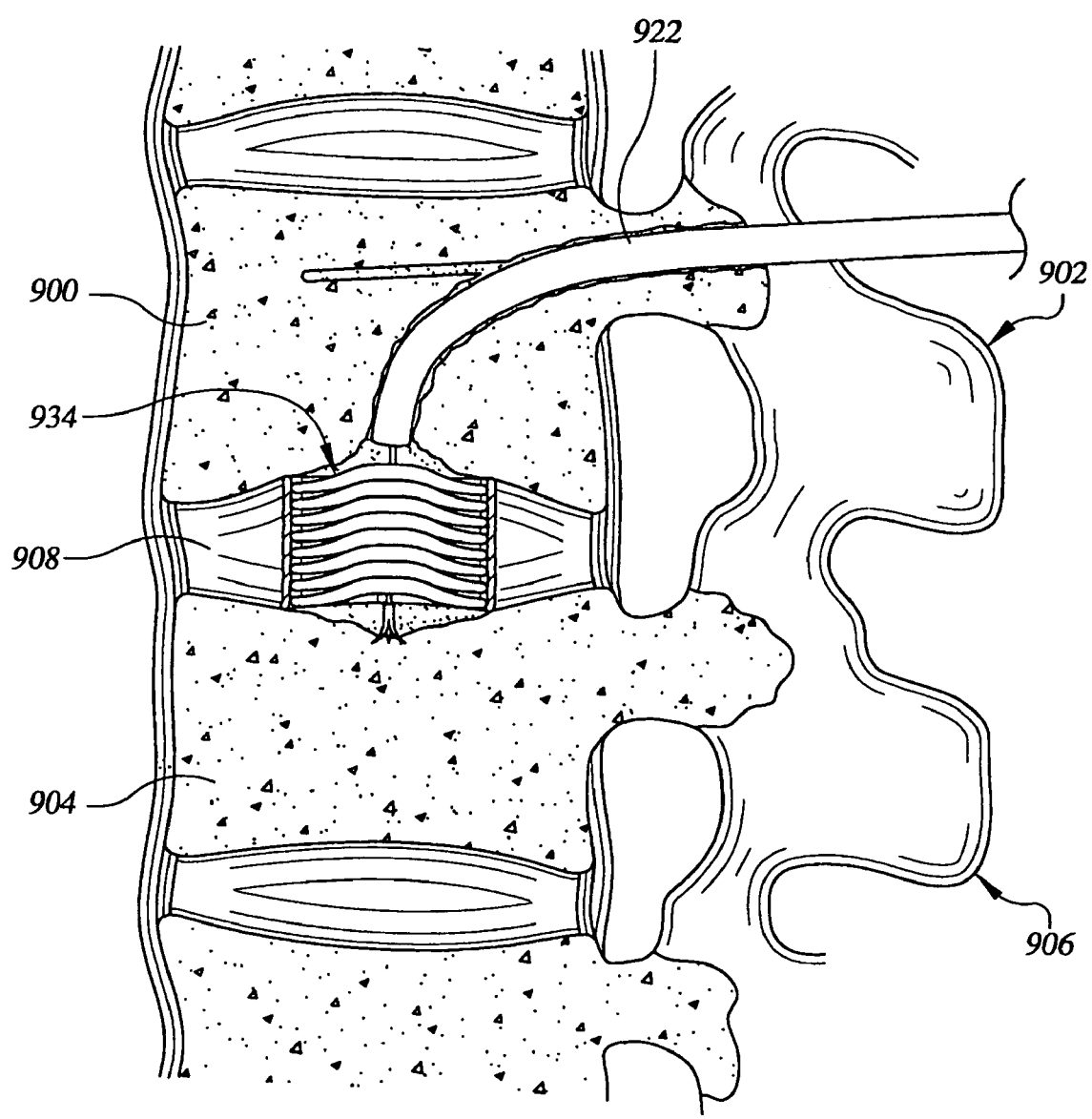
Figure 41:
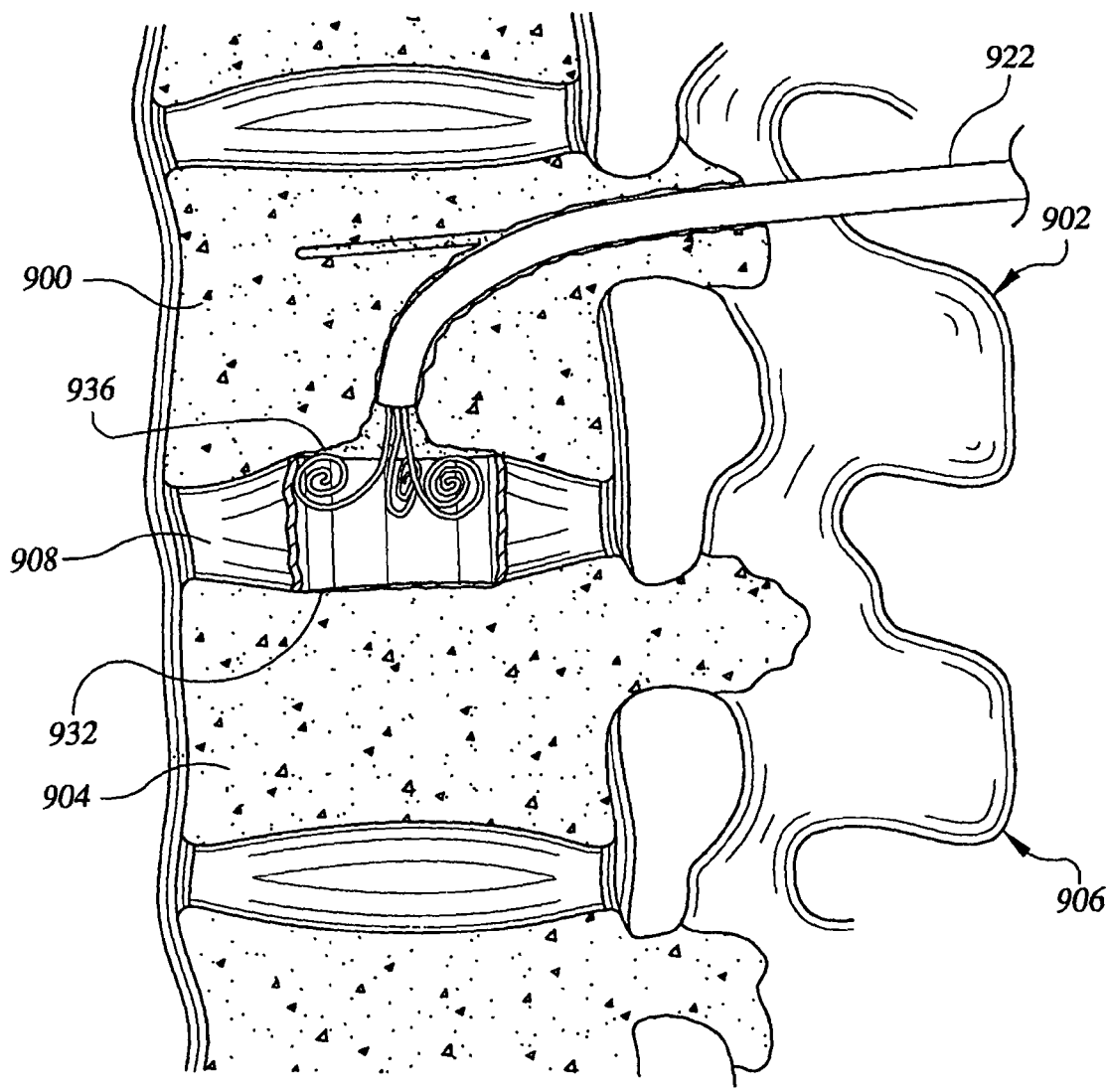
Figure 42:
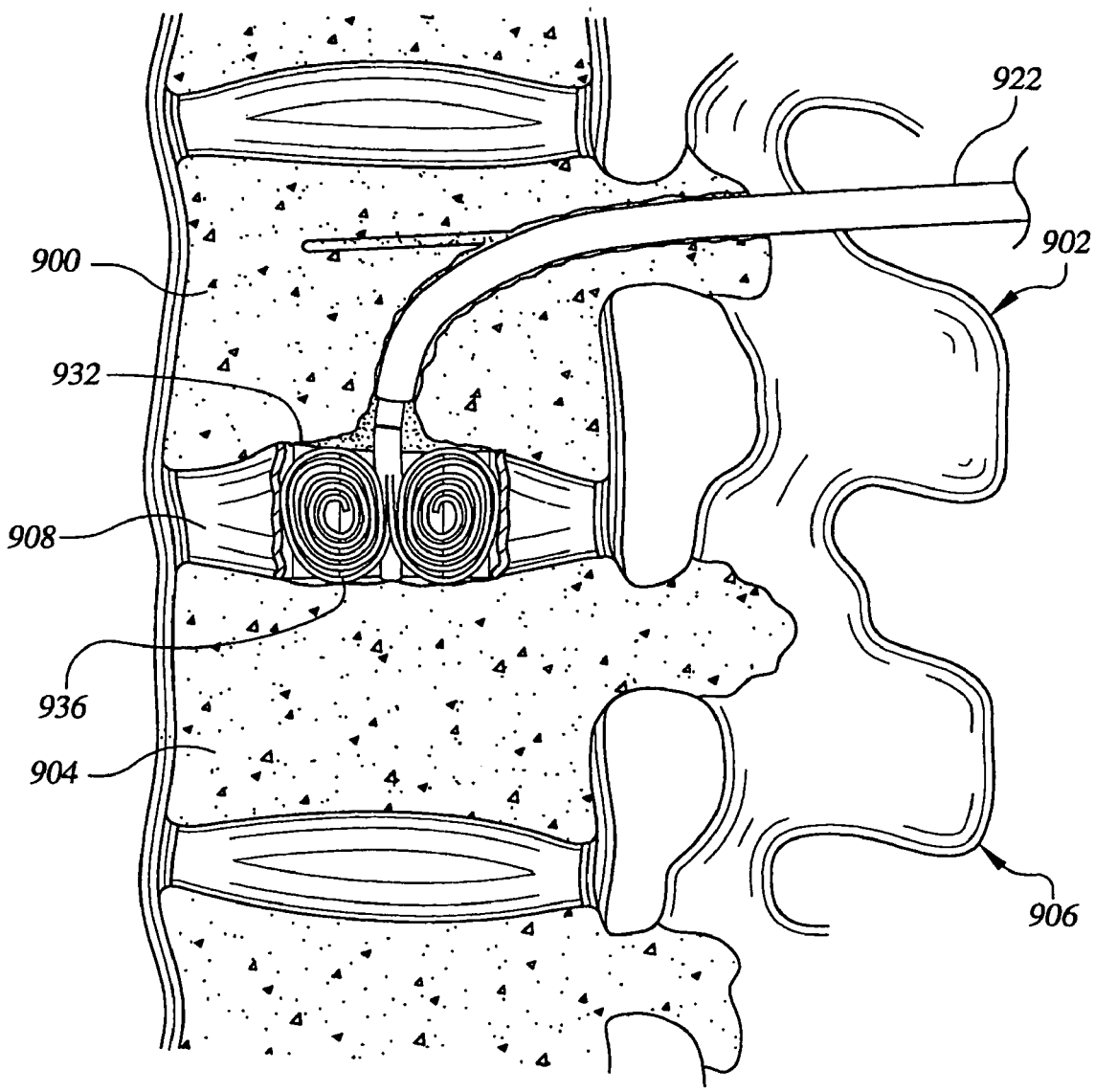
Figure 43:
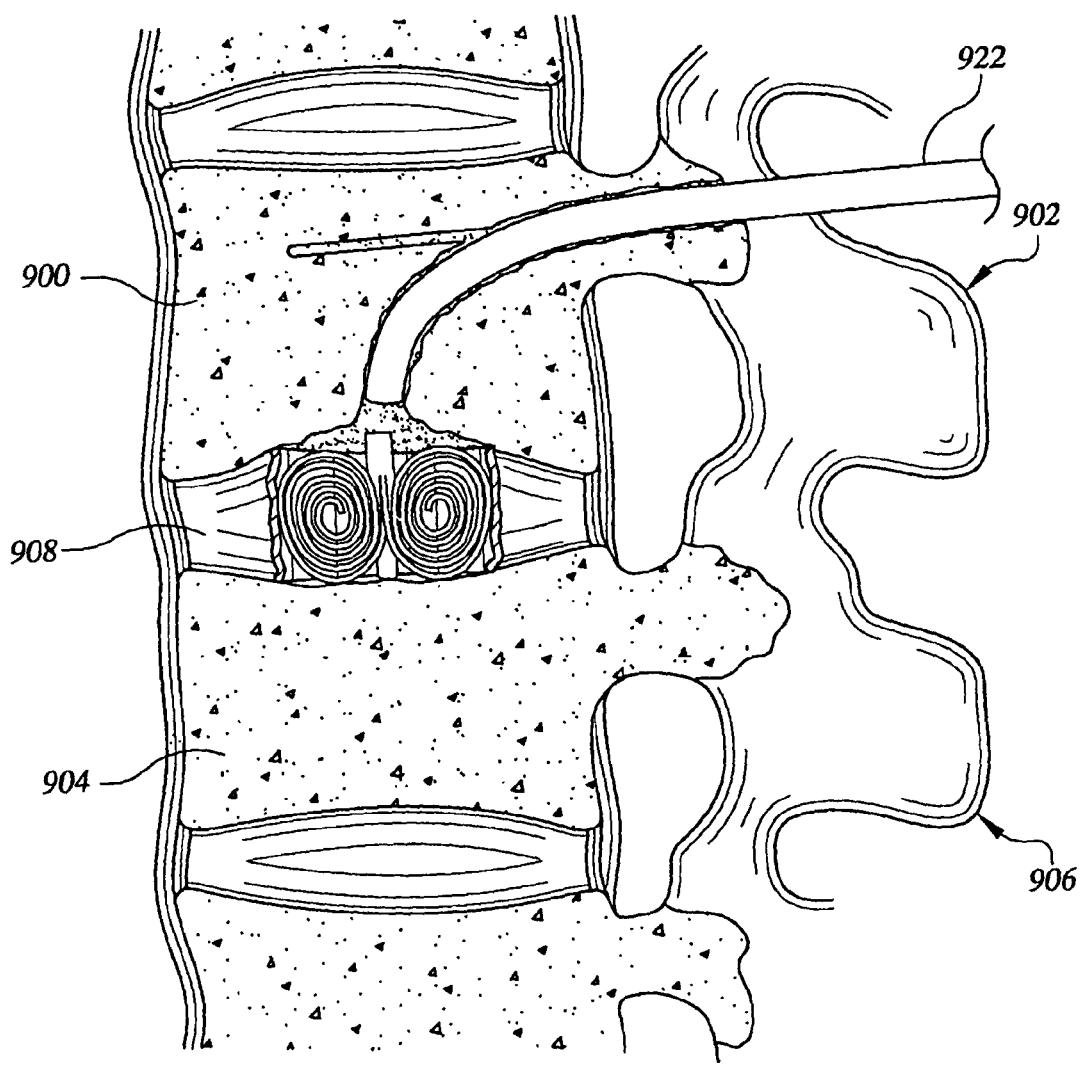
Figure 44:
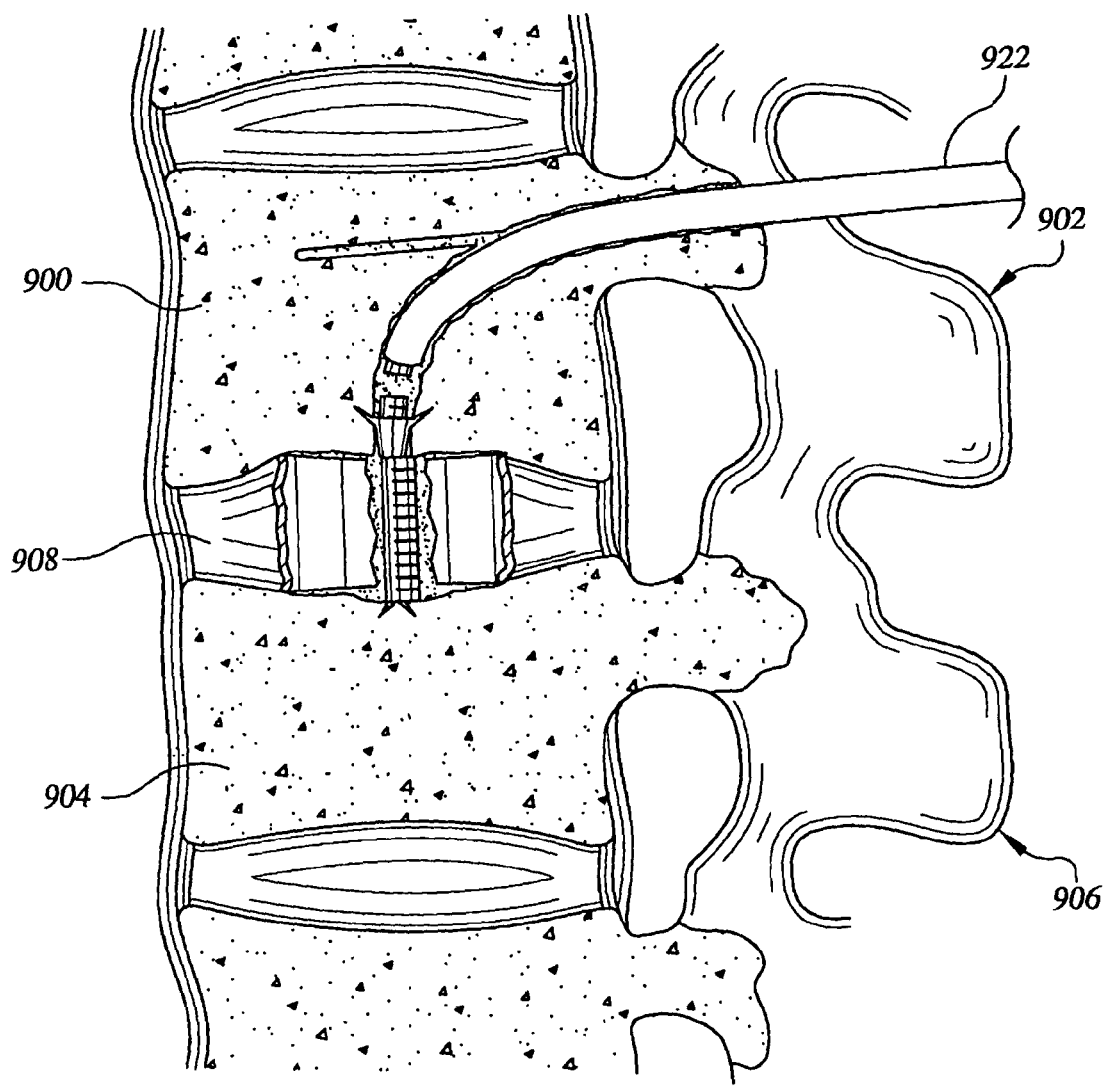
Figure 53:
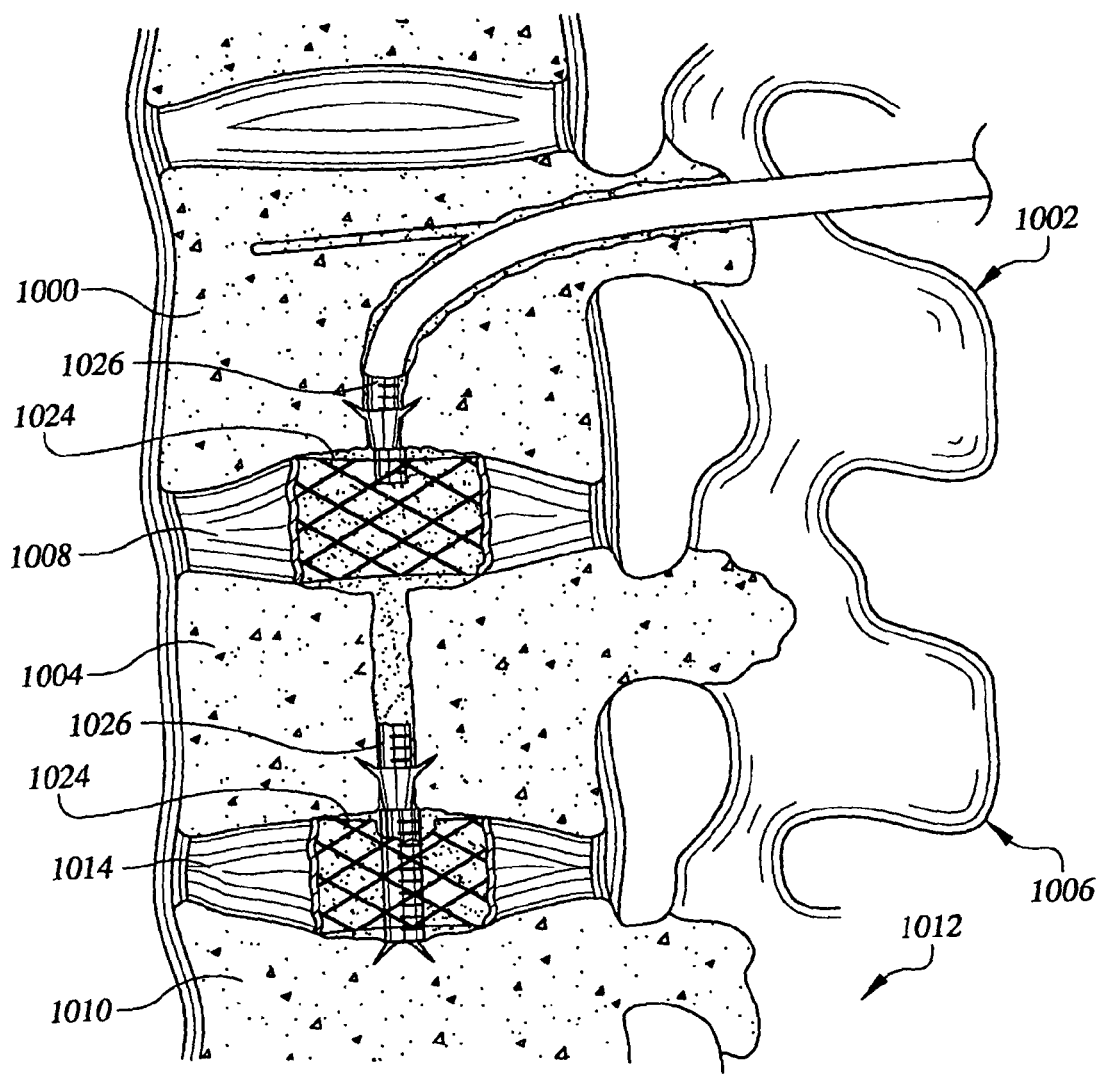
Figure 54:
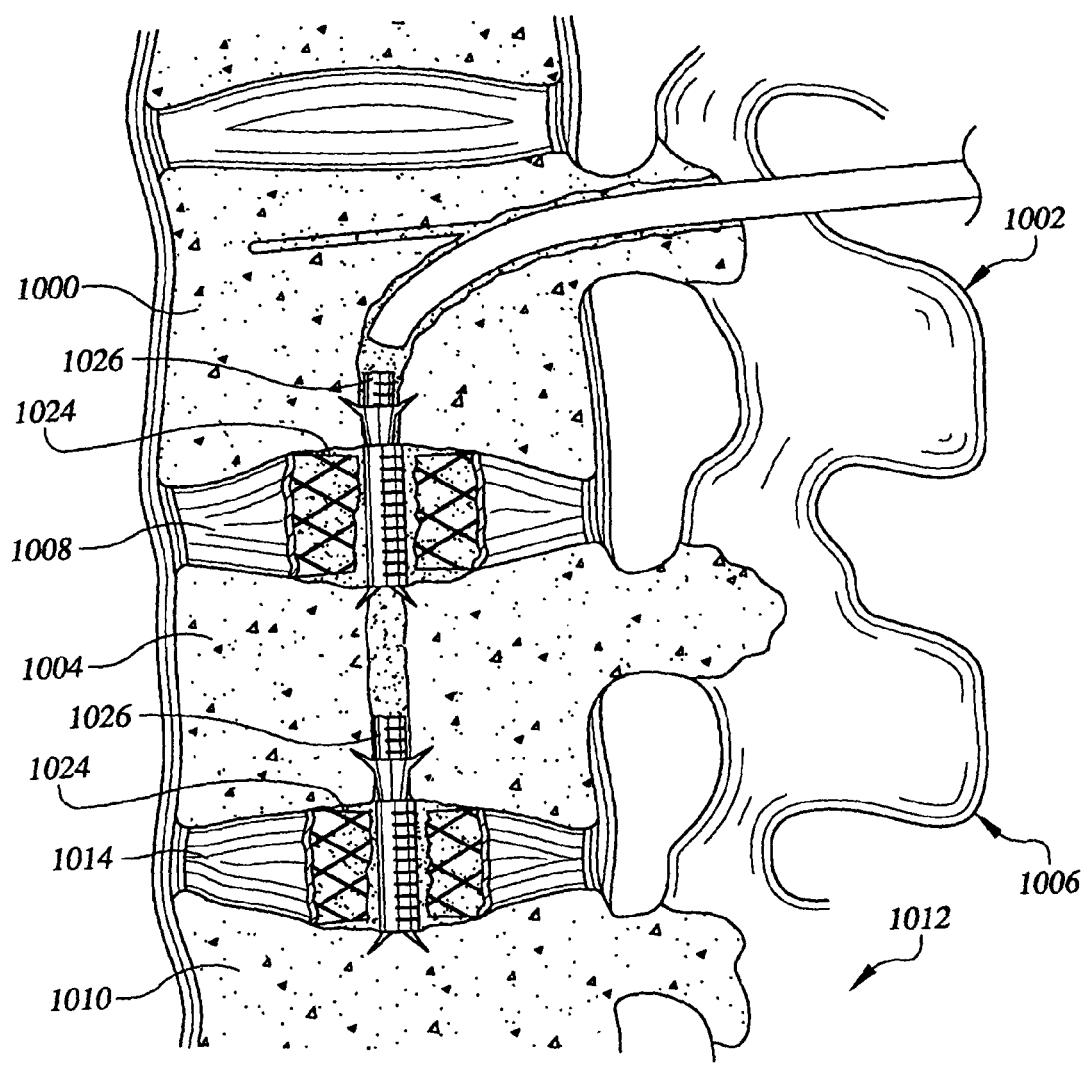

In another embodiment, the present invention is a fusion agent containment device for containing a fusion agent within a chamber formed within an intervertebral disk space. Referring now to FIG. 17 and FIG. 18, there are shown in each Figure a lateral perspective view (left) and a top perspective view (right) of a fusion agent containment device 500 according to one embodiment of the present invention expanding from a first, deformed configuration, FIG. 17 to a second undeformed configuration, FIG. 18. As can be seen, the fusion agent containment device 500 comprises wire comprising a thin, biocompatible, deformable material having shape memory configured to expand into a substantially circular or oval shape when undeformed. The fusion agent containment device 500 can be formed from wire shaped into a variety of configurations, as will be understood by those with skill in the art with reference to this disclosure. FIG. 19 shows an isolated section of wire 502 that forms the fusion agent containment shown in FIG. 17 and FIG. 18. In a preferred embodiment, the wire comprises a mesh, as shown in FIG. 38, FIG. 53 and FIG. 54, because a mesh can be deformed both circumferentially and axially. In one embodiment, the wire comprises a shaped metal alloy, such as nitinol, that has been processed to return to an undeformed configuration, approximating the boundaries of the empty space within the intervertebral disk space created during the method of the present invention. In a particularly preferred embodiment, the wire mesh is coated with a biocompatible sealant, such as hydrogel. The dimensions of the fusion agent containment device 500 will vary with the intended use as will be understood by those with skill in the art with reference to this disclosure. By example only, in a preferred embodiment, the band expands upon deployment to approximately 1 cm in height and 2 cm in diameter.

In another embodiment, the present invention is a method of fusing two adjacent vertebrae using a fusion agent containment device of the present invention. The method comprises, first, creating a chamber within the intervertebral disk space between two adjacent vertebrae. Next, a fusion agent containment device according to the present invention is provided and is placed within the chamber and allowed to expand to its undeformed configuration. Then, the fusion agent containment device is filled with a fusion agent and the fusion agent is allowed to fuse the two adjacent vertebrae. In a preferred embodiment, the method further comprises additionally fusing the two adjacent vertebrae with a second procedure.

Figure 20:
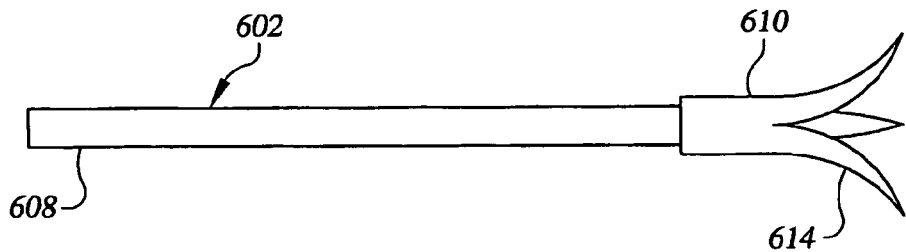
FIG. 20 is a lateral perspective view of an introducer of a distraction system according to one embodiment of the present invention.
Figure 21:
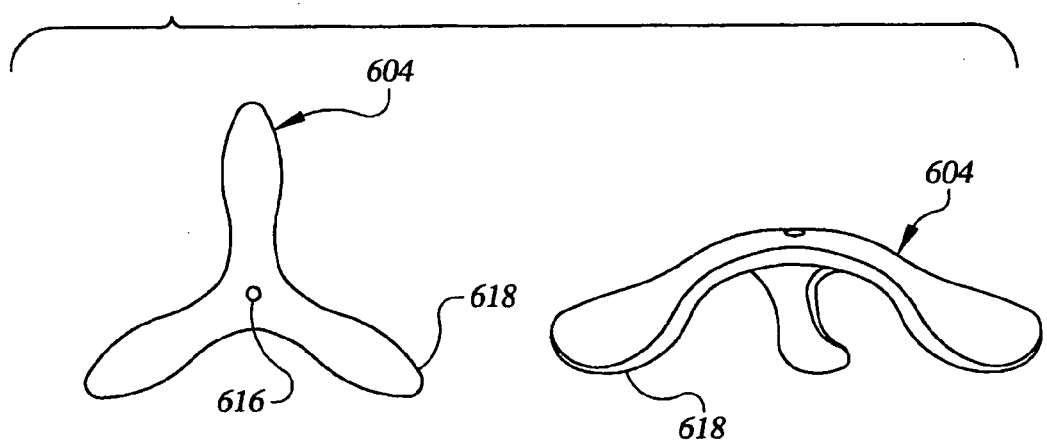
FIG. 21 is a lateral perspective view (left) and a top perspective view (right) of one embodiment of a spacing component of the distraction system including the introducer shown in FIG. 20.
Figure 22:
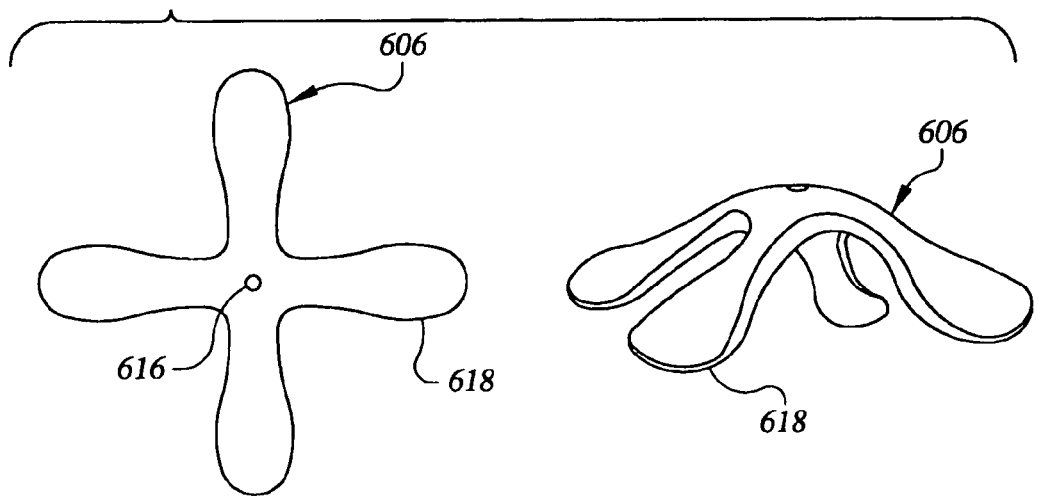
FIG. 22 is a lateral perspective view (left) and a top perspective view (right) of one embodiment of another spacing component of the distraction system including the introducer shown in FIG. 20.

In another embodiment, the present invention is a distraction system for distracting two adjacent vertebrae. Referring now to FIG. 20, FIG. 21 and FIG. 22, there are shown, respectively, a lateral perspective view of an introducer of the distraction system; a lateral perspective view (left) and a top perspective view (right) of one embodiment of a spacing component of the distraction system; and a lateral perspective view (left) and a top perspective view (right) of another embodiment of a spacing component of the distraction system. As can be seen, the distraction system 600 comprises an introducer 602 and a plurality of spacing components 604, 606. The introducer 602 comprises a proximal insertion portion 608 and a distal anchoring portion 610. The proximal insertion portion 606 comprises a guidewire-type or tubular structure 612. The distal anchoring portion 610 comprises a plurality of barbs 614.

Figure 23:
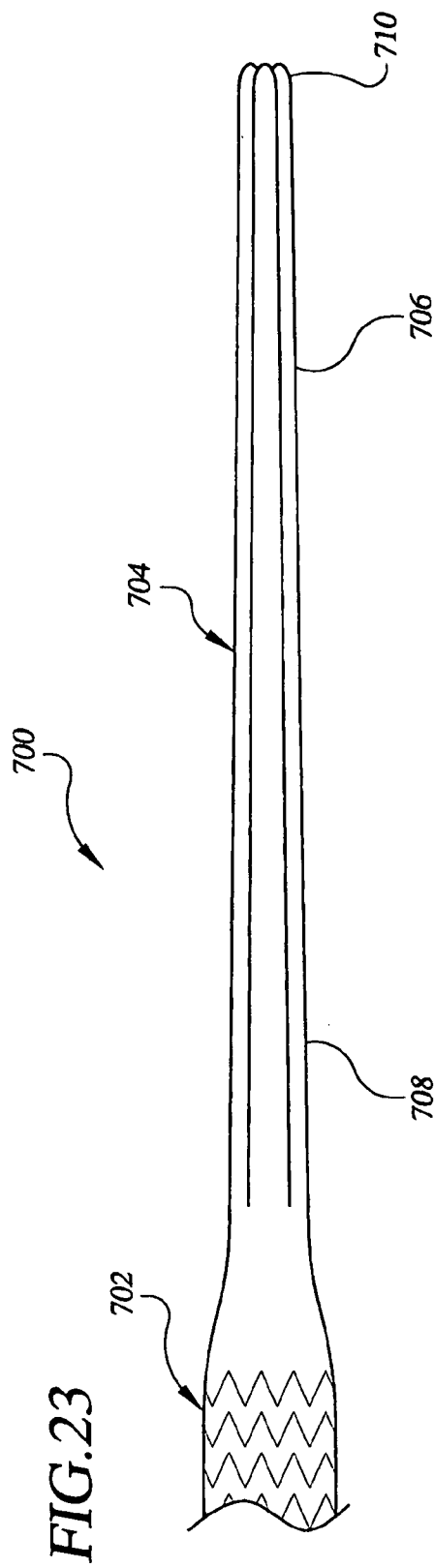
FIG. 23 is a lateral perspective view of another distraction system according to the present invention in the undeformed configuration.
Figure 24:
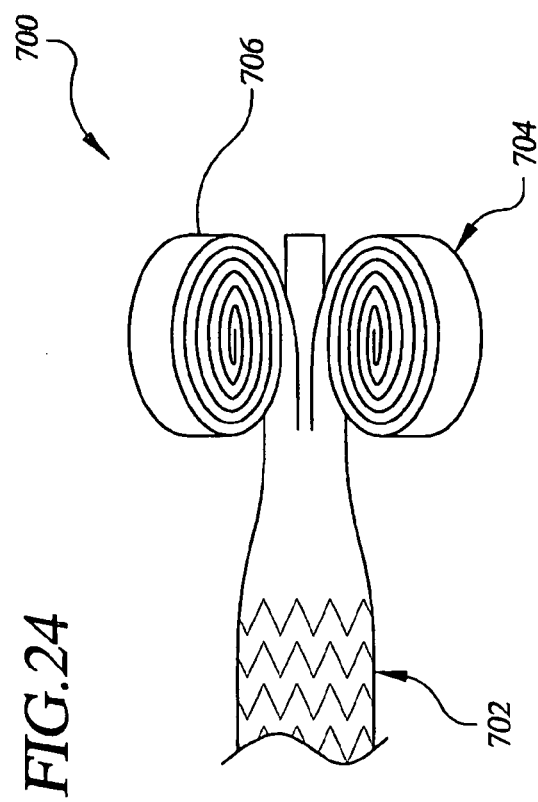
FIG. 24 is a lateral perspective view of the distraction system shown in FIG. 23 in the deformed configuration.

The distraction system 600 further comprises a plurality of stackable, deformable, spacing components 604, 606. Each spacing component preferably comprises a central opening 616 and a plurality of extensions 618. In a preferred embodiment, each spacing component comprises three extensions 618, as shown in FIG. 21. In another preferred embodiment, each spacing component comprises four extensions 618, as shown in FIG. 22. The spacing components 604 are configured such that each extension forms a curved shape to allow stacking of a plurality of spacing components 604, 606 axially onto the introducer 602. In a preferred embodiment, each spacing component 604, 606 of the distraction system 600 comprises a substance, such as shaped metal alloy, for example nitinol, that has been processed to return to a shape suitable for distracting two adjacent vertebral bodies as used in the method of the present invention. Further, each surface of the distraction system 600 preferably has a polytetrafluoroethylene or other hydrophilic coating to decrease friction between components of the distraction system 600. In another embodiment, not shown, the spacing components can In another embodiment, the present invention is another distraction system for distracting two adjacent vertebrae. Referring now to FIG. 23 and FIG. 24, there are shown, respectively, a lateral perspective view of another distraction system according to the present invention in the undeformed configuration; and a lateral perspective view of the distraction system in the deformed configuration. As can be seen, the distraction system 700 comprises a proximal connecting portion 702 and a distal distracting portion 704. The proximal connecting portion 702 comprises a tubular structure comprising a solid band, a mesh or equivalent structure. The distal distracting portion 704 comprises a plurality of strips 706. Each strip is deformable from an extended undeformed configuration to a curled deformed configuration. The strips 706 are connected at their proximal end to the proximal connecting portion 702. Each strip 706 is preferably tapered from the proximal end to the distal end. In a preferred embodiment, each strip 706 tapers from between about 2.5 and 3 mm wide at the proximal end 708 to about 1 mm wide at the distal end 710, and tapers from about 1 mm thick at the proximal end 708 to between about 0.1 and 0.2 mm thick at the distal end 710. The distraction system 700 comprises a substance, such as shaped metal alloy, for example nitinol, that has been processed to return to a shape suitable for distracting two adjacent vertebral bodies as used in the method of the present invention. Further, each surface of the distraction system 700 preferably has a polytetrafluoroethylene or other hydrophilic coating to decrease friction between components of the distraction system 700.

The distraction system 700 can be made by any suitable method, as will be understood by those with skill in the art with reference to this disclosure. In one embodiment, there is provided a method of making a distraction system, according to the present invention. In this embodiment, the distraction system is made by, first, providing a cylinder of biocompatible, shaped metal alloy, such as nitinol. Then, a plurality of axial cuts are made into the cylinder to produce a plurality of separated strips at the distal end of the hypotube. In a particularly preferred embodiment, the cylinder is cut into three strips at the distal end. The strips that are then bent into tight spirals and heat annealed to return to this shape when undeformed. In a preferred embodiment, the group of spirals when undeformed has a maximum transverse profile of about 2 cm and a maximum axial profile of about 1 cm. In another embodiment, the strips are disconnected from the proximal end of the cylinder and connected, such as by soldering, to a mesh cylinder made of the same or equivalent material.

Figure 25:
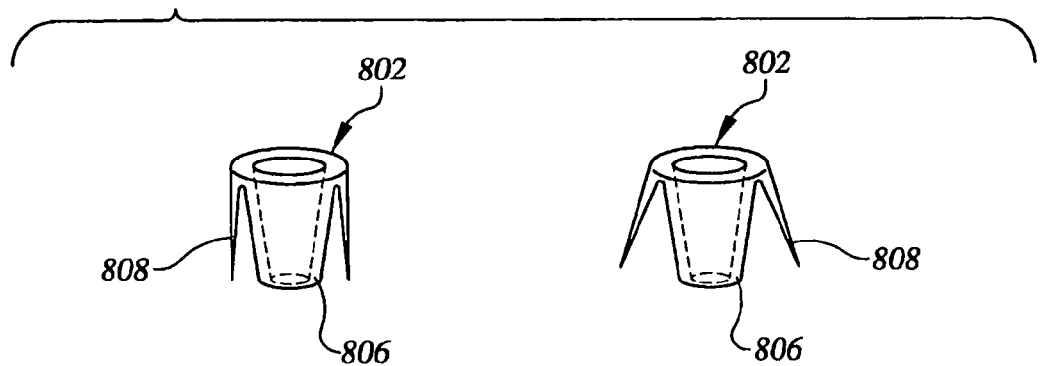
FIG. 25 is a lateral perspective view of the barbed plug of another distraction system according to the present invention in the deformed configuration (left) and in the undeformed configuration (right)
Figure 26:
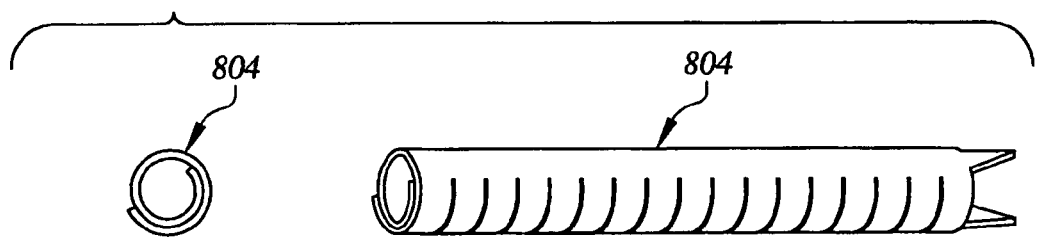
FIG. 26 is a top perspective view (left) and a lateral perspective view (right) of the rachet device of the distraction system including the barbed plug shown in FIG. 25 in the deformed configuration.
Figure 27:
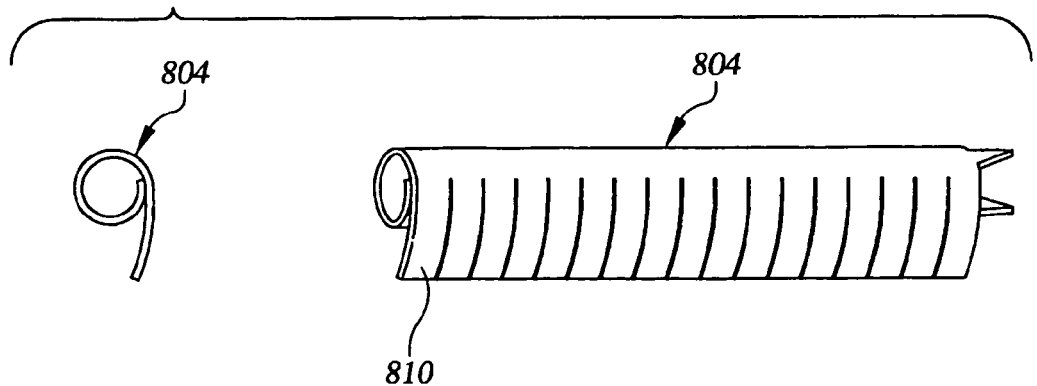
FIG. 27 is a top perspective view (left) and a lateral perspective view (right) of the rachet device of the distraction system including the barbed plug shown in FIG. 25 in the undeformed configuration.

In another embodiment, the present invention is another distraction system for distracting two adjacent vertebrae. Referring now to FIG. 25, FIG. 26 and FIG. 27, there are shown, respectively, a lateral perspective view of the barbed plug of the distraction system according to the present invention in the deformed configuration (left) and in the undeformed configuration (right); a top perspective view (left) and a lateral perspective view (right) of the rachet device of the distraction system in the deformed configuration; and a top perspective view (left) and a lateral perspective view (right) of the rachet device of the distraction system in the undeformed configuration. As can be seen, the distraction system 800 comprises a barbed plug 802, and comprises a ratchet device 804. The barbed plug 802 comprises a cylindrical or conical central portion 806 and a plurality of barbs 808 distally. When deformed, FIG. 20-*left*, the barbs 808 of the barbed plug 802 contract toward the axial center of the barbed plug 802. When undeformed, FIG. 25 (right), the barbs 808 of the barbed plug 802 extend outward from the axial center of the barbed plug 802. The barbed plug is formed from a cone or cylinder that is cut axially to form the plurality of barbs and then heat annealed to return to this shape. The ratchet device 804 comprises a series of transversely separated strips 810 connected at one end. The ratchet device is formed from a sheet that is cut transversely into a plurality of strips connected at one end of the sheet. The sheet is rolled axially and heat annealed to return to this shape. When deformed, FIG. 26 (left), the strips 810 are tightly coiled about the central axis of the ratchet device 804. When undeformed, FIG. 27 (right), the strips 810 uncoil away from the central axis of the ratchet device 804. Each component of the distraction system 800 comprises a substance, such as shaped metal alloy, for example nitinol, that has been processed to return to a shape suitable for distracting two adjacent vertebral bodies as used in the method of the present invention. Further, each surface of the distraction system 800 preferably has a polytetrafluoroethylene or other hydrophilic coating to decrease friction between components of the distraction system 800.

In another embodiment, the present invention is a method of distracting a superior vertebra from an inferior vertebra using a distraction system of the present invention. The method comprises, first, creating a chamber is created within the intervertebral disk space between two adjacent vertebrae. Next, a distraction system according to the present invention is provided and is placed within the chamber, thereby distracting the two adjacent vertebrae. In one embodiment, the distraction system comprises an introducer comprising a proximal insertion portion and a distal anchoring portion comprising a plurality of barbs, and comprises a plurality of stackable, deformable spacing components. In this embodiment, placing the distraction system within the chamber comprises advancing the introducer until the barbs encounter cancellous bone in the superior portion of the distal vertebral body of the two adjacent vertebrae, inserting the plurality of spacing components in their deformed configuration over the introducer into the chamber, and allowing the plurality of spacing components to expand to their undeformed configuration. In another embodiment, the distraction system comprises a proximal connecting portion and a plurality of strips connected at their proximal end to the proximal connecting portion. In this embodiment, placing the distraction system within the chamber comprises advancing the distraction system into the chamber through a channel while the strips are in a straightened, deformed shape. Once in the chamber, the strips return to their undeformed, spiral shape and distract the two vertebral bodies axially. In another embodiment, the distraction system comprises a barbed plug and a ratchet device. In this embodiment, placing the distraction system within the chamber comprises advancing the barbed plug in the deformed configuration into the chamber through a channel, with either the barbs facing proximally or distally, until the barbed plug enter the chamber. The barbs of the barbed plug then extend and contact cancellous bone in the superior portion of the distal vertebral body of the two adjacent vertebrae or in the inferior portion of the proximal vertebral body of the two adjacent vertebrae. Next, the ratchet device is advanced in the undeformed configuration through the channel and into the chamber and into the barbed plug. Once in the chamber, each strip of the ratchet device expands axially to prevent retraction through the channel and sufficient length of the ratchet device is advanced to cause the desired distraction of the two vertebrae. In a preferred embodiment, the distraction system is introduced bilaterally. In a preferred embodiment, the method comprises placing the distraction system through a channel created through the pedicle of the superior vertebra. In another preferred embodiment, the method additionally comprises placing the distraction system through a sheath or hypotube, within a channel created through the pedicle of the superior vertebra.

The present invention further comprises a method for treating diseases and conditions that change the spacial relationship between the vertebral bodies and the intervertebral disks, or that cause instability of the vertebral column, or both, and a method that allows the surgeon to access the intervertebral space to restore a more normal three-dimensional configuration of the space, with or without additionally fusing two adjacent vertebrae. Referring now to FIG. 28 through FIG. 45, there are shown partial, cutaway, lateral perspective views illustrating some aspects of the method as performed on a first vertebral body 900 of a first vertebra 902, a second vertebral body 904 of a second vertebra 906 and an intervertebral disk 908 between the first vertebral body 900 and second vertebral body 904.

In a preferred embodiment, the method comprises, first, selecting a patient who is suitable for undergoing the method. A suitable patient has one or more than one change in the spacial relationship between a first vertebral body of first a vertebra, a second vertebral body of a second vertebra adjacent the first vertebral body, and an intervertebral disk 908 between the first vertebral body and the second vertebral body, where the change in the spacial relationship is symptomatic, such as causing pain, numbness, or loss of function, or where the change in the spacial relationship is causing real or potential instability, or a combination of the preceding, necessitating a restoration of a more normal configuration or a change in the confirmation of the spacial relationship between the first vertebral body and the second vertebral body, or necessitating fusion of the first vertebra and the second vertebra, or necessitating both. However, other diseases and conditions can also be treated by the present methods, as will be understood by those with skill in the art with reference to this disclosure. Among the diseases and conditions potentially suitable for treatment are degenerated, herniated, or degenerated and herniated intervertebral disks, degenerative scoliosis, disk or vertebral body infections, space occupying lesions such as malignancies, spinal stenosis, spondylosis, spondylolisthesis, and vertebral instability, and injuries, including vertebral fractures due to trauma or osteoporosis, and to surgical manipulations, that change the spacial relationship between the vertebral bodies and the intervertebral disks, causing pain, disability or both, and that cause instability of the vertebral column. While the present method is disclosed and shown with respect to the first vertebral body 900 being superior to the second vertebral body 904, the present method can also be used with respect to a first vertebral body 900 that is inferior to the second vertebral body 904, as will be understood by those with skill in the art with reference to this disclosure.

Figure 28:
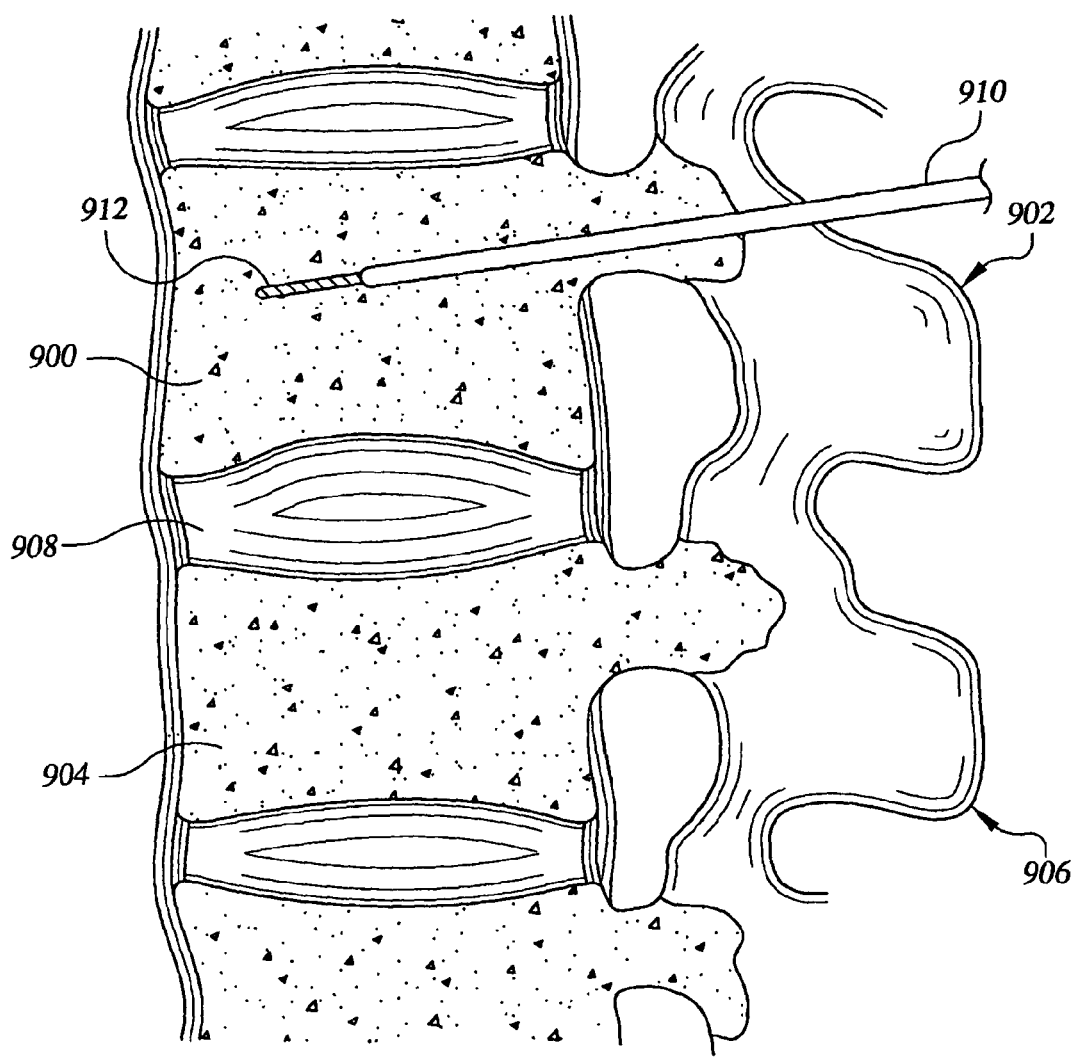

Next, transpedicular access to the first vertebral body 900 is obtained percutaneously, as shown in FIG. 28. In a preferred embodiment, the transpedicular access is obtained by inserting a suitable gauge bone biopsy needle 910, such as an 11-gauge bone biopsy needle (available, for example, from Parallax Medical, Scotts Valley, Calif. US; Allegiance Health Care, McGaw Park, Ill. US; and Cook, Inc., Bloomington, Ind. US), through one pedicle of the first vertebra under suitable guidance, such as fluoroscopic guidance. In a particularly preferred embodiment, transpedicular access is obtained bilaterally and the method disclosed in this disclosure is repeated bilaterally. Performance of the method bilaterally allows greater removal of disk material, and thus, a larger intervertebral cavity for the deposition of bone matrix material. Then, a suitable gauge guidewire 912, such as a 1 mm diameter guidewire, is inserted into the first vertebral body 900 through the biopsy needle 910, as shown in FIG. 28, and the biopsy needle 910 is removed leaving the inserted guidewire 912.

Figure 29:
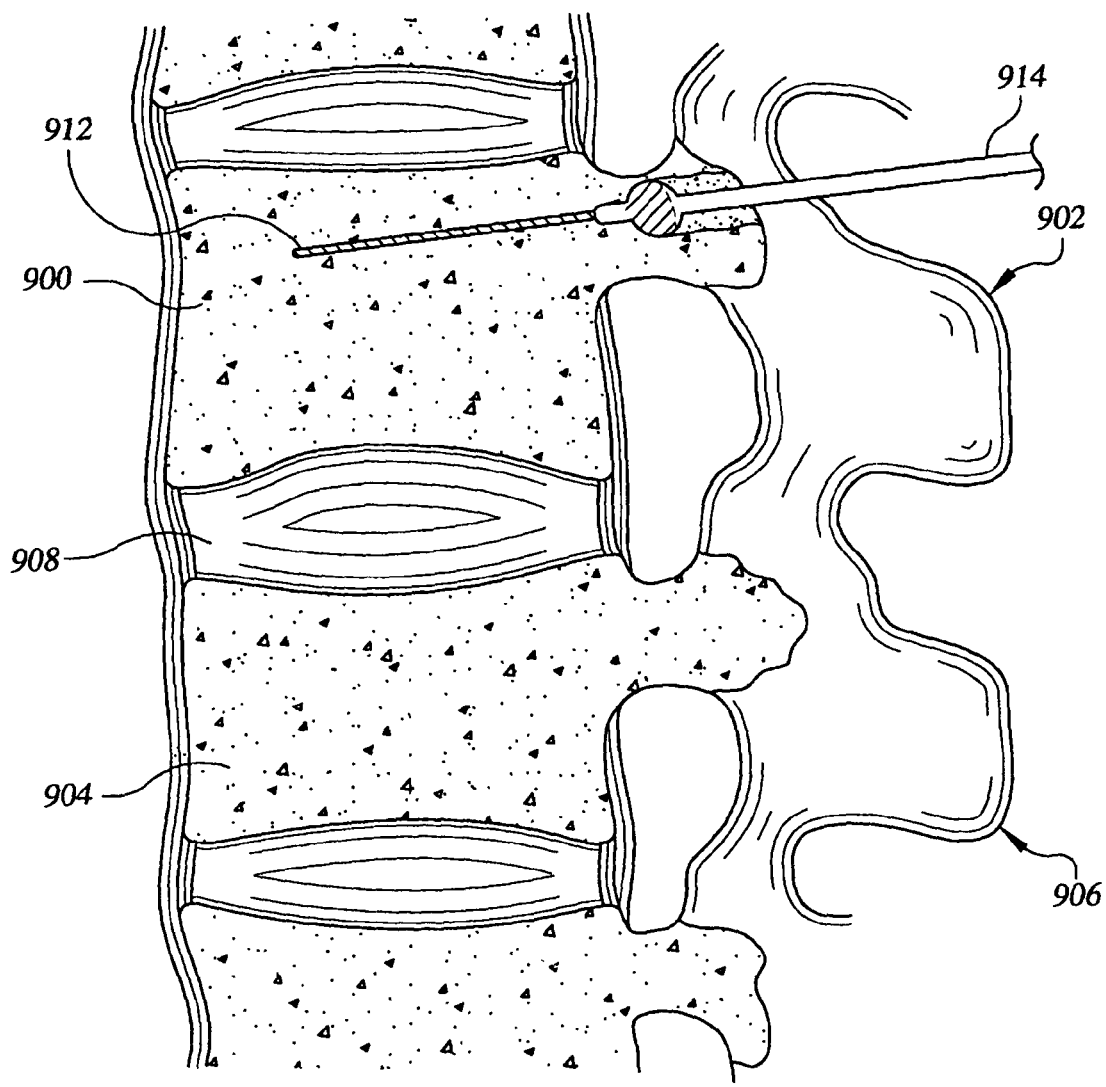

Next, a suitable, non-flexible bone drill 914 is inserted over the guidewire 912, as shown in FIG. 29, and the non-flexible bone drill 914 is actuated under guidance, thereby enlarging the channel created by the biopsy needle 910 and guidewire 912 to approximately 4.5 mm in diameter and extending into approximately the posterior third of the first vertebral body 900. In one embodiment, a straight drill sheath (not shown) such as a 0.25 mm thick, plastic tube having an outer diameter of 5 mm is inserted over the guidewire 912 through the connective tissues and musculature overlying the first vertebra 902 before inserting the straight drill, and the straight drill is inserted over the guidewire 912 but within the straight drill sheath. In this embodiment, the straight drill sheath protects the connective tissues and musculature (not shown) overlying the first vertebra 902 from contact with the non-flexible bone drill 914.

Figure 30:
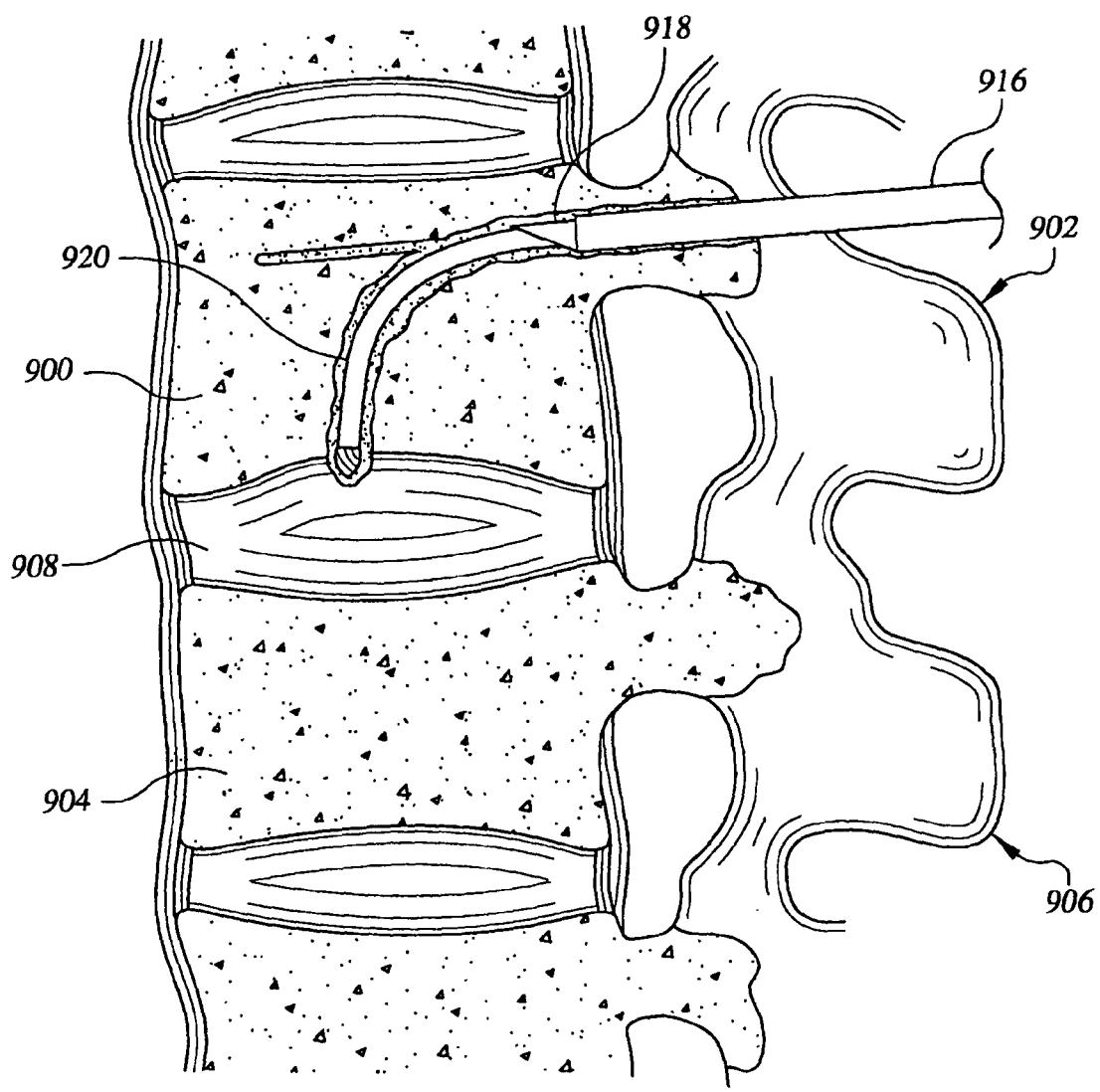
Figure 31:
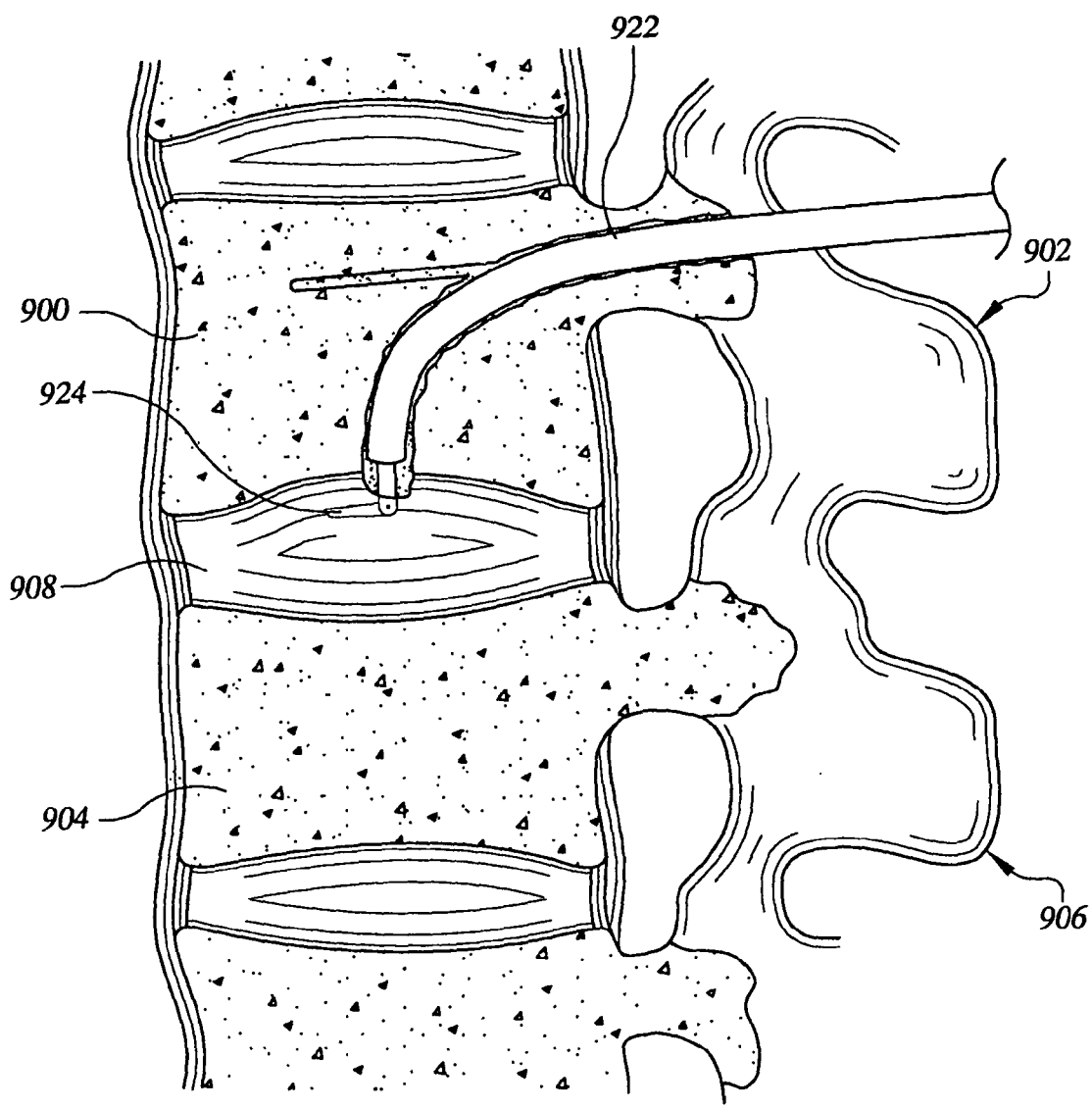
Figure 32:
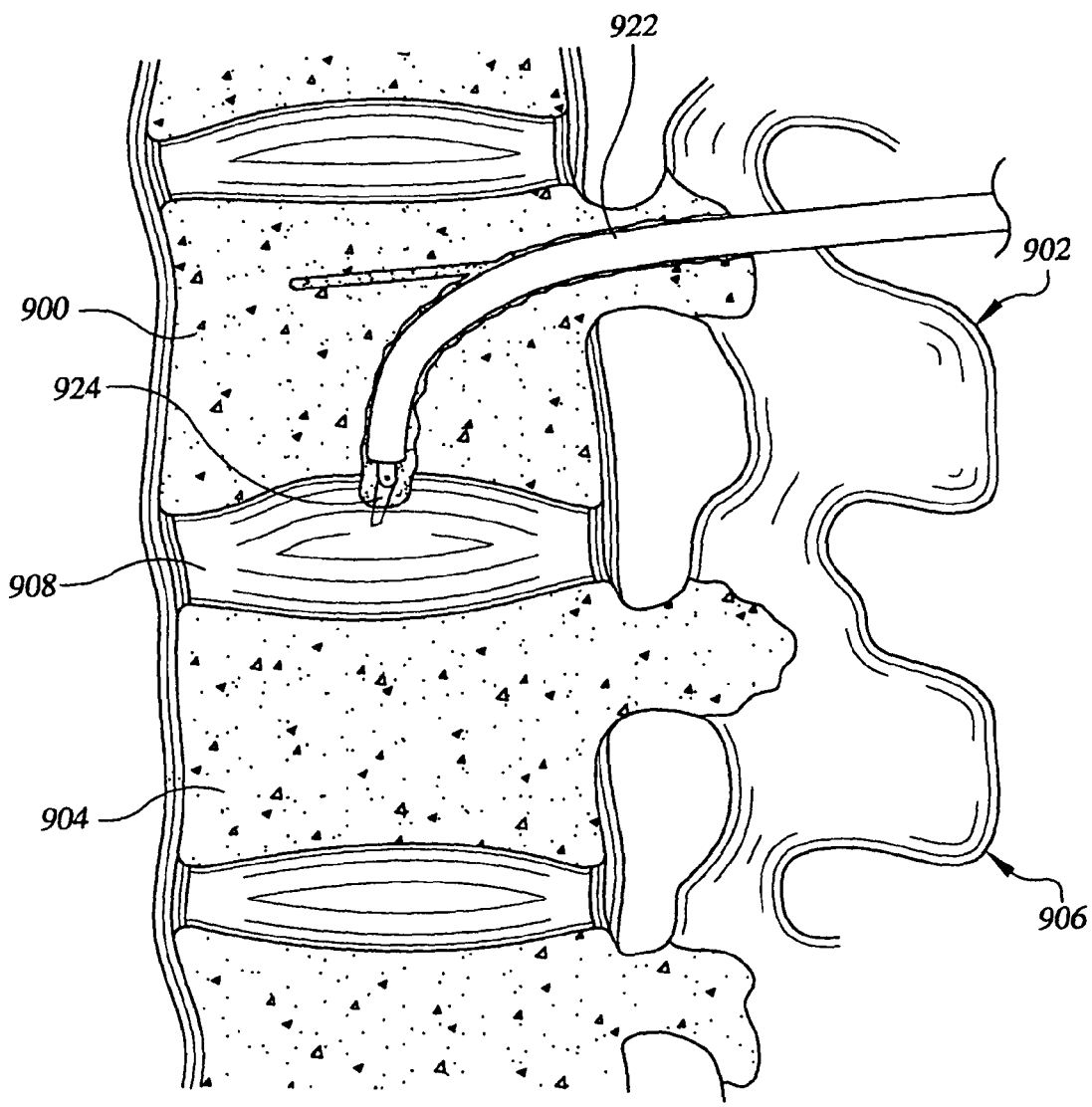
Figure 33:
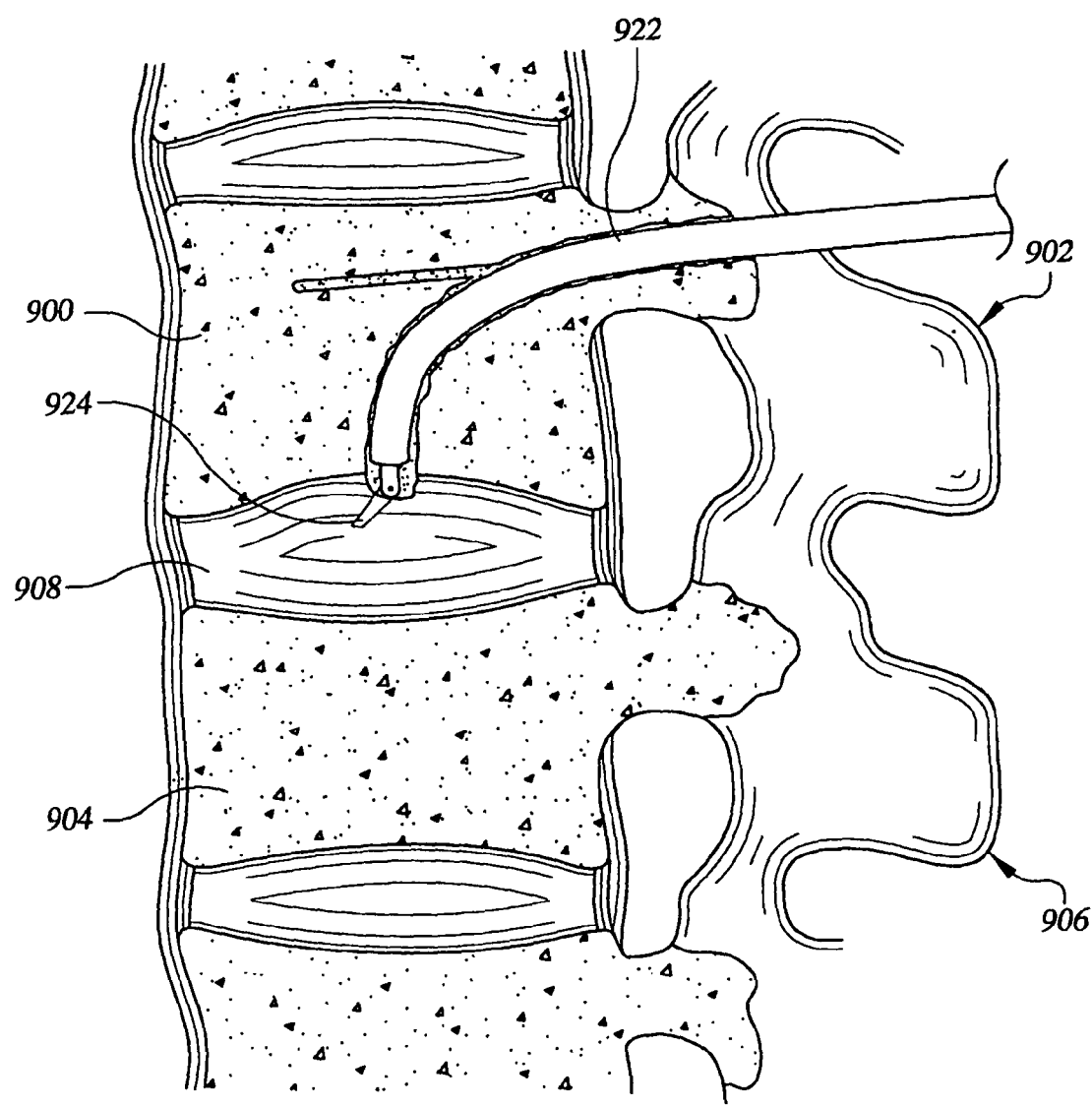
Figure 34:
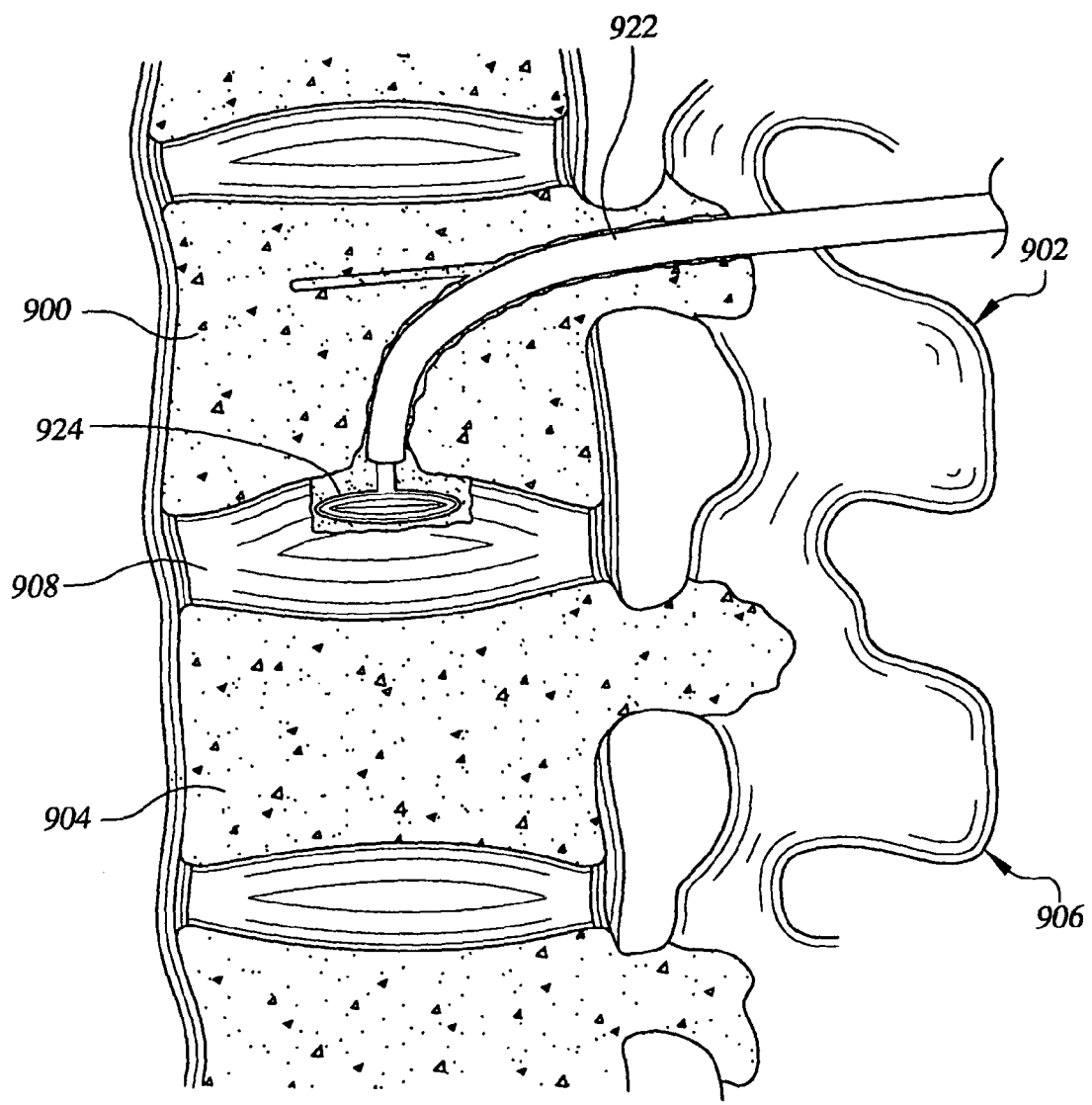

Next, the non-flexible bone drill 914 sheath is removed and, as can be seen in FIG. 30, replaced with a transpedicular working sheath 916 that is inserted over the non-flexible bone drill 914 into the space created by the non-flexible bone drill 914. The non-flexible bone drill 914 is removed and a retainer tube 918 is advanced through the transpedicular working sheath 916 until the distal tip of the retainer tube 918 exits the distal end of the transpedicular working sheath 916. Then, a first flexible drill 920 is introduced through the entire length of the retainer tube 918. In a preferred embodiment, the retainer tube 918 is a device according to the present invention. In another preferred embodiment, the flexible drill 920 is a device according to the present invention. As shown in FIG. 30, a flexible drill 920 is advanced through the proximal portion of the retainer tube 918 and out of the distal beveled end of the retainer tube 918 causing the long axis of a flexible drill 920 to make an approximately 90° angle with the long axis of the retainer tube 918. A flexible drill 920 is actuated, creating a channel through the first vertebral body 900 and into the intervertebral disk 908 in a superior to inferior direction.

Next, the first flexible drill 920 is removed. In a preferred embodiment, a biocompatible guidewire (not shown), between about 0.4 mm and 1 mm in diameter, is then inserted through the pathway and into the intervertebral disk 908 to create a support structure, leaving the support structure and transpedicular working sheath 916.

In a preferred embodiment, a second flexible drill (not shown) according to the present invention, but with a drilling tip having a larger cross-sectional diameter than the first flexible drill 920 is advanced through the transpedicular working sheath 916, and over the support structure if present. The second flexible drill is actuated, thereby enlarging the channel created by the first flexible drill 920 into the intervertebral disk 908. The final channel diameter, whether or not a second flexible drill is used, is preferably between about 4 mm and 5 mm in diameter. The second flexible drill, if used, and the transpedicular working sheath 916 are then withdrawn. If the remainder of the method is to be done using an over-the-wire technique, the support structure is left in place, if it is used, as will be understood by those with skill in the art with reference to this disclosure. The Figures, however, depict the method using non-over-the-wire technique.

Figure 35:
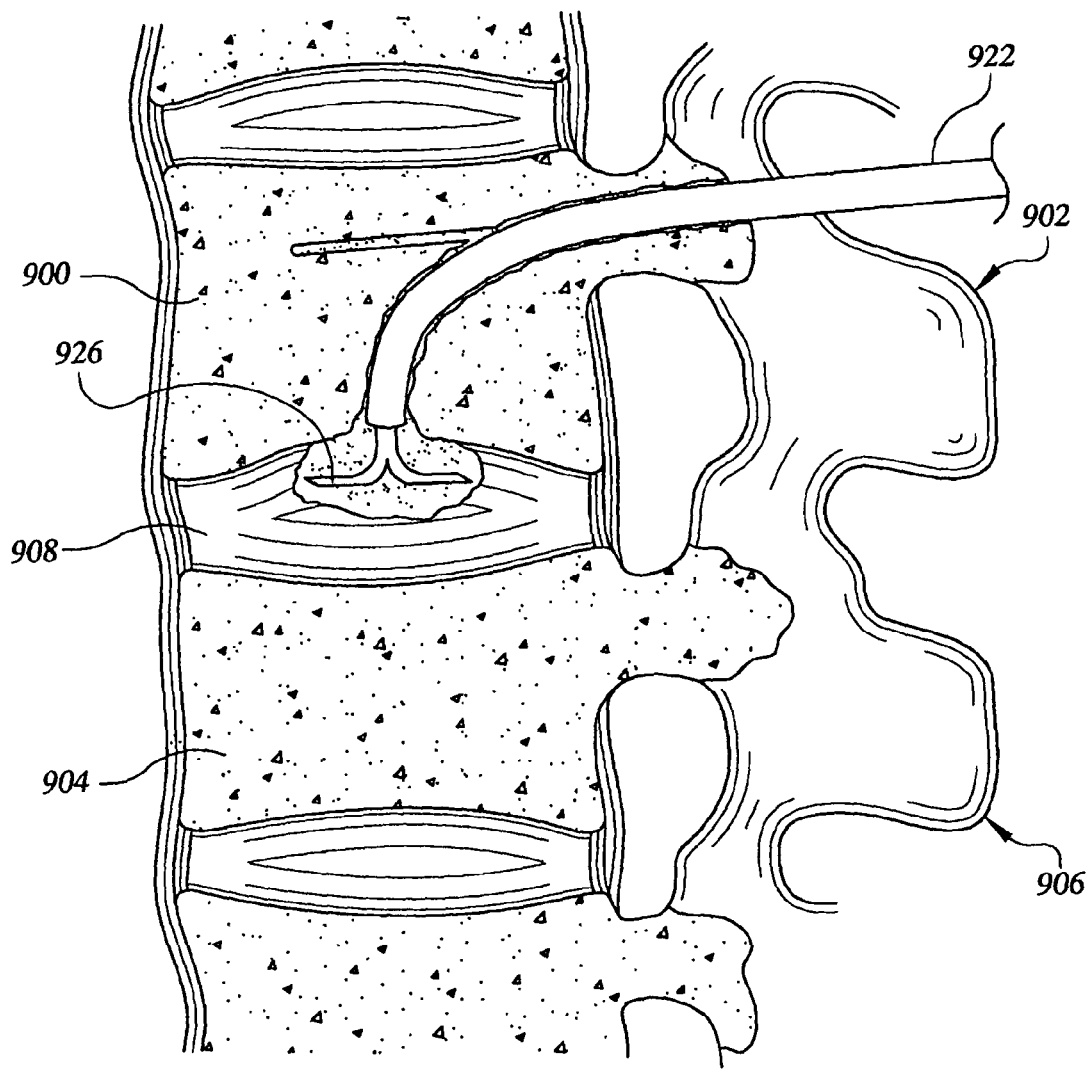
Figure 36:
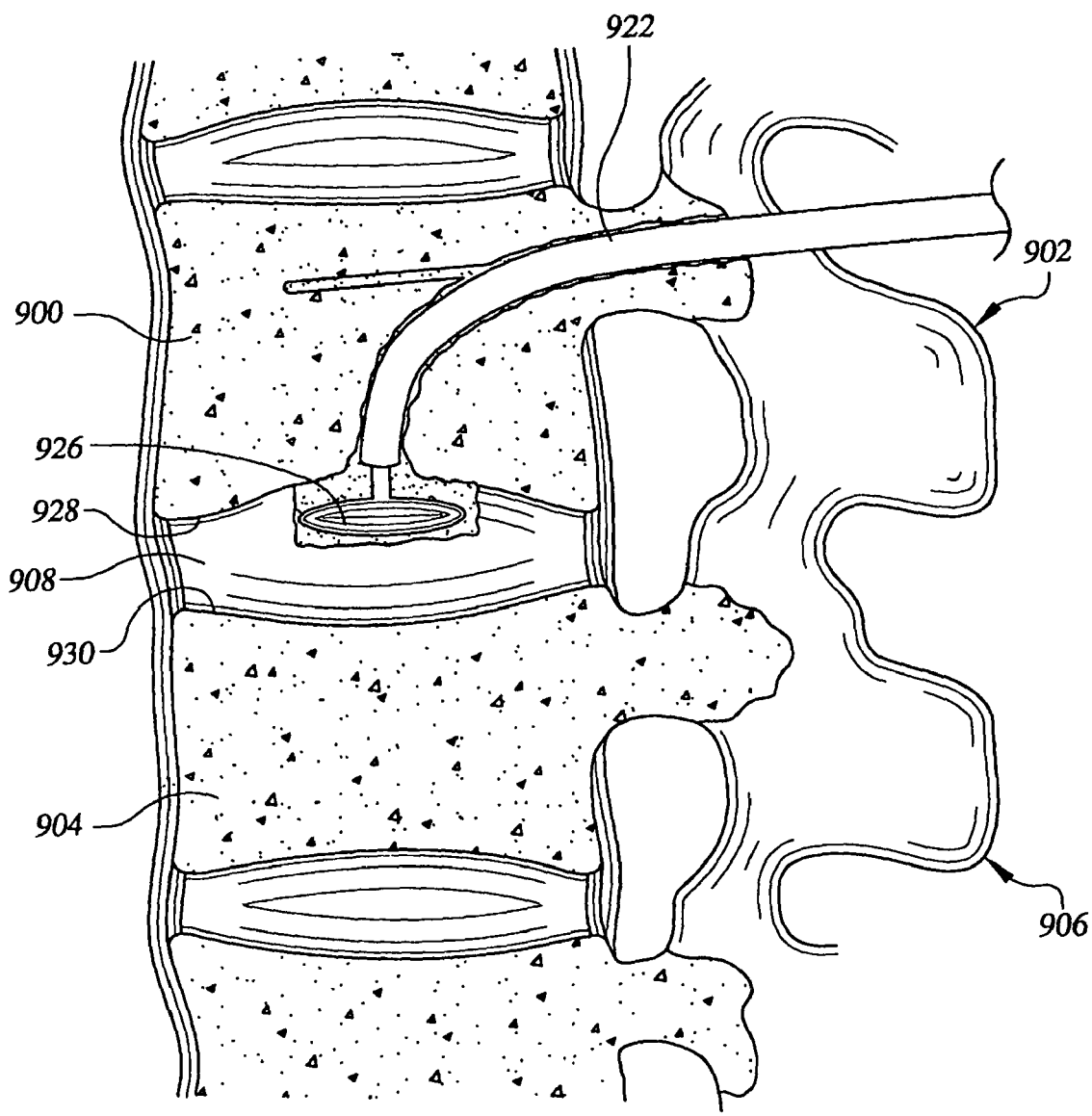

Next, as shown in FIG. 31, FIG. 32, FIG. 33 and FIG. 34, a flexible sheath 922, such as a flexible braided or metal sheath, is advanced over the support structure through the enlarged channel created by the flexible drill. Then, a cutting device 924 or an enucleation device 926, or an equivalent device, or more than one device sequentially, is advanced through the flexible sheath 922 until the distal end of the cutting device 924 or the enucleation device 926 is within the intervertebral disk 908. In one embodiment, the cutting device 924 is a device according to the present invention. In another embodiment, the enucleation device 926 is a device according to the present invention. The cutting device 924, if used, is then actuated as shown in FIG. 31, FIG. 32, FIG. 33 and FIG. 34, or the enucleation device 926, if used, is then actuated as shown in FIG. 35 and FIG. 36, under suitable guidance, such as fluoroscopic guidance, removing a section of intervertebral disk 908 material and, preferably, a portion of one or both endplates defining the intervertebral disk 908, preferably leaving cortical bone exposed on either the superior aspect 928 of the intervertebral disk 908, the inferior aspect 930 of the intervertebral disk 908, or preferably both the superior aspect 928 and the inferior aspect 930 of the intervertebral disk 908. In a preferred embodiment, the section of endplate removed comprises about 2 cm in sagittal cross-section. In a preferred embodiment, the section of endplate removed comprises about 30% of the endplate in sagittal cross-section. However, the annulus fibrosis is preferably preserved circumferentially. Then, the cutting device 924 or enucleation device 926 is removed and the debris is removed from the intervertebral disk 908 using suction, by flushing with a suitable solution such as saline, or by a combination of suction and flushing.

Figure 37:
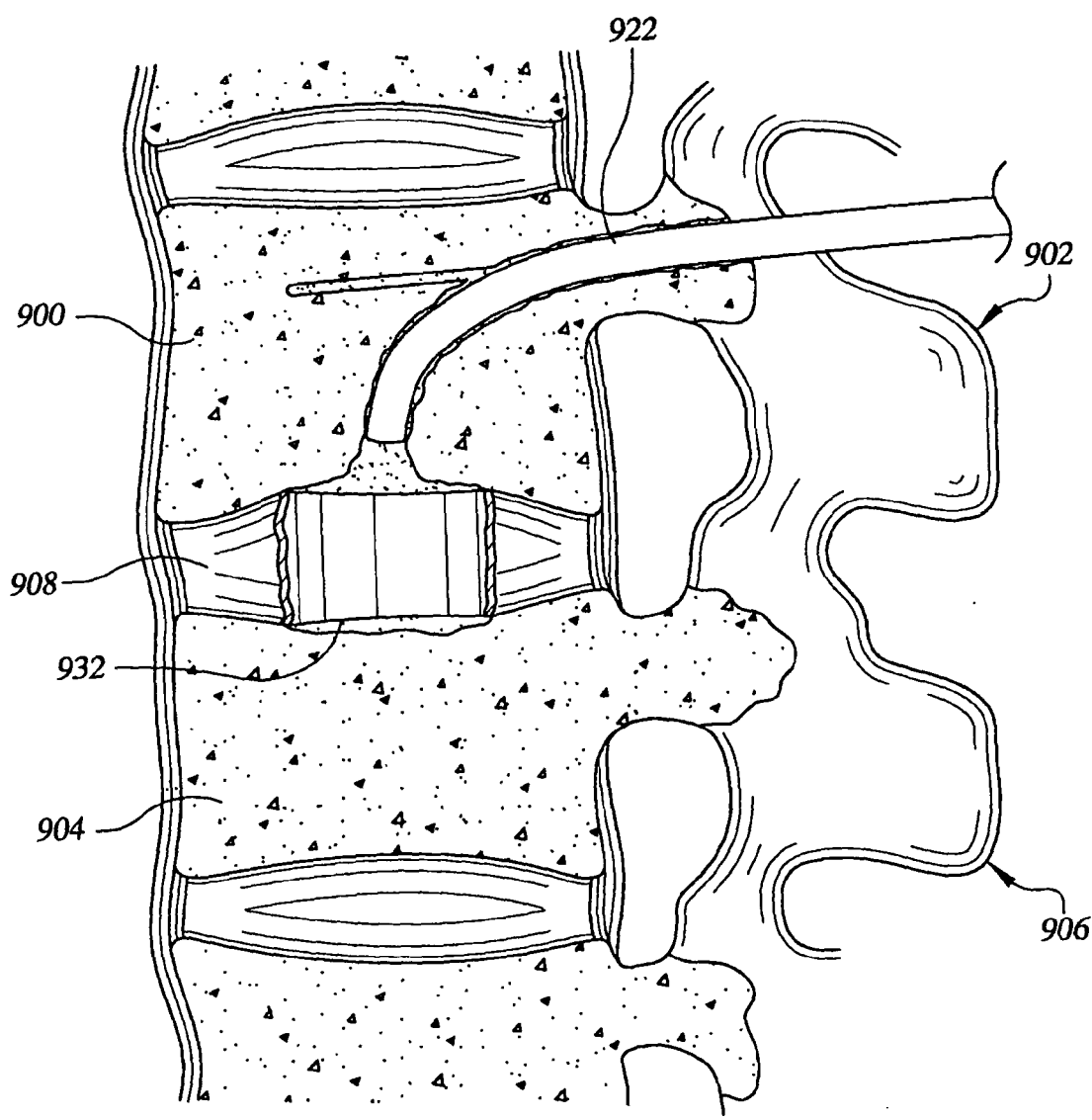

Next, as shown in FIG. 37 and FIG. 38, a fusion agent containment device 932 is introduced into the empty space created by the cutting device 924 or the enucleation device 926, or both, and deployed. In a preferred embodiment, as shown in FIG. 37 and FIG. 38, the fusion agent containment device 932 is a fusion agent containment device according to the present invention. However, other fusion agent containment devices are also suitable, as will be understood by those with skill in the art with reference to this disclosure. In another preferred embodiment, introduction and deployment of the fusion agent containment device 932 is accomplished by tightly coiling the fusion agent containment device 932 within a deployment device comprising a flexible tube for containing the coiled fusion agent containment device 932 and a central wire having a discharge tip for pushing the coiled fusion agent containment device 932 out of the flexible tube and into the empty space created by the enucleation device. Once in the empty space, the fusion agent containment device 932 returns to its unstressed shape, creating a lined chamber within the intervertebral disk 908. Next, the lined empty chamber is filled with a fusion agent, such as an agent comprising compatible bone matrix, thereby creating a boney fusion between the first vertebral body 900 and the second vertebral body 904. Suitable bone matrix, for example, is VITOSS™, available from Orthovita, Malvern, Pa. US and GRAFTON® Plus available from Osteotech, Inc., Eatontown, N.J. US, as well as demineralized cadaveric bone matrix material that has been mixed with a bone morphogenetic protein, with or without the patient's own bone marrow, to be both osteoconductive and osteoinductive.

In a preferred embodiment, as shown in FIG. 39, FIG. 40, FIG. 41, FIG. 42, FIG. 43 and FIG. 44, the method further comprises introducing a distraction system 934, 936, 938 into the chamber, either before filing the chamber with the fusion agent, or after filing the chamber with the fusion agent but before the fusion agent has set. Alternately, the chamber can be partially filled with a fusion agent, the distraction system 934, 936, 938 introduced before the fusion agent has set and an additional fusion agent can be added to the chamber. The distraction system 934, 936, 938 can be any suitable structure, as will be understood by those with skill in the art with reference to this disclosure. In a preferred embodiment, the distraction system 934, 936, 938 is a distraction system 934, 936, 938 according to the present invention. FIG. 31, FIG. 32, FIG. 33, FIG. 34, FIG. 35 and FIG. 36, show three such distraction systems 934, 936, 938 being deployed. The distraction system 934, 936, 938 serves to distract, that is, to increase axial separation of the first vertebra 902 from the second vertebra 906, and to provide support for the deposited fusion material.

Figure 45:
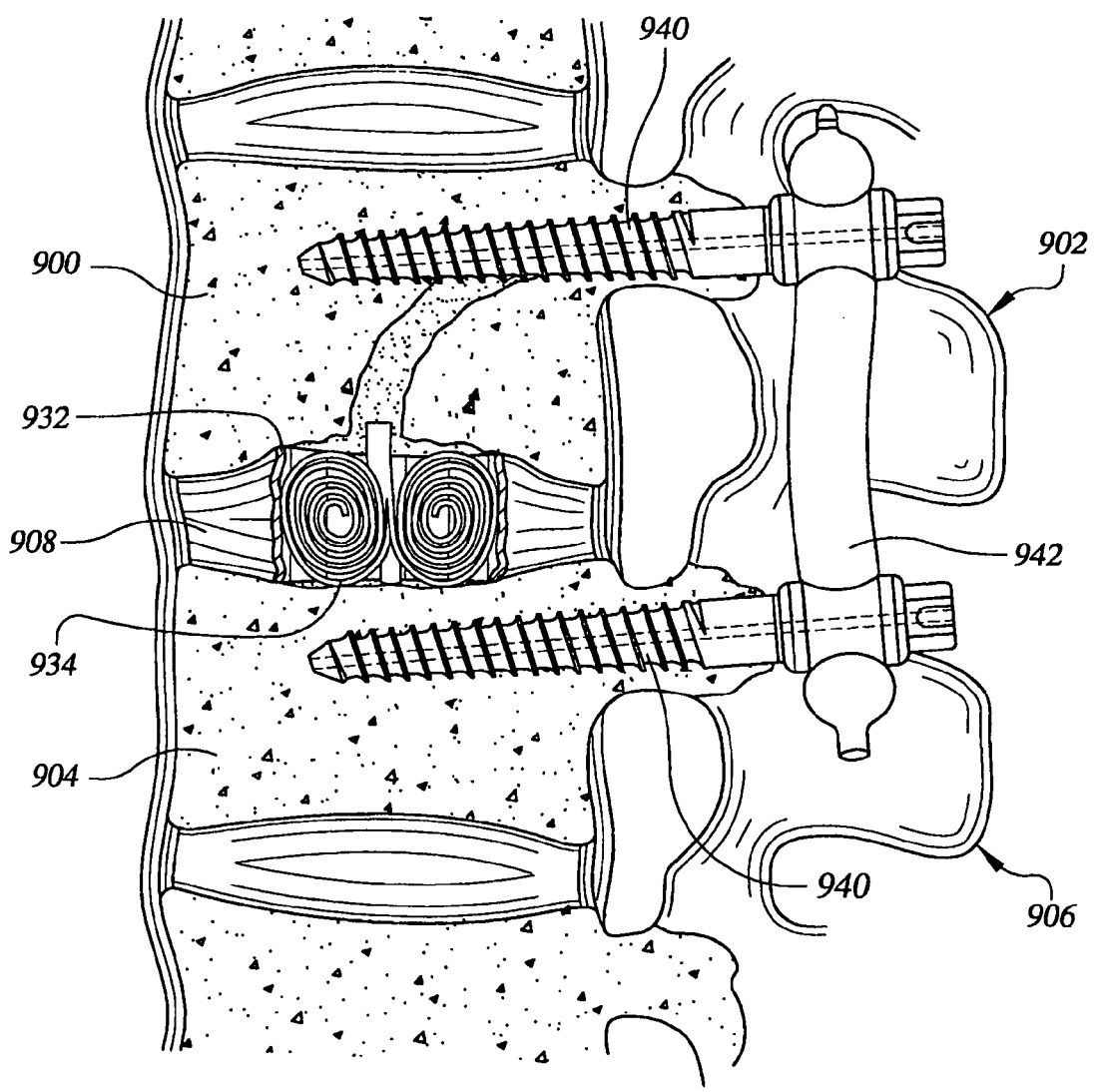
Figure 46:
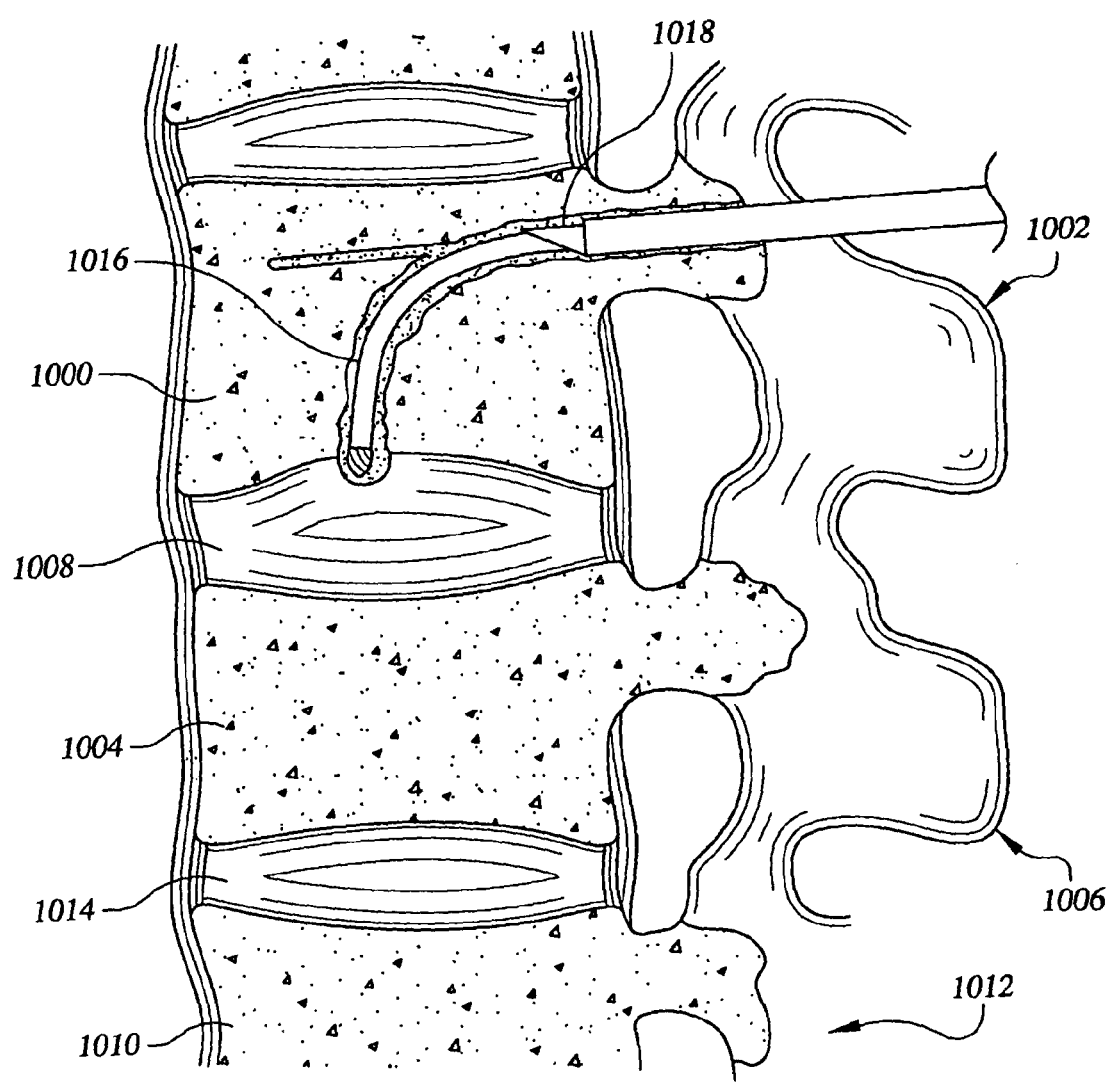
Figure 47:
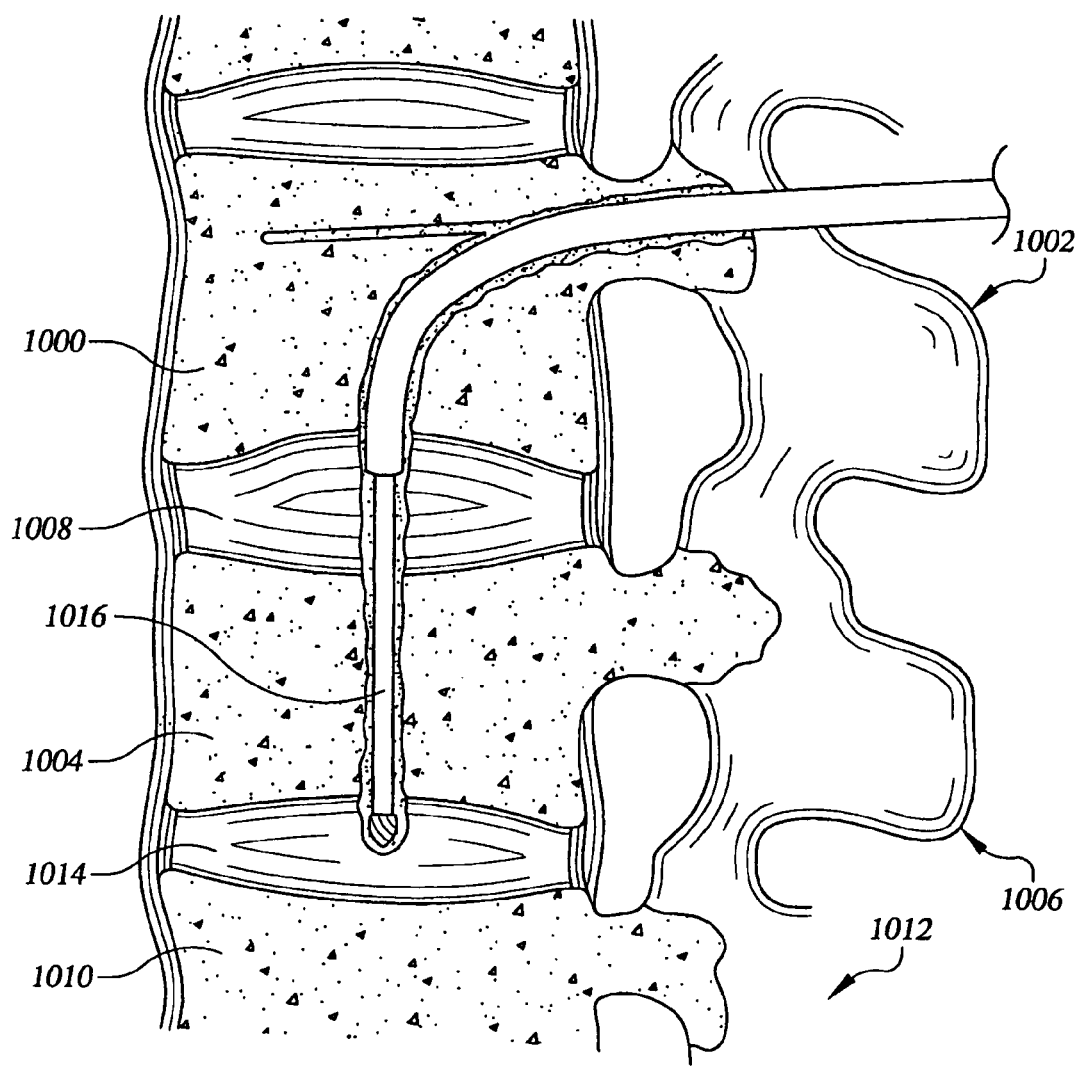
Figure 48:
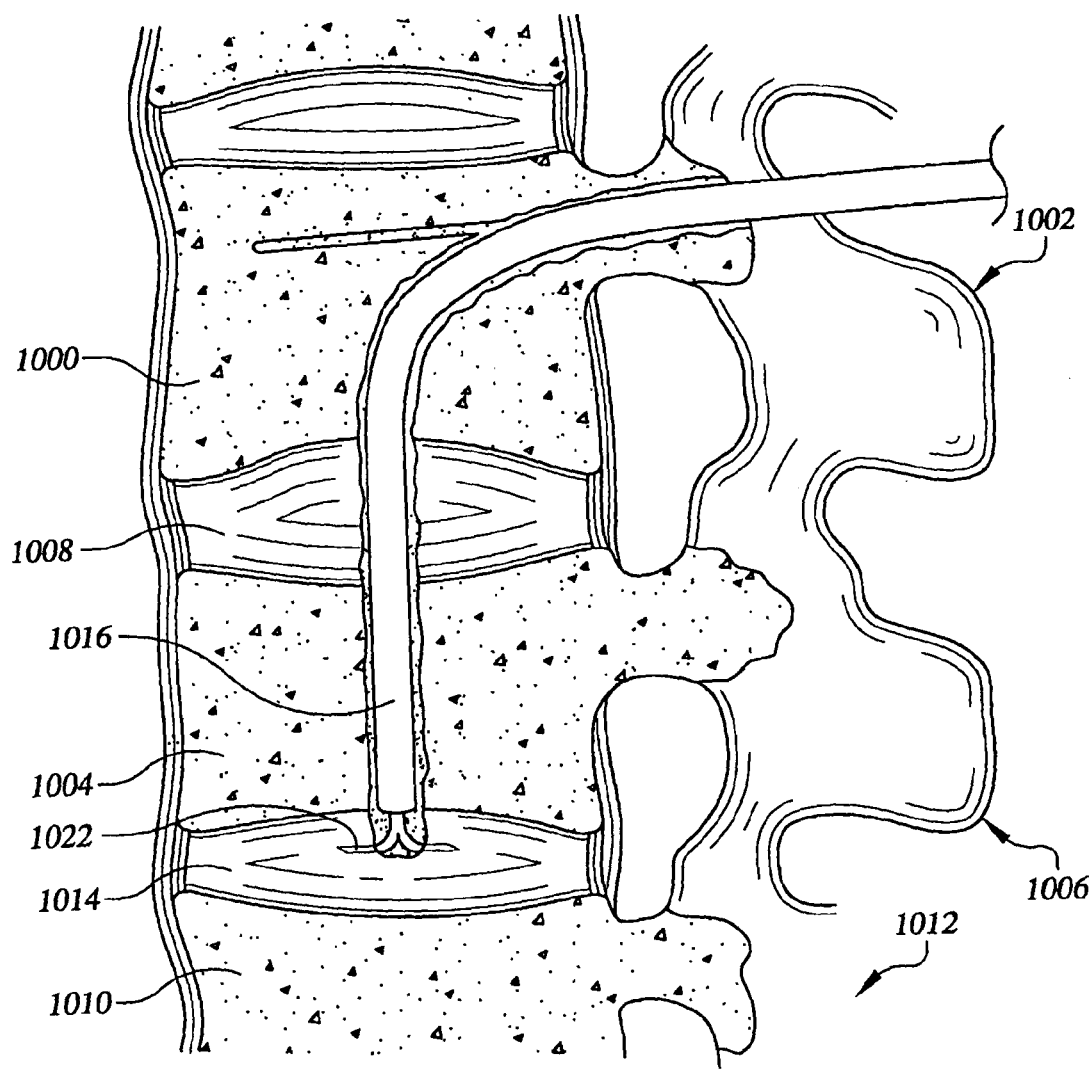
Figure 49:
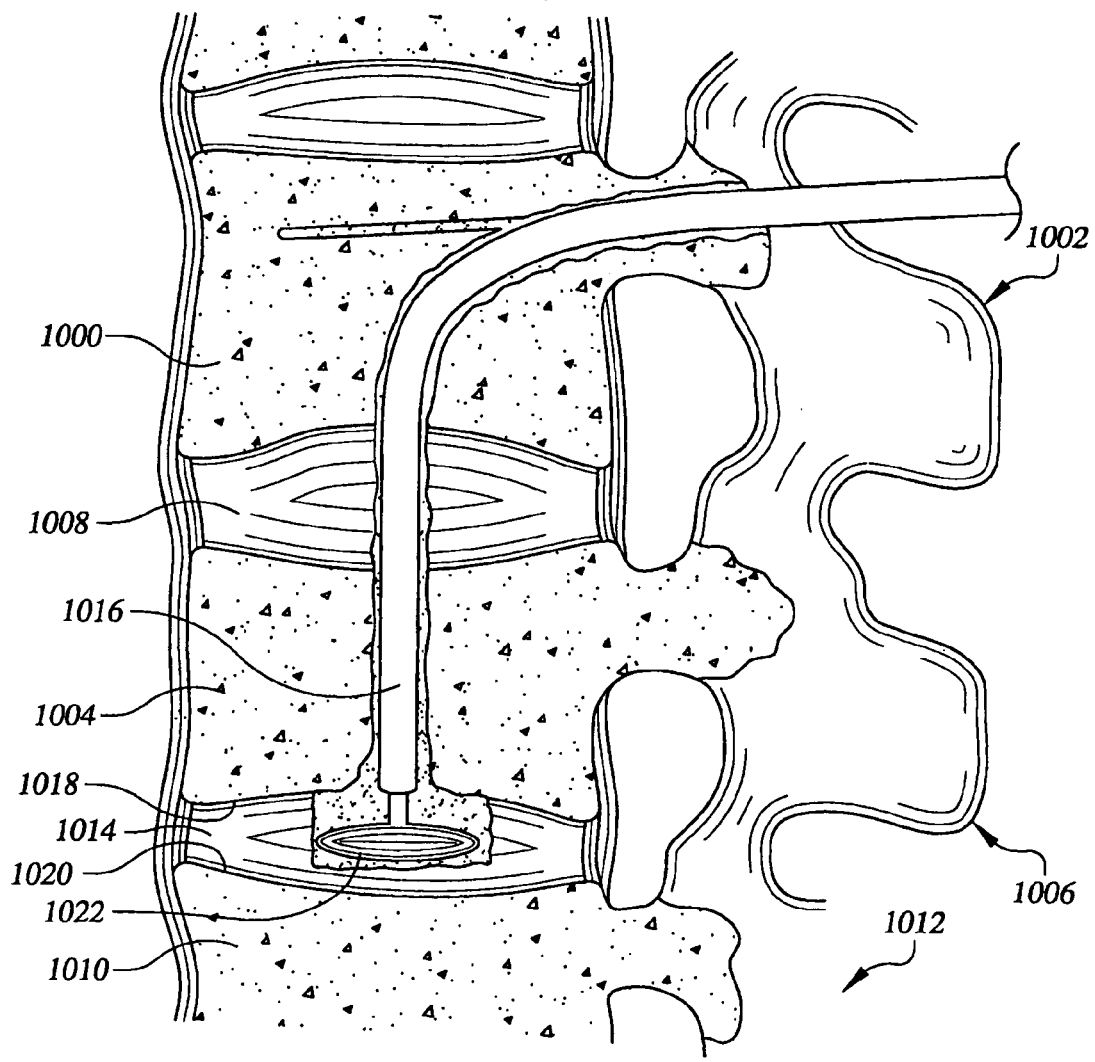
Figure 50:
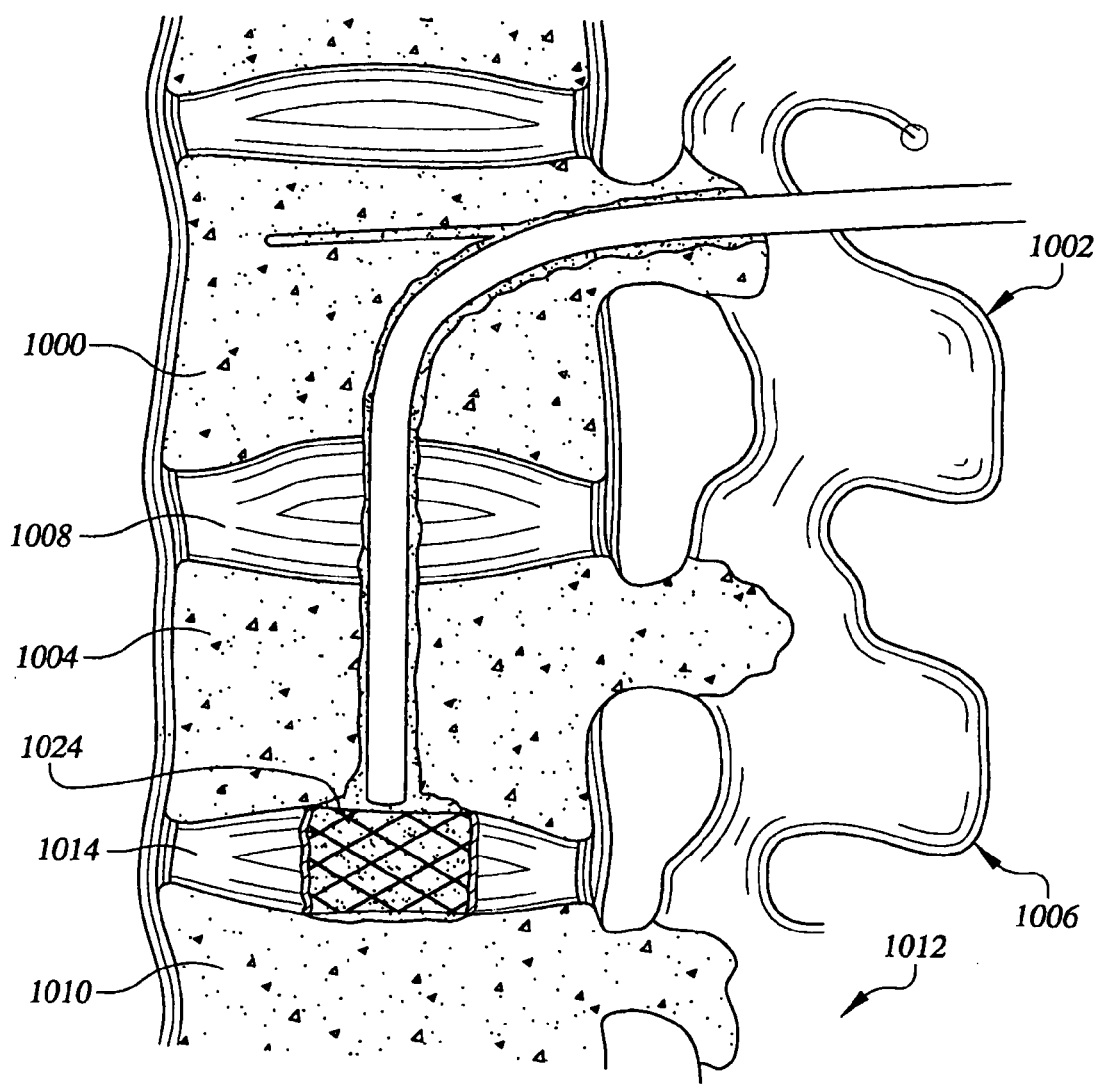
Figure 51:
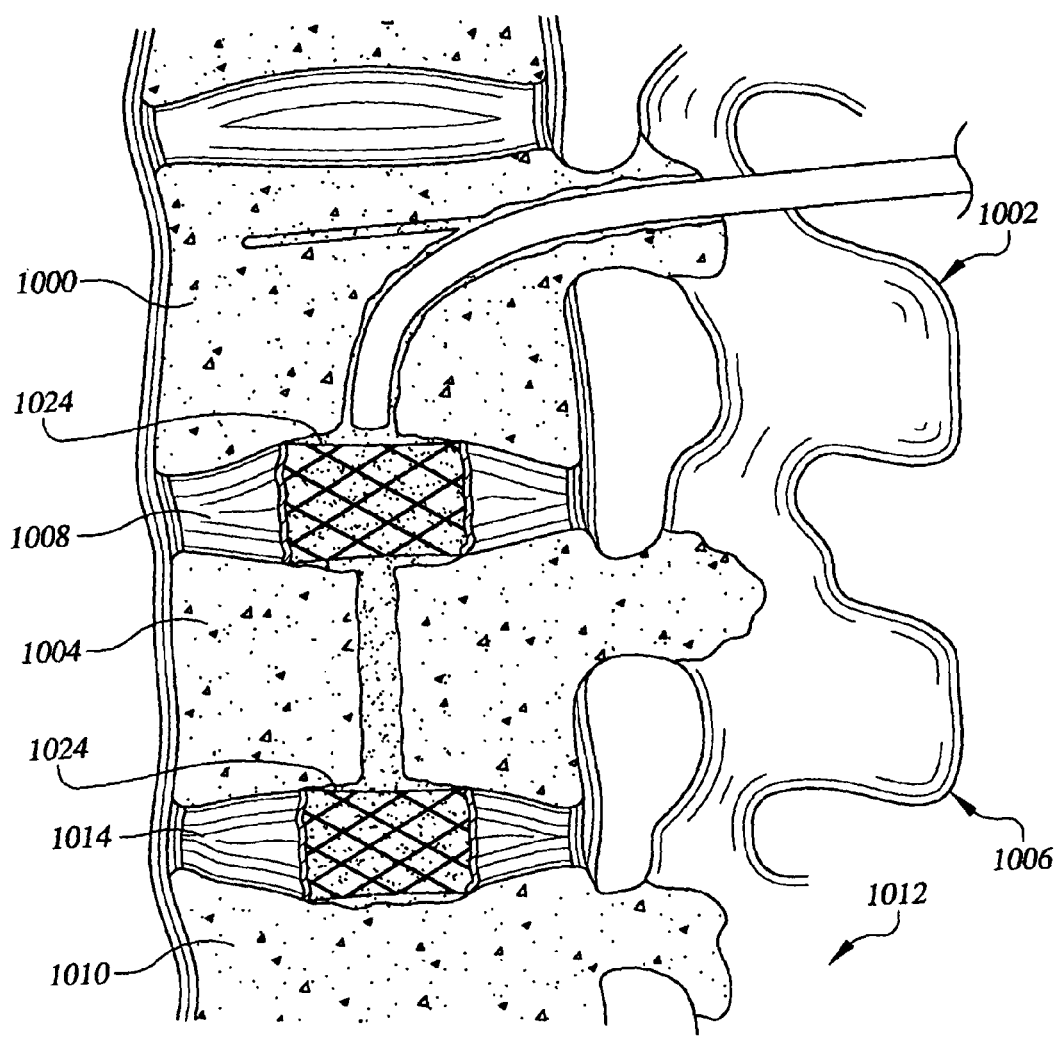
Figure 52:
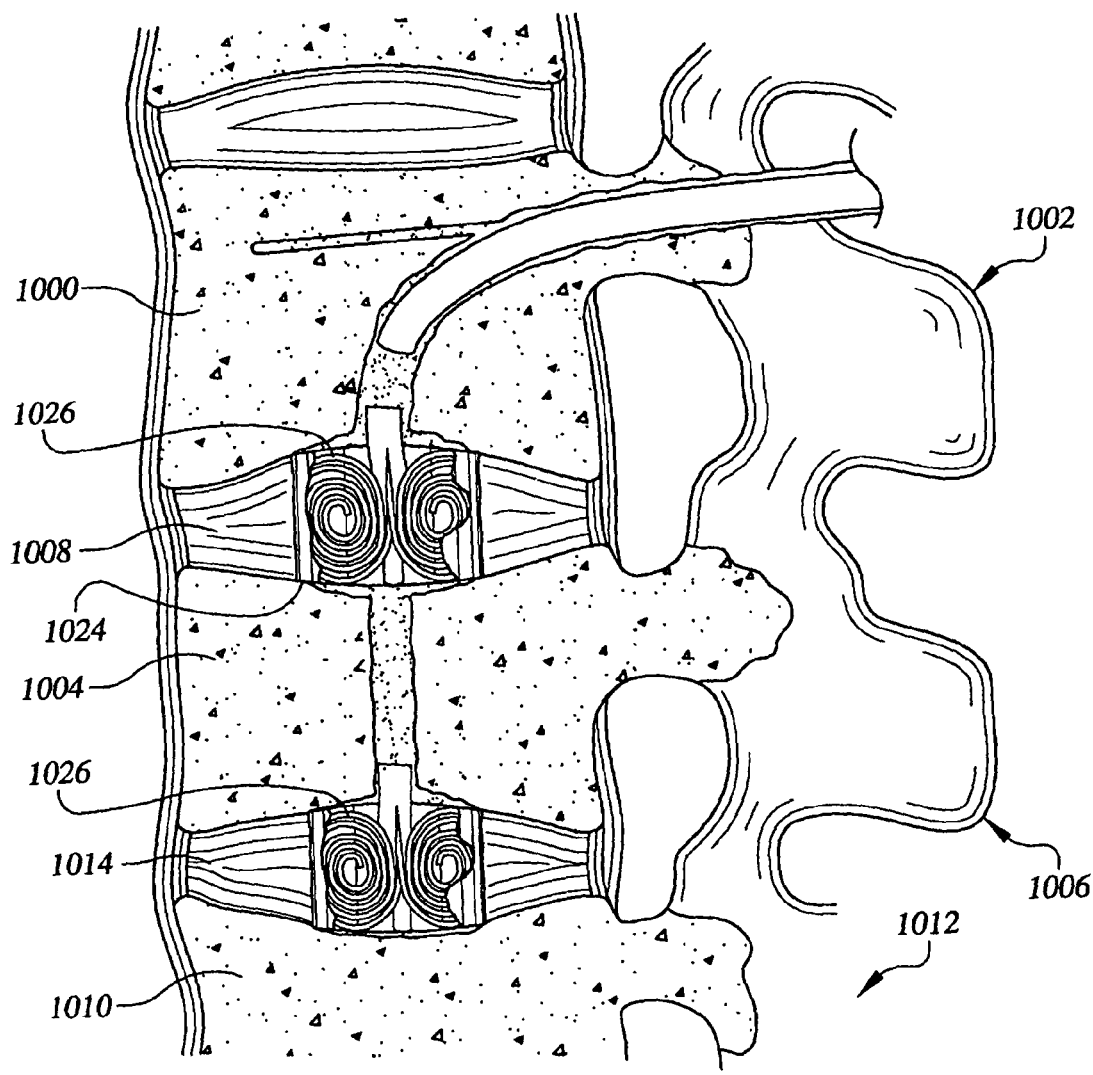

In a preferred embodiment, as shown in FIG. 45, the method further comprises performing an additional fusion procedure to join the first vertebra 902 to the second vertebra 906. In one embodiment, as can be seen in FIG. 45, the additional fusion procedure comprises placing pedicle screws 940 into the transpedicular channel left from performing the method of the present invention, and connecting the pedicle screws 940 by spacing devices 942, as will be understood by those with skill in the art with reference to this disclosure. However, any suitable additional fusion procedure can be used, as will be understood by those with skill in the art with reference to this disclosure.

In a preferred embodiment, the method is performed on at least three adjacent vertebral bodies and at the two intervertebral disks between the at least three adjacent vertebral bodies by accessing the vertebral bodies and intervertebral disks, either unilaterally or bilaterally, transpedicularly at only one vertebral level. Each aspect of this embodiment of the method corresponds to the equivalent aspect disclosed with respect to performing the method on only two adjacent vertebrae and the intervertebral disk between the two vertebrae, as will be understood by those with skill in the art with reference to this disclosure.

Referring now to FIG. 46 through FIG. 54, there are shown partial, cutaway, lateral perspective views illustrating some aspects of this embodiment of the method as performed on a first vertebral body 1000 of a first vertebra 1002, a second vertebral body 1004 of a second vertebra 1006, an intervertebral disk 1008 between the first vertebral body 1000 and second vertebral body 1004, a third vertebral body 1010 of a third vertebra 1012 and an intervertebral disk 1014 between the second vertebral body 1004 and third vertebral body 1010. As can be seen, after selecting a suitable patient, transpedicular access to the first vertebral body 1000 is obtained percutaneously and a non-flexible bone drill is used to access the intervertebral disk 1008 between the first vertebral body 1000 and the second vertebral body 1004 substantially as disclosed above. However, in this embodiment, a flexible drill 1016 is used to continue making a channel completely through the intervertebral disk 1008 between the first vertebra 1002 and second vertebral body 1004, FIG. 46, through the second vertebral body 1004 and into the intervertebral disk 1008 between the second vertebral body 1004 and the third vertebral body 1010, FIG. 47. Next, the intervertebral disk 1008 between the second vertebral body 1004 and the third vertebral body 1010, as well as a portion of the inferior endplate 1018 of the second vertebral body 1004 and the superior endplate 1020 of the third vertebral body 1010, are removed using a cutting device (not shown) or an enucleation device 1022 or both, or an equivalent device, FIG. 48 and FIG. 49. Then, a fusion agent containing device 1024 is deployed into the intervertebral 1014 between the second vertebral body 1004 and the third vertebral body 1010 and in the intervertebral disk 1008 between the first vertebral body 1000 and the second vertebral body 1004, FIG. 50. In a preferred embodiment, a distraction system 1026 is placed within the fusion agent containing device 1024 in both the intervertebral disk 1008 between the first vertebra 1002 and second vertebral body 1004, and the intervertebral disk 1008 between the second vertebral body 1004 and the third vertebral body 1010, FIG. 51, FIG. 52, FIG. 53 and FIG. 54. Next, each fusion agent containing device 1024 is filled with fusion agent, thereby fusing the first vertebra 1002 to the second vertebra 1006, and fusing the second vertebra 1006 to the third vertebra. Additionally, in a preferred embodiment, (not shown), an additional fusion procedure can be performed to join the first vertebra 1002 with the second vertebra 1006, to join the second vertebra 1006 with the third vertebra, or both, in a manner corresponding to FIG. 45.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference to their entirety.

What is claimed is:

1. A distraction system for distracting a superior vertebral body adjacent an inferior vertebral body comprising:
    a) an introducer comprising a proximal insertion portion and a distal anchoring portion comprising a plurality of barbs structurally configured to penetrate and anchor the distal anchoring portion to at least one of the superior and inferior vertebral bodies; and
    b) a plurality of independent, physically separable from each other, and deformable, spacing components;
    where each spacing component has a central opening and a plurality of extensions, the central opening extending completely through each spacing component; and
    where each spacing component is configured to independently stack onto the insertion portion of the introducer by the insertion portion being inserted through the central opening of each spacing component, the spacing components having an upper radially convex surface and lower radially concave surface, each radially convex surface having a contour matching and shaped to receive the radially convex surface of an adjacent, independent spacing component.

2. The distraction system of claim 1, where the plurality of extensions is selected from the group consisting of three extensions and four extensions.

3. A method of distracting a superior vertebral body from an inferior vertebral body comprising:
    a) providing the distraction system of claim 1;
    b) creating a chamber between the superior vertebral body and the inferior vertebral body;
    c) placing the distraction system in the chamber, thereby distracting the superior vertebral body from the inferior vertebral body.

4. The method of claim 3, where placing the distraction system is performed bilaterally.

5. The method of claim 3, where placing the distraction system comprises placing the distraction system through a sheath or hypotube, within a channel created through the pedicle of the superior vertebra.

6. The distraction system of claim 1, wherein the central opening extends through each of the spacing components.

7. The method of claim 3, wherein placing the distraction system in the chamber includes
    inserting the introducer into the chamber such that the plurality of barbs encounter at least one of the superior vertebra and the inferior vertebra to anchor the distraction system,
    inserting the plurality of spacing components in a deformed configuration along the introducer into the chamber, wherein the central opening for each of the plurality of spacing components is sized and shaped to received the proximal insertion portion of the introducer such that the plurality of spacing components are position able along the introducer into the chamber,
    expanding the plurality of spacing components into their undeformed configuration when positioned adjacent the plurality of barbs anchoring the distraction system within the chamber.

8. The distraction system of claim 1, wherein the introducer is flexible.

9. The distraction system of claim 1, wherein the distal anchoring portion is substantially transverse to the proximal insertion portion when the plurality of barbs penetrate and anchor the distal anchoring portion to at least one of the superior and inferior vertebral bodies.

10. The method of claim 3, further comprising forming a channel through one of the superior and inferior vertebral bodies to access an intervertebral disc space formed between the superior and inferior vertebral bodies.

11. The method of claim 10, wherein placing the distraction system in the chamber includes placing the distraction system through the channel formed in one of the superior and inferior vertebral bodies.

12. The distraction system of claim 1, wherein the plurality of deformable, spacing components are separate from one another.

13. A method of distracting a superior vertebra from an inferior vertebra comprising:
    providing a distraction system for distracting the superior vertebra from the inferior vertebra comprising:
        an introducer comprising a proximal insertion portion and a distal anchoring portion comprising a plurality of barbs for anchoring the distal anchoring portion to at least one of the superior and inferior vertebrae; and
        a plurality of deformable, spacing components;
        where each spacing component has a central opening and a plurality of extensions; and
        where each spacing component is configured to stack onto the insertion portion of the introducer;
    forming a channel that extends through a pedicle of one the superior and inferior vertebral bodies, and through an endplate of the one of the superior and inferior vertebral bodies to the intervertebral disc space;
    creating a chamber in the intervertebral disc space between the superior vertebra and the inferior vertebra through the channel; and
    placing the distraction system in the chamber through the channel, thereby distracting the superior vertebra from an inferior vertebra.

14. A method of distracting adjacent superior and inferior vertebral bodies defining a intervertebral disc space, the method comprising:
    providing a distraction system having
        an introducer comprising a proximal insertion portion and a distal anchoring portion comprising a plurality of barbs structurally configured to penetrate and anchor the distal anchoring portion to at least one of the superior and inferior vertebral bodies, and a plurality of deformable spacing components where each component has a central opening extending through the component and a plurality of extensions;

forming a channel through one of the superior and inferior vertebral bodies to access the intervertebral disc space;

inserting through the channel the introducer and penetrating at least one of the superior and inferior vertebral bodies with the plurality of barbs to anchor the introducer within the intervertebral disc space; and inserting through the channel the plurality of deformable spacing components to distract the superior and inferior vertebral bodies away from each other.

15. The method of claim 14, wherein the insertion of the plurality of deformable spacing components occurs after the insertion of the introducer.

16. The method of claim 14, wherein each spacing component is configured to stack onto the introducer by inserting each of the deformable spacing components onto the introducer through the central opening of each spacing component.

17. The method of claim 14, further comprising forming a chamber between the superior and inferior vertebral bodies by removing a portion of an endplate of one of the superior and inferior vertebral bodies.

18. The method of claim 17, further comprising positioning the introducer and the plurality of deformable spacing components in the chamber.

19. The method of claim 17, wherein forming the channel through one of the superior and inferior vertebral bodies to access the intervertebral disc space is formed through the pedicle of one of the superior and inferior vertebral bodies.

20. The method of claim 14, wherein the introducer is flexible such that a distal portion of the introducer is substantially transverse to a proximal portion of the introducer when the plurality of barbs penetrate and anchor the introducer to at least one of the superior and inferior vertebral bodies.

* * * * *